US005955579A

United States Patent [19]
Leonard et al.

[11] Patent Number: 5,955,579
[45] Date of Patent: Sep. 21, 1999

[54] ISLET-SPECIFIC HOMEOPROTEIN AND TRANSCRIPTIONAL REGULATOR OF INSULIN GENE EXPRESSION, HOXB13

[75] Inventors: James N. Leonard, Islin, N.J.; Marc R. Montminy, Encinitas, Calif.

[73] Assignees: Strang Cancer Prevention Center, New York, N.Y.; Salk Institute, La Jolla, Calif.

[21] Appl. No.: 08/437,607

[22] Filed: May 9, 1995

[51] Int. Cl.[6] .................................................. C07K 14/47
[52] U.S. Cl. ........................ 530/350; 530/324; 530/352
[58] Field of Search .................................... 530/350, 303, 530/324, 352; 536/24.1; 512/2, 12

[56] References Cited

U.S. PATENT DOCUMENTS

| | | | |
|---|---|---|---|
| 5,324,638 | 6/1994 | Tao et al. ................................ | 435/69.1 |
| 5,427,940 | 6/1995 | Newgard .............................. | 435/240.2 |

OTHER PUBLICATIONS

Reeck et al., Homology in proteins and nucleic acids: a terminology muddle and a way out of it, Cell., 50: 667, 1987.
Creighton, T.E., Proteins, W.H. Freeman and Company:New York, NY, pp. 82–83, 1984.
German et al., Regulation of insulin gene expression by glucose and calcium in transfected primary islet cultures, J. Biol. Chem., 265(36):22063–22066, Dec. 1990.
German et al., Synergistic activation of the insulin gene by LIM–homeo domain protein: building a functional insulin minienhancer complex, Genes Dev., 6:2165–2176, Dec. 1992.
Kennedy et al., Characterization of a cDNA encoding the insulin gene GAGA–binding factor, Pur–I, Biochem. Soc. Trans., 21(1): 178–180, 1993.
Ohlsson et al., IPF1, a homeodomain–containing transactivator of the insulin gene., EMBO J., 12(11): 4251–4259, Dec. 1993.
Krumlauf, 1994 Cell 78:191–201.
Peers et al, 1994, Molecular Endocrinology 8:1798–1806.
Petersen et al, 1994, Proc. Natl. Acad. Sci. USA 91:10465–10469.
Khan, K.D. et al. (1993). Proc. Natl. Acad. Sci. U.S.A. 90:6806–10.
Leonard et al, 1993, Molecular Endocrinology 7:1275–1283.
Muller, M. et al. (1993), EMBO. J. 12:4221–8.
Muller et al. (1993). Nature 366:129–135.
Shuai et al. (1993). Science 261:1744–6.
Songyang et al. (1993). Cell 72:767–78.
Watling et al. (1993). Nature 366:166–70.
Amster–Choder, O. and Wright, A. (1992). Science 257:1395–8.
Fu, X.–Y. (1992). Cell 70:323–335.
Fu et al. (1992). Proc. Natl. Acad. Sci. USA 89:7840–3.
Overduin et al. (1992). Cell 70:697–704.
Schindler et al. (1992). Proc. Natl. Acad. Sci. USA 89:7836–9.

Schindler et al. (1992). Science 257:809–13.
Shuai et al. (1992). Science 258:1808–12.
Veals et al. (1992). Mol. Cell. Biol. 12:3315–24.
Velazquez et al. (1992). Cell 70:313–22.
Waksman, G. et al. (1992). Nature 358:646–653.
Decker et al. 1991. EMBO J. 10:927–932.
Hempstead et al. (1991). Nature 350:678–683.
Kaplan et al. (1991). Nature 350:158–160.
Kessler et al. (1991). J. Biol. Chem. 266:23471–23476.
Koch et al. (1991). Science 252:668–674.
Lew et al. (1991). Mol. Cell. Biol. 11:182–191.
McKendry, R. et al. (1991). Proc. Natl. Acad. Sci. U.S.A. 88:11455–9.
Qureshi, S.A. et al. (1991). J. Biol. Chem. 266:20594–7.
Fu et al. (1990). Proc. Natl. Acad. Sci. USA 87:8555–8559.
Kessler et al. (1990). Genes & Dev. 4:1753–1765.
Levy, D., and Darnell, J.E. (1990). The New Biologist 2:923–928.
Reich et al. (1990). Proc. Natl. Acad. Sci. USA 87:8761–8765.
Brasier, A.R., Tata, J.E., and Habener, J.F. (1989). Biotechniques 7:1116–22.
Dale et al. (1989). Proc. Natl. Acad. Sci. 86:1203–1207.
Decker et al. (1989). EMBO J. 8:2009–2014.
Lew et al. (1989). Mol. Cell. Biol. 9:5404–5411.
Levy et al. (1989). Genes & Dev. 3:1362–1371.
Pellegrini et al. (1989). Mol. Cell. Biol. 9:4605–12.
Walaas, S.I. and Nairn, A.C. (1989). J. of Mol. Neurosci. 1:117–127.
Levy, D. E., Kessler, D. S., Pine, R., Reich, N. and Darnell, J. E. (1988). Genes & Dev. 2:383–393.
Celis, J. E., Justessen, J., Madsun, P.S., Lovmand, J., Ratz, G.P. and Celis, A. (1987). Leukemia 1:800–813.
Aguet, J. M., Denbie, Z. and Merlin, G. (1986). Cell 55:273–280.
Rudd, C. E. et al. (1988). Proc. Natl. Acad. Sci. USA 85:5190–5194.
Veilette, A., Bookman, M. A., Horak, E. M., and Bolen, J. B. (1988). Cell 55:301–308.
Chodosh, L. A., Carthew, R. W. and Sharp, P. A. (1986). Mol. Cell Biol. 6:4723–4733.

(List continued on next page.)

*Primary Examiner*—Stephen Walsh
*Assistant Examiner*—Claire M. Kaufman
*Attorney, Agent, or Firm*—Klauber & Jackson

[57] ABSTRACT

The invention relates to a homeoprotein regulator of insulin gene expression having the characteristics of: binding to an element of an insulin gene promoter; being modulated by a $Ca^{++}$-dependent CaM kinase IV; and having homology to a nucleotide sequence encoded by a Hox gene complex. Also included within the invention are DNA sequences encoding the homeoprotein regulators of insulin gene expression, antibodies directed to the homeoprotein regulators of insulin gene expression, and diagnostic and therapeutic materials and utilities for the homeoprotein regulators of insulin gene expression.

10 Claims, 36 Drawing Sheets

OTHER PUBLICATIONS

Evans, R. K., Johnson, J. D. and Haley, B. E. (1986). Proc. Natl. Acad. Sci. USA 83:5382–5386.

Larner, A. C., Chaudhuri, A. and Darnell, J. E. (1986). J. Biol. Chem. 261:453–459.

Friedman, R. L., Manly, S. P., McMahon, M., Kerr, I. M. and Stark, G. R. (1984). Cell 38:745–755.

Larner, A. C., Jonak, G., Cheng, Y. S., Kornat, B., Knight, E. and Darnell, J. E., Jr. (1984). Proc. Natl. Acad. Sci. USA 81:6733–6737.

Dignam et al. (1983). Nucl. Acids Res. 11:1475–89.

Garner, M. M. and Revan, A. (1981). Nuc. Acids Res. 9:3047–3059.

Fried, A., and Crothers, D. M. (1981) Nuc. Acids Res. 9:6505–6525.

Bryan, J.K. (1977). Anal. Biochem. 78:513–9.

Davis, B.J. (1964). Ann. N.Y. Acad. Sci. 121:404–27.

FIG. 1A

```
                                                  tgagagagc
                                                             6
                    ttgctgncccctagaaccccaccctcgctcccatgagccgatcattgcccc ATG GAG CCC GGC AAT TAT
                                                                         M   E   P   G   N   Y
                                                                                                  26
GCC ACC TTG GAC GGG GCC AAG GAT ATC GAA GGC TTG CTG GGA GCT GGA GGG GGT CGT CGG
 A   T   L   D   G   A   K   D   I   E   G   L   L   G   A   G   G   G   R   R
                                                                                                  46
AAT TTA GTC GCC CAC TCC CCA CTG GCT AGC CAT CCC GCA GCT CCA GAG CCA ACG CTG ATG CCG
 N   L   V   A   H   S   P   L   A   S   H   P   A   A   P   E   P   T   L   M   P
                                                                                                  66
ACT GTC AAC TAT GCC CCC TTG GAT CTG CCA GGC TCT GAA GAG CCA AAG CAG TGC CAC
 T   V   N   Y   A   P   L   D   L   P   G   S   A   E   P   K   Q   C   H
                                                                                                  86
CCT TGT CCT GGG GTG CCC CAG GGA GCA TCT CCA GCT CCT GTG CCT TAT GGC TAC TTT GGA
 P   C   P   G   V   P   Q   G   A   S   P   A   P   V   P   Y   G   Y   F   G
                                                                                                  106
GGC TAC TAC TCT TGC CGA GTA TCC AGG AGC TCA CTG AAA CCC TGT GCC CAG ACG GCC
 G   Y   Y   S   C   R   V   S   R   S   S   L   K   P   C   A   Q   T   A
                                                                                                  126
ACC CTG GCT ACT TAC CCT TCG GAA ACC CCT GCA CCT GGG GAG GAG TAT CCT AGC CGT CCC
 T   L   A   T   Y   P   S   E   T   P   A   P   G   E   E   Y   P   S   R   P
                                                                                                  146
ACC GAG TTT GCC TTC TAT CCG GGC TAC CCG GGA CCT TAC CAG CCT TAC ATG GCC AGT TAC CTG
 T   E   F   A   F   Y   P   G   Y   P   G   P   Y   Q   P   Y   M   A   S   Y   L
                                                                                                  166
GAT GTG TCT GTG GTG CAG ACC CTG GGG GCC CCT GGG GAG CCT CGC CAC GAC TCT CTG CTT
 D   V   S   V   V   Q   T   L   G   A   P   G   E   P   R   H   D   S   L   L
```

FIG. 1B

```
CCC GTG GAC AGT TAT CAG CCT TGG GCC CTG GCC GGT GGC TGG AAC AGC CAG ATG TGC TGC
 P   V   D   S   Y   Q   P   W   A   L   A   G   G   W   N   S   Q   M   C   C    186

CAA GGT GAA CAG AAC CCA CCA GGT CCA TTC TGG AAA GCA GCA TTT GCA GAG CCC AGT GTC
 Q   G   E   Q   N   P   P   G   P   F   W   K   A   A   F   A   E   P   S   V    206

CAG CAC CCT CCT CCC GAC GGC TGC GCC TTC CGC TTC CGC GGC AAA AAA CGC ATT CCC TAT
 Q   H   P   P   P   D   G   C   A   F   R   F   R   G   K   K   R   I   P   Y    226

AGC AAG GGG CAG TTG CGA GAG CTG GAG CGA GAG TAT GCG GCC AAC AAG TTT ATC ACC AAG
 S   K   G   Q   L   R   E   L   E   R   E   Y   A   A   N   K   F   I   T   K    246

GAC AAG AGG CGC GTC AAG ATC TCG GCA GCC ACC AGC CTC TCT GAA CGC CAG ATT ACC TGG
 D   K   R   R   V   K   I   S   A   A   T   S   L   S   E   R   Q   I   T   W    266

TTT CAG AAC CGC CGG AAG GAG AAG GTT CTT GCC AAG GTC AAG ACC ATC AGC ACT ACT
 F   Q   N   R   R   K   E   K   V   L   A   K   V   K   T   I   S   T   T       286

CCG TGA gcaccagtgggatgggcagggaaaggggcttgcctgagaattgggagcccgccagggccaggactgg            287
 P   * cagaggactcggctgaggaccccagagatgacacctttagcaggctactgattctgactattcctcgggctgtc
ctgcatgtgccagaagtggggtccggaatcacagtccccttcatcgtggttcagaagaacctgtatcagtcataatc
attcatccataaccagtactagttgtcatgataatttctcatatttctcatctagagctctgttgagcgcttagaaa
tcgctttcatgagttgagctgatcgcgaataaatttgaaccaagagccacaccacaacaaatcacctatctttatgct
catttcaattgcattctgattgcctcaaataaacttatactccgaaaaagcaaacccatatgaa
```

FIG.2A-1

```
                                                                GAAAGCTAGGGAGG
AGAGGAGGAAGAGGTGGGGCCCGGCCTCTCCGTCCCCTCTCCTCCGCCCACCAGCCTCCCCTCCCCCGGACGTG
TAAATGAGACTCTGCAAACTGGAAAGCACGGAAAGACACCTCCTCCTTTCTCTCTTGTGTTTTAAGTGGAATGAG
AGAGAGGAGTGAGAGGGCCAAAGAGAGAGGGAGNAGAGAGAGAGAGAGAAAGAGCCAGAGAGCCAGAGAGA
GAGACAGAGACAGAGAGAGAGAGAGAGAGAGAGAAAGAGAGAGAGAGAGAGAGAATAAGCTGG
GGTAAAGTATTTTCGCAGTTTCTCGCCCTTTAGGATTTTATTAGCTTCTCCCCCAGGCCCCAGCCAATCAGCGGCGTG
CCCGGGCCCCTGCGTCTCTTGCGTCAAGACGGCCGTGCTGAGCGAATGCAGGCGACTTGCGAGCTGGAGCCGATTTAAA
ACGCTTTGGATTCCCCCGGCCTGGGTGGGAGCCTGGGTGCCCCCTAGATTCCCCGCCCCCGCCACCTTCATGACGC

CGACCCTCGGCTCC ATG GAG CCC GGC AAT TAT GCC ACC TTG GAT GGA GCC AAG GAT ATC GAA   16
                M   E   P   G   N   Y   A   T   L   D   G   A   K   D   I   E

GGC TTG CTG GGA GCG GGA GGG CGG AAT CTG GTC GCC CAC TCC CCT CTG ACC AGC CAC   36
 G   L   L   G   A   G   G   G   R   N   L   V   A   H   S   P   L   T   S   H

CCA GCG GCG CCT ACG CTG ATG CCT GCT GTC AAC TAT GCC CCC TTG GAT CTG CCA GGC TCG   56
 P   A   A   P   T   L   M   P   A   V   N   Y   A   P   L   D   L   P   G   S
```

FIG.2A-2

```
GCG GAG CCG CCA AAG CAA TGC CAC CCA TGC CCT GGG GTG GCC CAG GGG ACG TCC CCA GCT
 A   E   P   P   K   Q   C   H   P   C   P   G   V   A   Q   G   T   S   P   A   76

CCC GTG CCT TAT GGT TAC TTT GGA GGC GCG TAC TAC TCC TGC CGA GTG TCC CGG AGC TCG
 P   V   P   Y   G   Y   F   G   G   A   Y   Y   S   C   R   V   S   R   S   S   96

CTG AAA CCC TGT GCC CAG GCA GCC ACC CTG GCC GCG TAC CCC GCG GAG ACT CCC ACG GCC
 L   K   P   C   A   Q   A   A   T   L   A   A   Y   P   A   E   T   P   T   A   116

GGG GAA GAG TAC CCC AGC CGC CCC ACT GAG TTT GCC TTC TAT CCG GGA TAT CCG GGA ACC
 G   E   E   Y   P   S   R   P   T   E   F   A   F   Y   P   G   Y   P   G   T   136

TAC CAG CCT ATG GCC AGT TAC CTG GAC GTG TCT GTG GTG CAG ACT CTG GGT GCT CCT GGA
 Y   Q   P   M   A   S   Y   L   D   V   S   V   V   Q   T   L   G   A   P   G   156

GAA CCG CGA CAT GAC TCC CTG TTG CCT GTG GAC AGT TAC CAG TCT TGG GCT CTC GCT GGT
 E   P   R   H   D   S   L   L   P   V   D   S   Y   Q   S   W   A   L   A   G   176

GGC TGG AAC AGC CAG ATG TGT TGC CAG GGA GAA CAG AAC CCA CCA GGT CCC TTT TGG AAG
 G   W   N   S   Q   M   C   C   Q   G   E   Q   N   P   P   G   P   F   W   K   196

GCA GCA TTT GCA G GTACCTCTATTACCCTGGGTCCCTGGGCTCTGAGCCTGGGGTTGTGGGTCCAATGGCAT
 A   A   F   A   D                                                              201
```

TTCCCTGGAGAGGAGGAGGAGGAGAGACTTGGAGCTGGTGAGGATGAGCTTGGGTGCTCTCCCTTGTTATTAGGACTCTG
AAGGAGGTCTGAGTAGCTGGAGGGCCTGATGGAGGTCAGTGTGAGGGCCTGAGCTGGGTGCTATCTGAAGCCTGAAG
GCCACCTCACTTCTCCAGGAGCCCTGGACCAGCCTTTCAACATGTCTGAGAGGTTTAGTCTCTTTGCTGTGAGTGG
GGATCAGGGTGTCCCTACCCAGCACAATTCCAAACTAATTCTACACAAAGCTAAATAACTCTCAATTCGGTGCGTGGG
GAGTGGGGTGTGGAGATGGGTAAAAGTATTGATGTAGAGAATACAACCTCTCACTTTCTATTAGATGAGTT
TTCCAATTTCCAAAGAAAAATTTAGGTTTCCTGCAGCCGTGACATATGTGTGCACTGGATGGTTAATGTGTGT
GTGTGTGTGTATGCGCATGTATTGGAGTGGGGCAGAAACGTGTTTCCAGAATTGCCTGAGAATCTAAAGAGTGG
CCAAGAGTCTGGAAATGCATGAAGACTGACGTATGTGATGGTGGGCAAAGGCCTGACTGTGTGTGTGTGGTATG
TTTGCAGATTCGCGGGTGTGAGAGCAGTGATGGGTGAGGGTGCCTTCAGGAGCCAAGGCTGAGCCGTGAGAGAAC
AAGCCCGAAGCCAGGGTGCGTCTCCTGTATGCTTTGGAGAACAGGAGTTGCACTGCNCCTGAGGGTGACCTGTGTG
CACCTGTGAGATGACTTAGCTTGGGCCTTGCAAGGCCCTGGGTCTGCATGGGTGGTATCTGACCATGCCTTTCCTCCC

TCCCTTTCACGCCCGGCAG AC TCC AGC GGG CAG CAC CCT CCT GAC GCC TGC GCC TTT CGT CGC
                     S   S   G   Q   H   P   P   D   A   C   A   F   R   R

FIG. 2A-4

```
GGC CGC AAG AAA CGC ATT CCG TAC AGC AAG GGG CAG TTG CGG GAG CTG CGG GAG TAT    235
 G   R   K   K   R   I   P   Y   S   K   G   Q   L   R   E   L   R   E   Y

GCG GCT AAC AAG TTC ATC ACC AAG GAC AAG AGG CGC AAG ATC TCG GCA GCC ACC CTC    255
 A   A   N   K   F   I   T   K   D   K   R   R   K   I   S   A   A   T   L

TCG GAG CGC CAG ATT ACC ATC TGG TTT CAG AAC CGC CGG GTC AAA GAG AAG AAG GTT CTC  275
 S   E   R   Q   I   T   I   W   F   Q   N   R   R   V   K   E   K   K   V   L

GCC AAG GTG AAG AAC AGC GCT ACC CCT TAA GAGATCTCCTGCCTGGGTGGAGGAGGAAAGTGGGG    284
 A   K   V   K   N   S   A   T   P   *
GTGTCCTGGGAGACCAGGAACCTGCCAAGCCTGTGGGCTGAGAGGCCCCTAGAGACAACACC
CTTCCCAGCCACTGGCTGCTGACTGTTCCTGAGAGCGGCCTGGTACCCAGTATGTCAGGAGACGAACCCCAT
GTGACAGCCCACTCCACCAGGGTTCCCAAAGAACCTGGCCCAGTCATAATCATTCATCCTGACAGTGGCAATAATCACG
ATAACCAGTACTAGCTGCCATGATGTTAGCCTCATATTTCTATCTAGAGCTCTGTAGCACTTTAGAAACCGCTTT
CATGAATTGAGCTAATTATGAATAAATTTGGAAGGCGATCCCTTTGCAGGGAAGCTTTCTCTCAGACCCCTTCCATTA
CACCTCTCACCCTGTAACAGCAGGAAGACTGAGGAGGGGAACGGGCAGATTCGTTGTGTGGCTGTGATGTCCGTTT
AGCATTTTTTCTCAGCTGACAG
```

FIG.2B-1

```
ttgctgncccctagaaccccaccctcggctccccatgagccgatcattgccccc ATG GAG CCC GGC AAT TAT    6
                                                        M   E   P   G   N   Y GCC ACC TTG GAC GGG GCC AAG GAT ATC GAA GGC TTG CTG GGA GCT GAA GGG GGT CGT CGG   26
 A   T   L   D   G   A   K   D   I   E   G   L   L   G   A   E   G   G   R   R AAT TTA GTC GCC CAC TCC TCC CCA CTG GCT AGC CAT CCC GCA GCT CCA ACG CTG ATG CCG   46
 N   L   V   A   H   S   S   P   L   A   S   H   P   A   A   P   T   L   M   P ACT GTC AAC TAT GCC CCC TTG GAT CTG CCA GGC TCT GCA GAG CCA AAG CAG TGC CAC       66
 T   V   N   Y   A   P   L   D   L   P   G   S   A   E   P   K   Q   C   H CCT TGT CCT GGG GTG CCC CAG GGG GCA TCT CCA GCT CCT GTG CCT TAT GGC TAC TTT GGA   86
 P   C   P   G   V   P   Q   G   A   S   P   A   P   V   P   Y   G   Y   F   G GGC GGG TAC TAC TCT TGC CGA GTA TCC AGG AGC TCA CTG AAA CCC TGT GCC CAG ACG GCC  106
 G   G   Y   Y   S   C   R   V   S   R   S   S   L   K   P   C   A   Q   T   A ACC CTG GCT ACT TAC CCT TCG GAA ACC CCT GCA CCT GGA GAG TAT CCT AGC CGT CCC      126
 T   L   A   T   Y   P   S   E   T   P   A   P   G   E   Y   P   S   R   P ACC GAG TTT GCC TTC TAT CCG GGC TAC CAG CCT ATG GCC AGT TAC CTG                  146
 T   E   F   A   F   Y   P   G   Y   Q   P   M   A   S   Y   L GAT GTG TCT GTG GTG CAG ACC CTG GGG GCC CCT GGG GAG CCT CGC CAC GAC TCT CTG CTT  166
 D   V   S   V   V   Q   T   L   G   A   P   G   E   P   R   H   D   S   L   L
```

FIG. 2B-2

```
CCC GTG GAC AGT TAT CAG CCT TGG GCC CTG GCC GGT GGC TGG AAC AGC CAG ATG TGC TGC
 P   V   D   S   Y   Q   P   W   A   L   A   G   G   W   N   S   Q   M   C   C    186

CAA GGT GAA CAG AAC CCA CCA GGT CCA TTC TGG AAA GCA GCA TTT GCA GAG CCC AGT GTC
 Q   G   E   Q   N   P   P   G   P   F   W   K   A   A   F   A   E   P   S   V    206

CAG CAC CCT CCT CCC GAC GGC TGC GCC TTC CGC GGC CGC AAA AAA CGC ATT CCC TAT
 Q   H   P   P   P   D   G   C   A   F   R   G   R   K   K   R   I   P   Y        226
                                           R   G   R   K   K   R   I   P   Y

AGC AAG GGG CAG TTG CGA GAG CTG CGA GAG TAT GCG GCC AAC AAG TTT ATC ACC AAG
 S   K   G   Q   L   R   E   L   R   E   Y   A   A   N   K   F   I   T   K        246
 S   K   G   Q   L   R   E   L   R   E   Y   A   A   N   K   F   I   T   K

GAC AAG AGG CGC AAG ATC TCG GCA ACC AGC CTC TCT GAA CGC CAG ATT ACC ATC TGG
 D   K   R   R   K   I   S   A   A   T   S   L   S   E   R   Q   I   T   I   W    266
 D   K   R   R   K   I   S   A   A   T   S   L   S   E   R   Q   I   T   I   W

TTT CAG AAC CGC CGG GTC AAG GAG AAG AAG GTT CTT GCC AAG GTC AAG ACC AGC ACT ACT
 F   Q   N   R   R   V   K   E   K   K   V   L   A   K   V   K   T   S   T   T    286
 F   Q   N   R   R   V   K   E   K   K   V   L

CCG TGA  gcaccagtggggatgggcagggaaaggggcttggcctggagaattgggagcccgccagggccaggactgg
 P   *                                                                            287 cagaggactcggctgagggaccccaagagatgacaccttagcaggctactgagttctgactattcctcgggctgtc
ctgcatgtgccagaagtgggggtccggaaatcacagtcccctttcatcgtggttcagaagaacctgtatcagtcataatc
attcatccataaccagtactagttgtcatgataattagcctcatatttctatctagagctctgttgagcgcttagaaa
tcgctttcatgagttgagctgatcgcaaaaaatttgaaccaaagagccacaccaaacaatcaccttatctttatgct
catttcaattgcattctgattgcctcaaataactatactccgaaaagcaaacccatatgaa
```

Probe : FLAT

FIGURE 8

1. HOX-A13

AC   P31271 (Database accession number for HOX-A13)
DT   01-JUL-1993 (Date sequence created in database; no subsequent update or annotation)
DE   HOMEOTIC PROTEIN HOX-A13 (HOX-1J) (FRAGMENT) (Name of database sequence)

SCORES    80.3% identity in 66 aa overlap

```
              190       200       210       220       230       240       250       260       270       280
rCIX-1  EQNPPGPFWKAAFAEPSVQHPPPDGCAFRRGRKKRIPYSKGQLRELEREYAANKFITKDKRRKISAATSLSERQITIWFQNRRVKEKKVLAKVKTSTTP
        ||||:||:|  ||:|||:||||||||||||||||||||||| ||:|||||||||||||||||||||:||:||||||||||||||||||:|:|| ||:
        GRKKRVPYTKVQLKELEREYATNKFITKDKRRISATTNLSERQVTIWFQNRRVKEKKVINKLKTT
HOX-A13  10        20        30        40        50        60
```

2. HOX-C13

AC   P31276 (Database accession number for HOX-C13)
DT   01-JUL-1993 (Date sequence created in database; no subsequent update or annotation)
DE   HOMEOBOX PROTEIN HOX-C13 (HOX-3G) (FRAGMENT)

SCORES    75.8% identity in 66 aa overlap

```
              190       200       210       220       230       240       250       260       270       280
rCIX-1  EQNPPGPFWKAAFAEPSVQHPPPDGCAFRRGRKKRIPYSKGQLRELEREYAANKFITKDKRRKISAATSLSERQITIWFQNRRVKEKKVLAKVKTSTTP
        ||||:||:|  ||:|||:||||||||||||||||||||||| ||:|||||||||||||||||||||:||:||||||||||||||||||:|:|| ||
        GRKKRVPYTKVQLKELEKEYAASKFITKEKRRRISATTNLSERQVTIWFQNRRVKEKKVVSKSKAP
HOX-C13  10        20        30        40        50        60
```

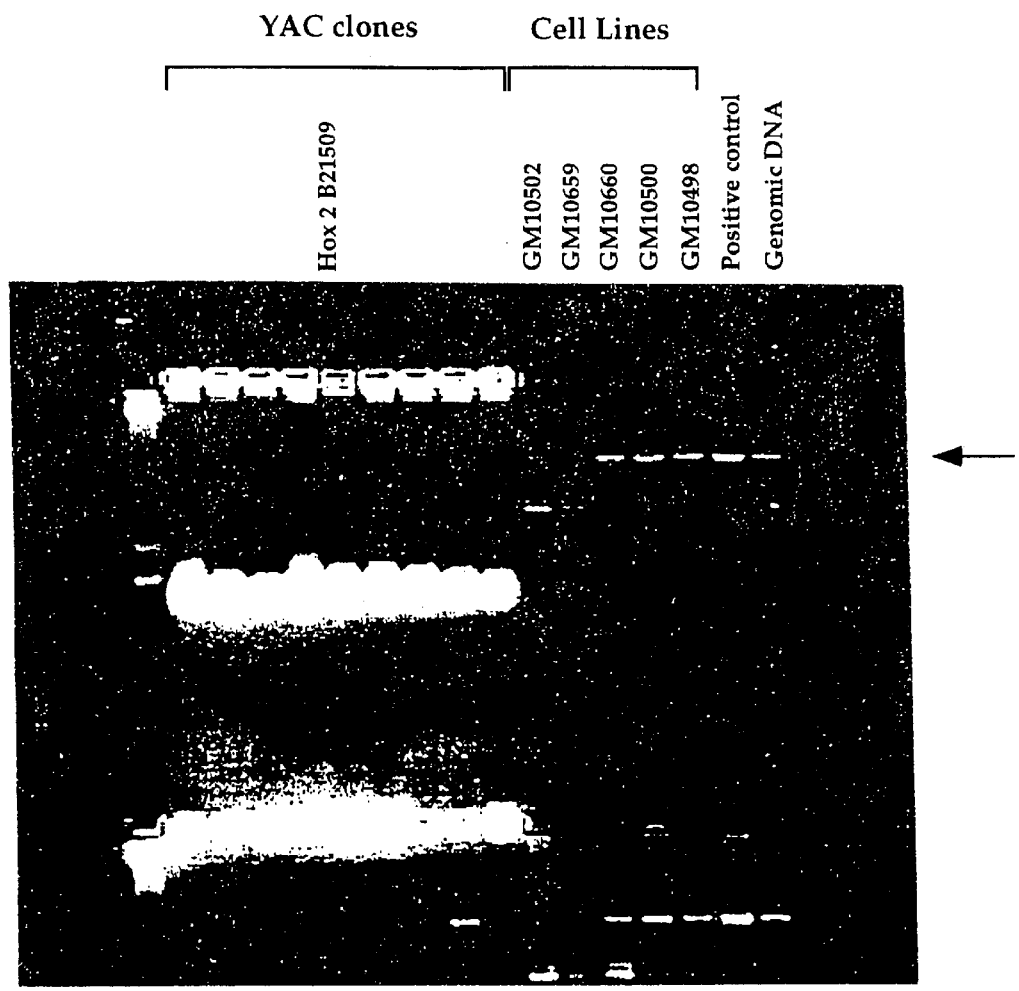
Figure 9. Localization of HoxB13 to chromosome 17q21 and the HoxB locus.

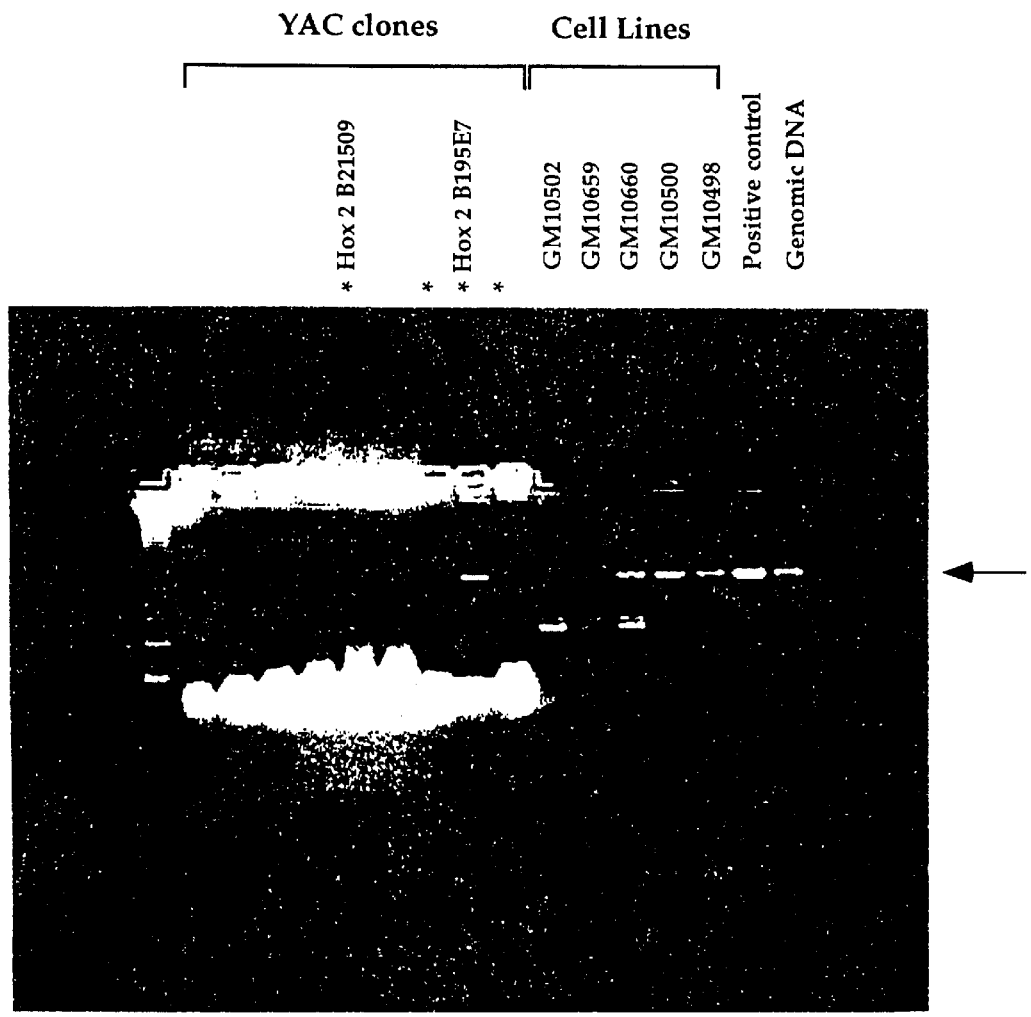
Figure 10. Localization of HoxB13 to chromosome 17q21 and the HoxB locus.

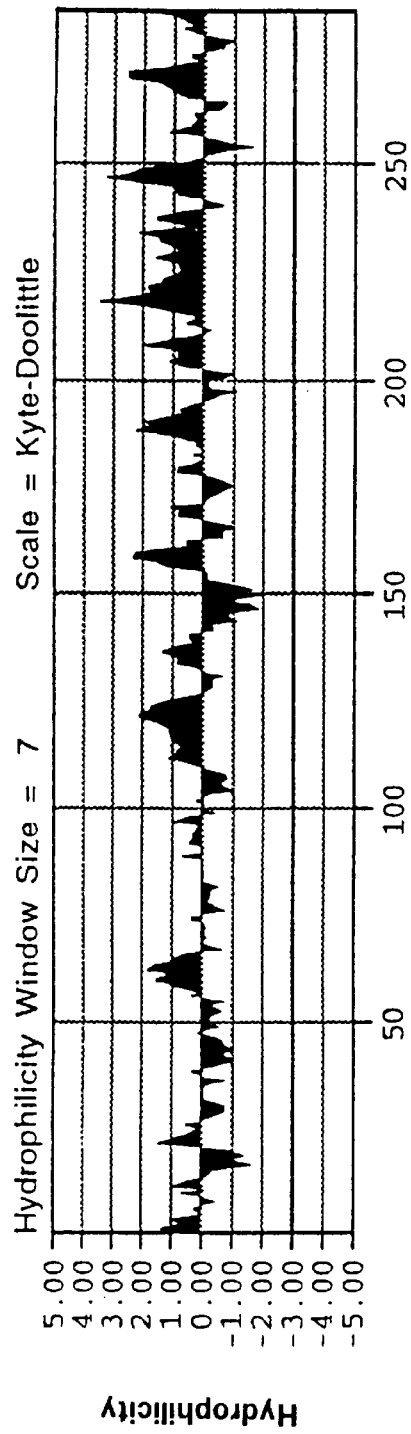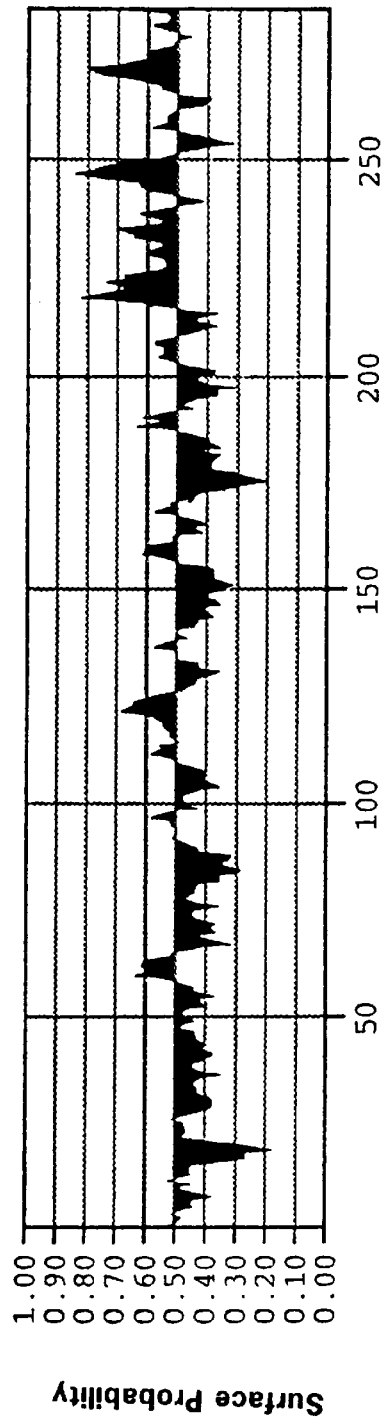

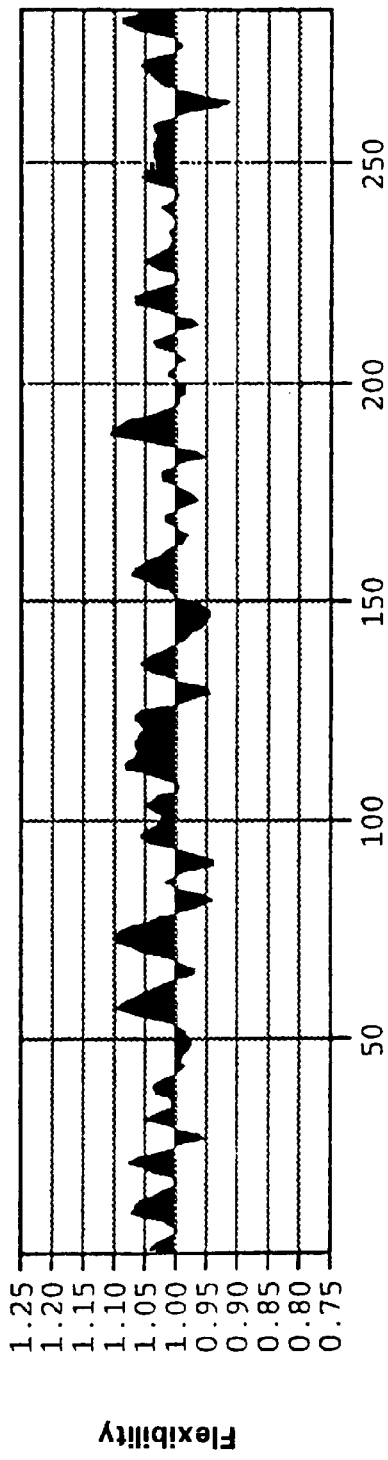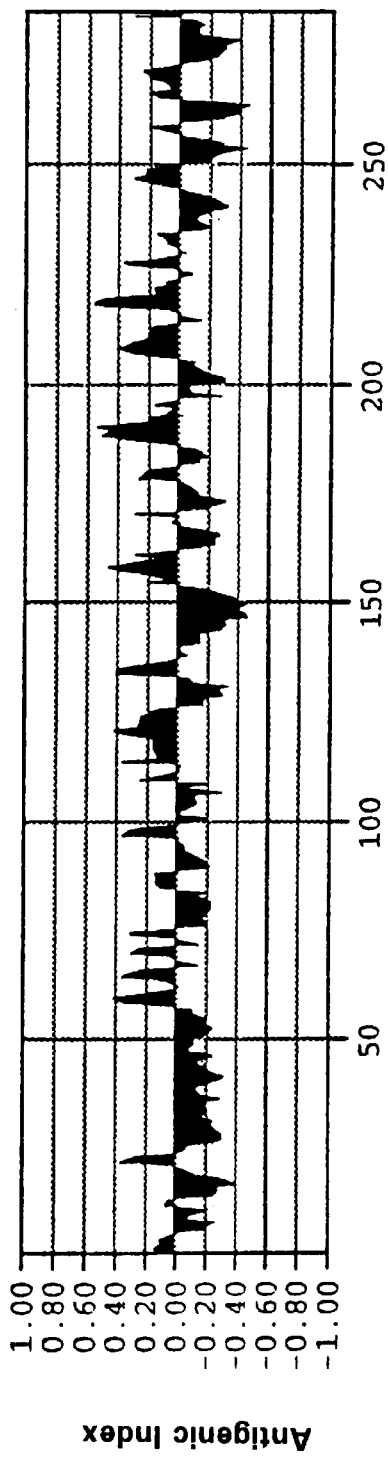
FIG. 13A-3
FIG. 13A-4

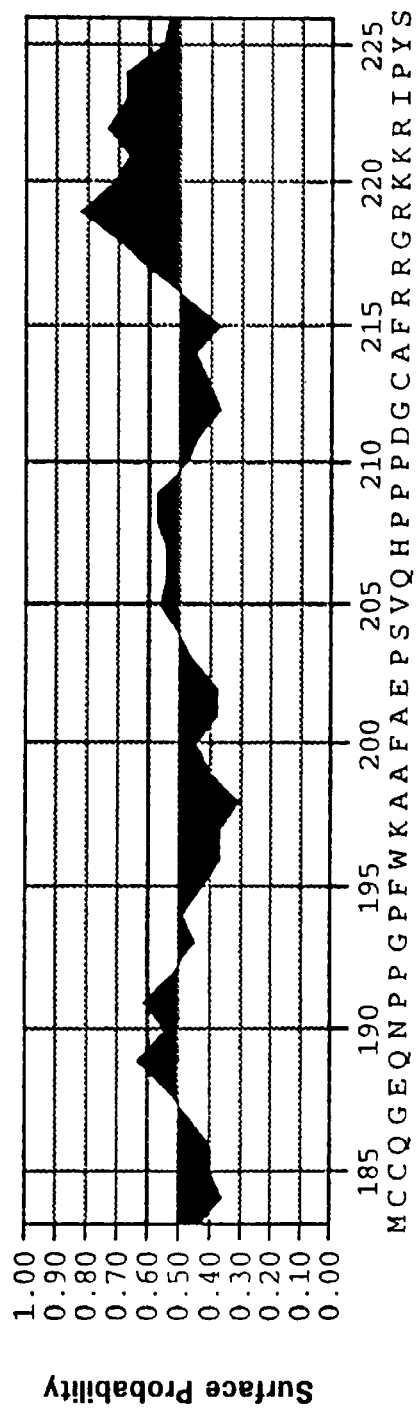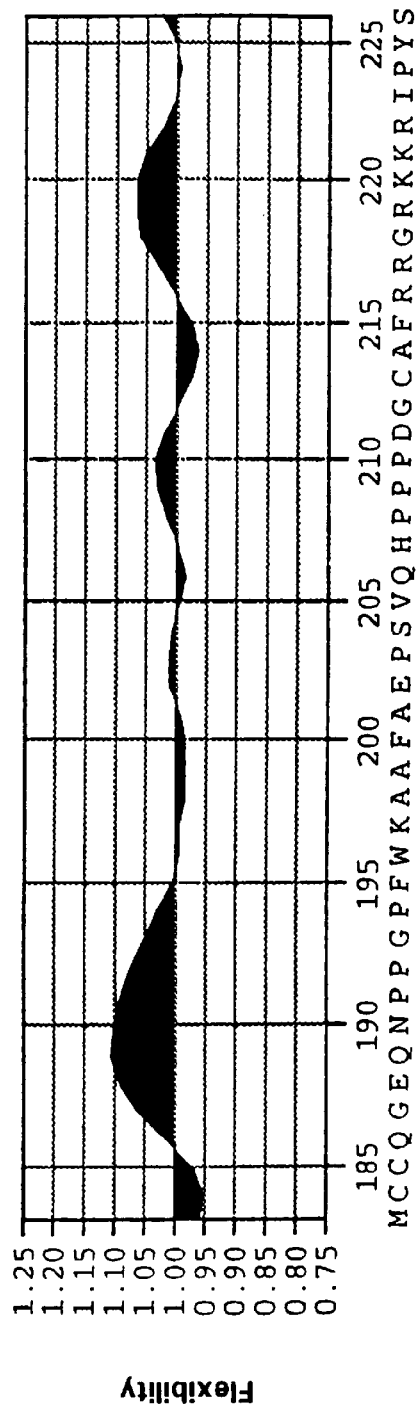

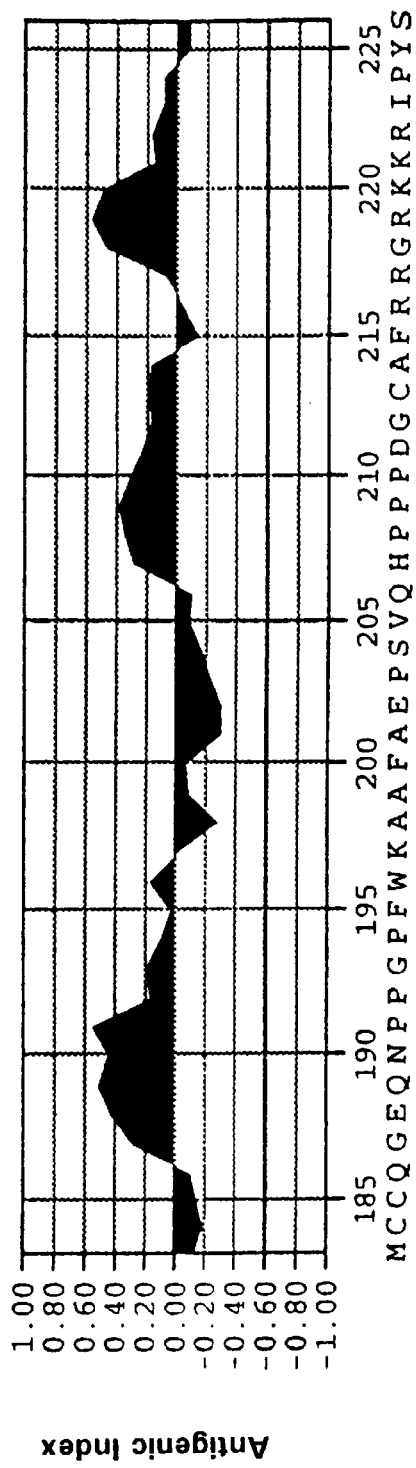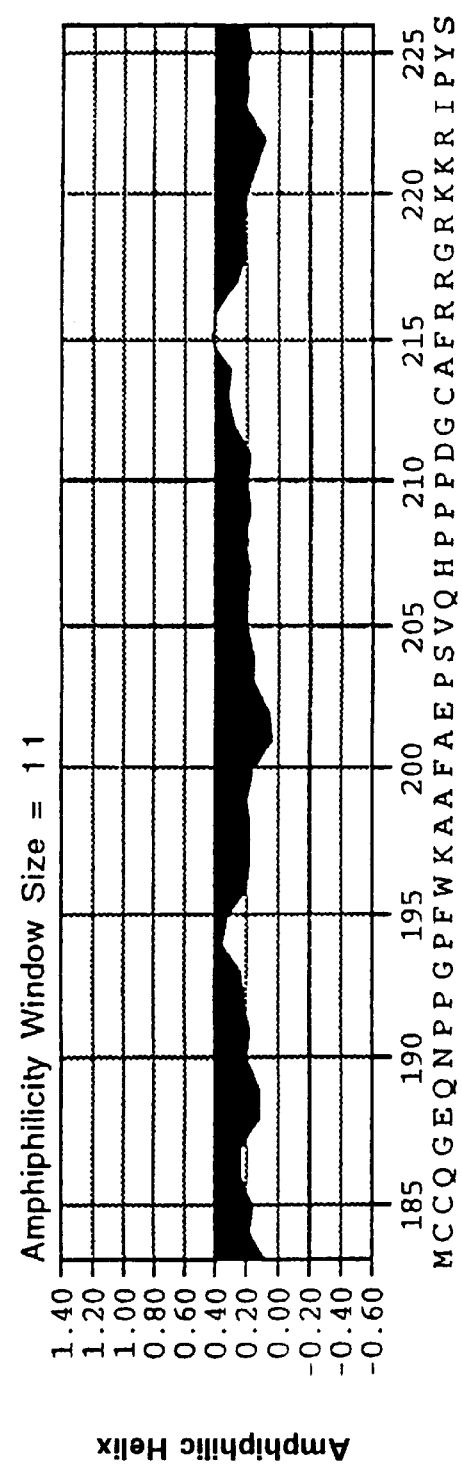

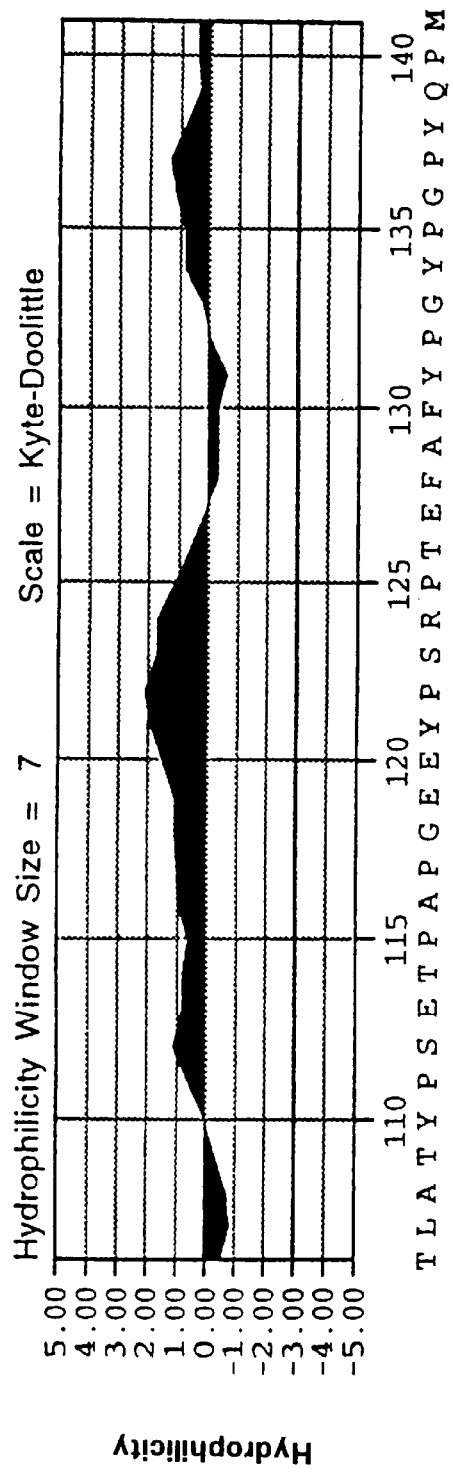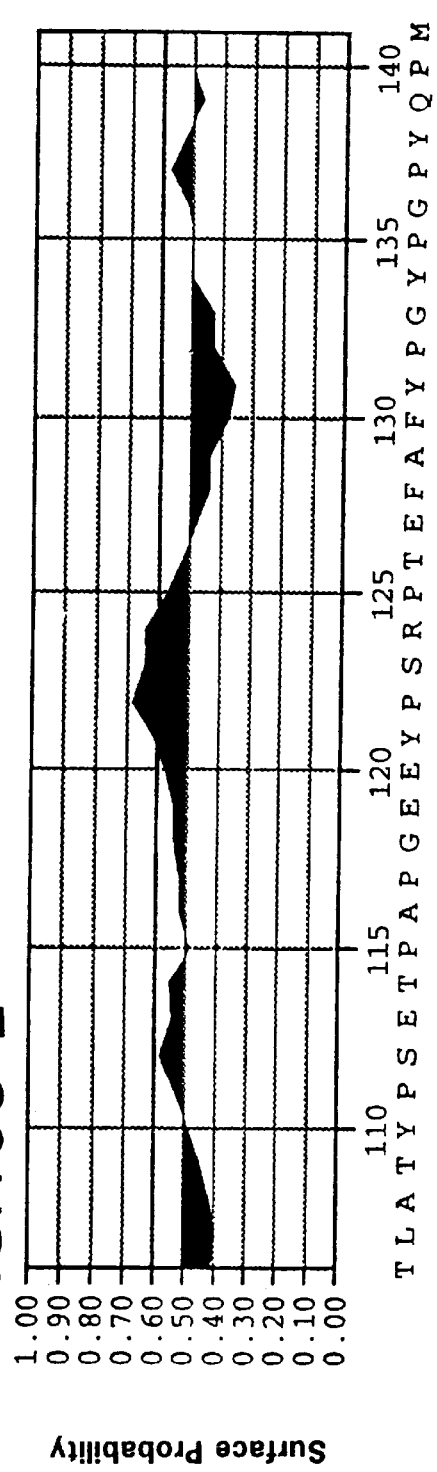

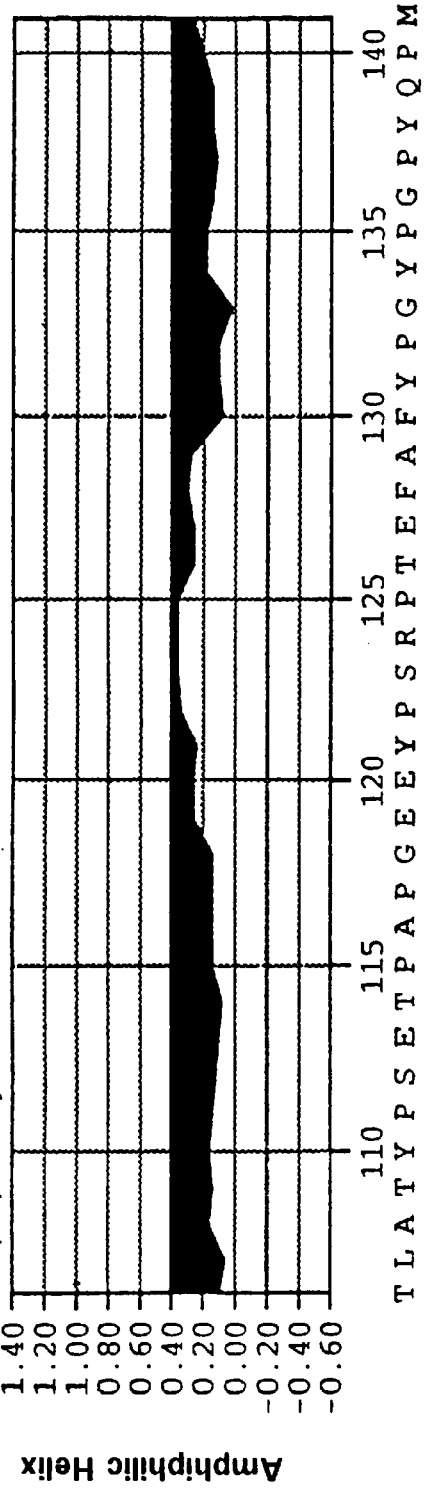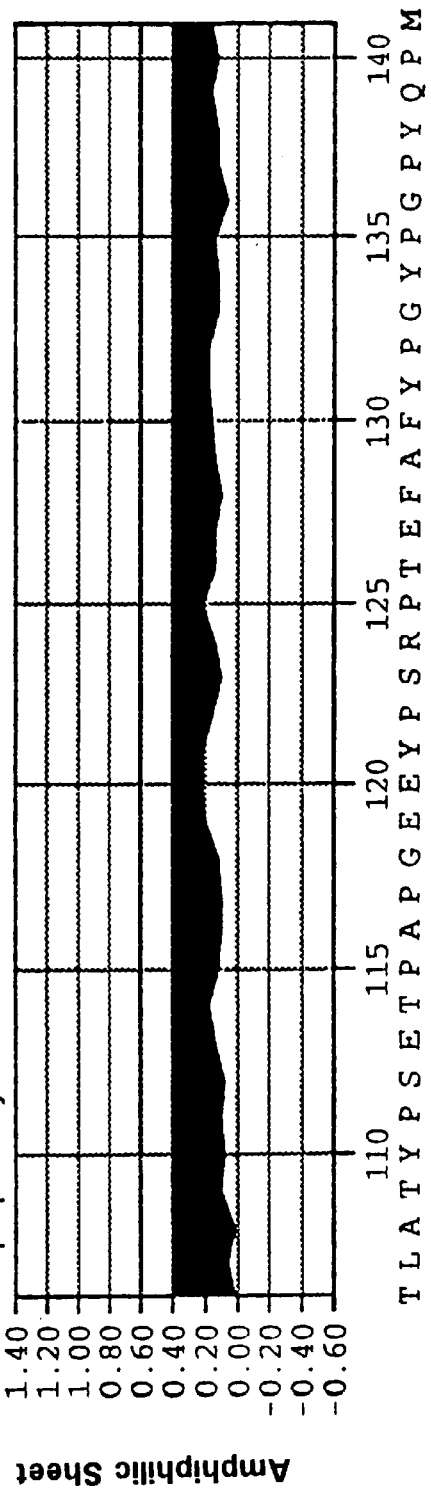

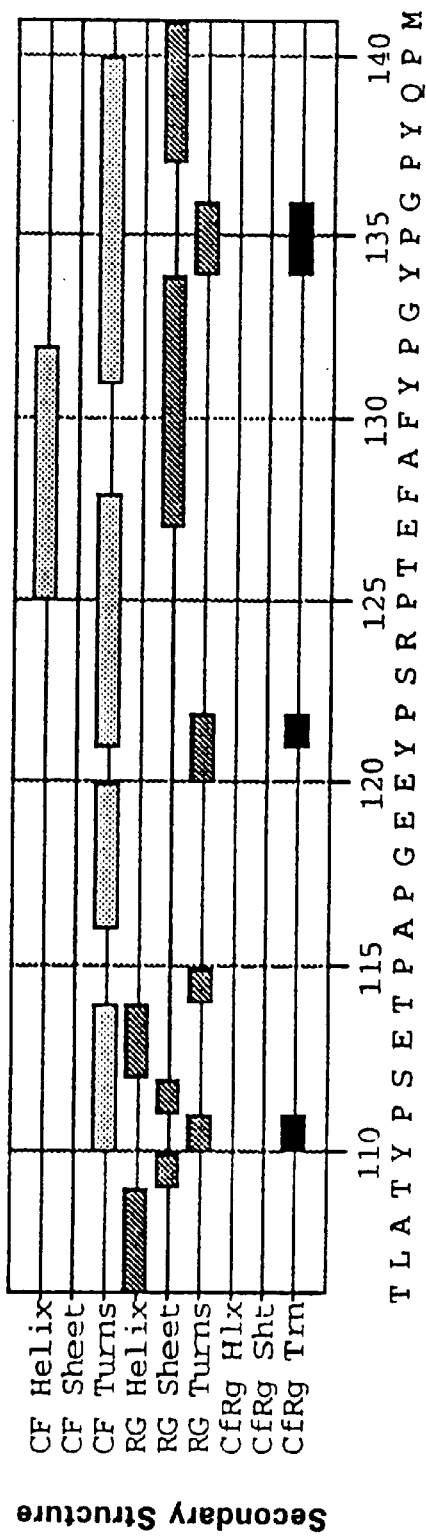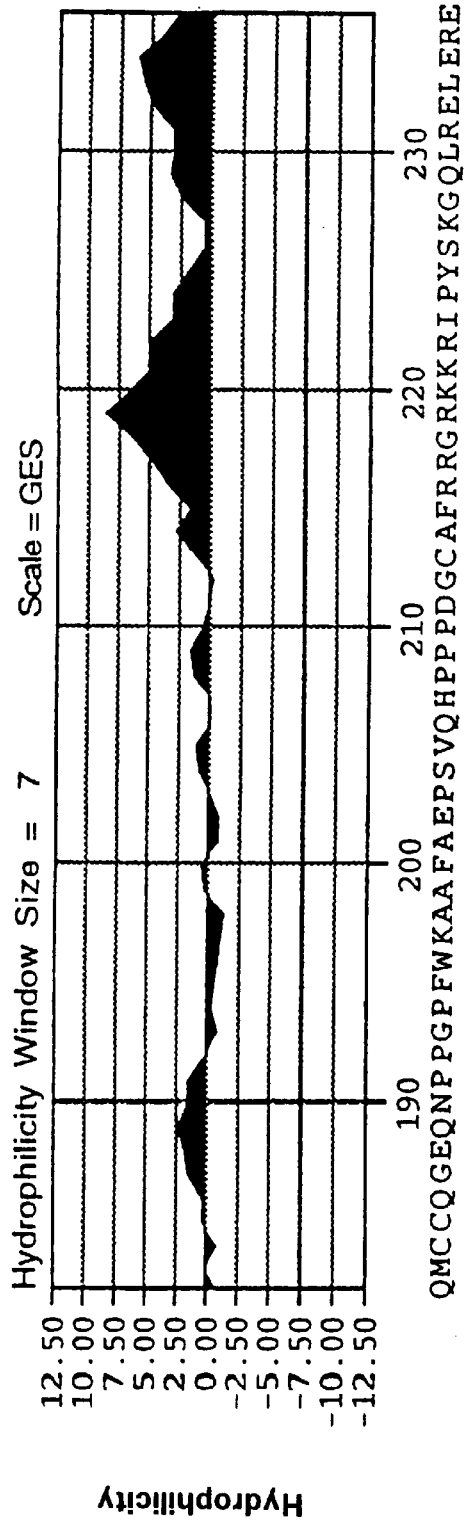

Surface Probability

Flexibility

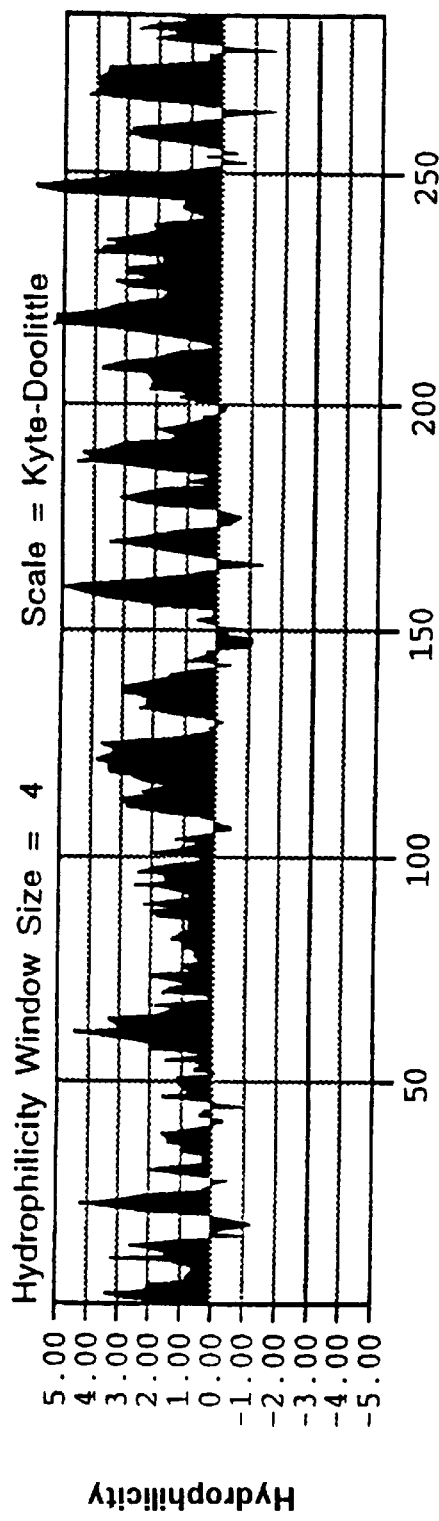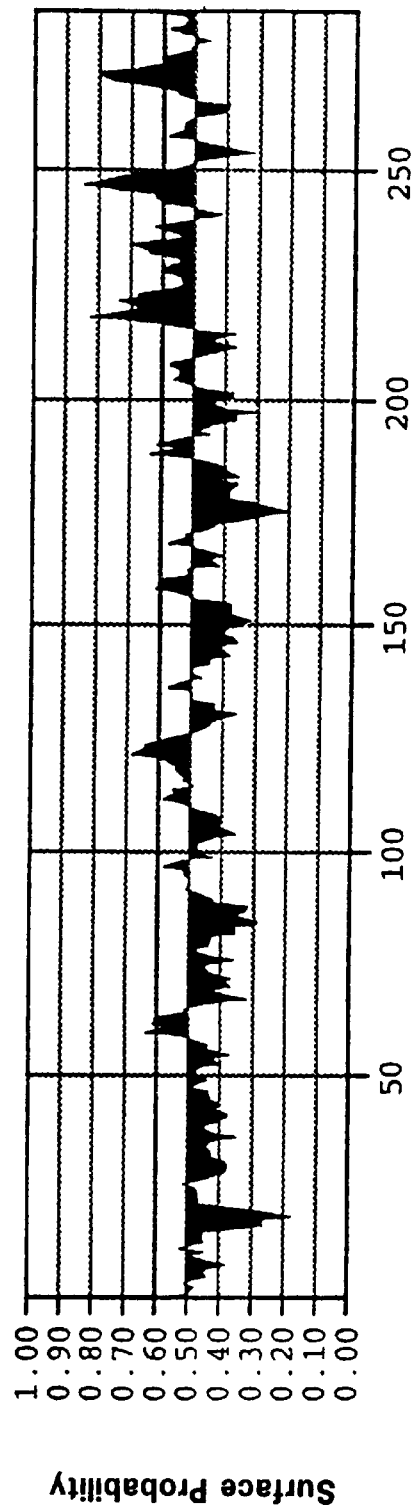

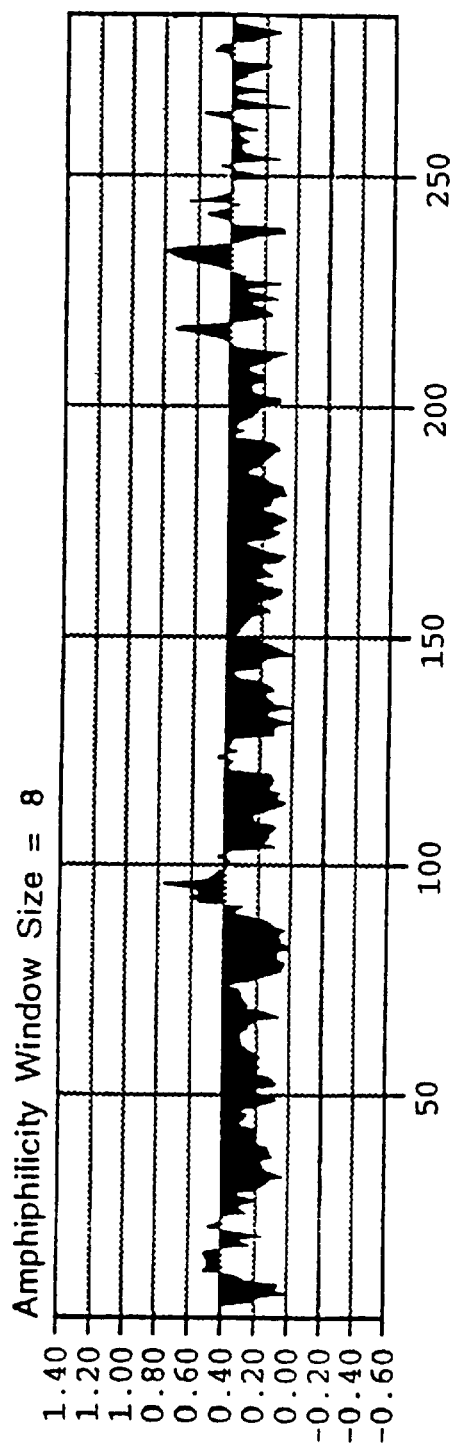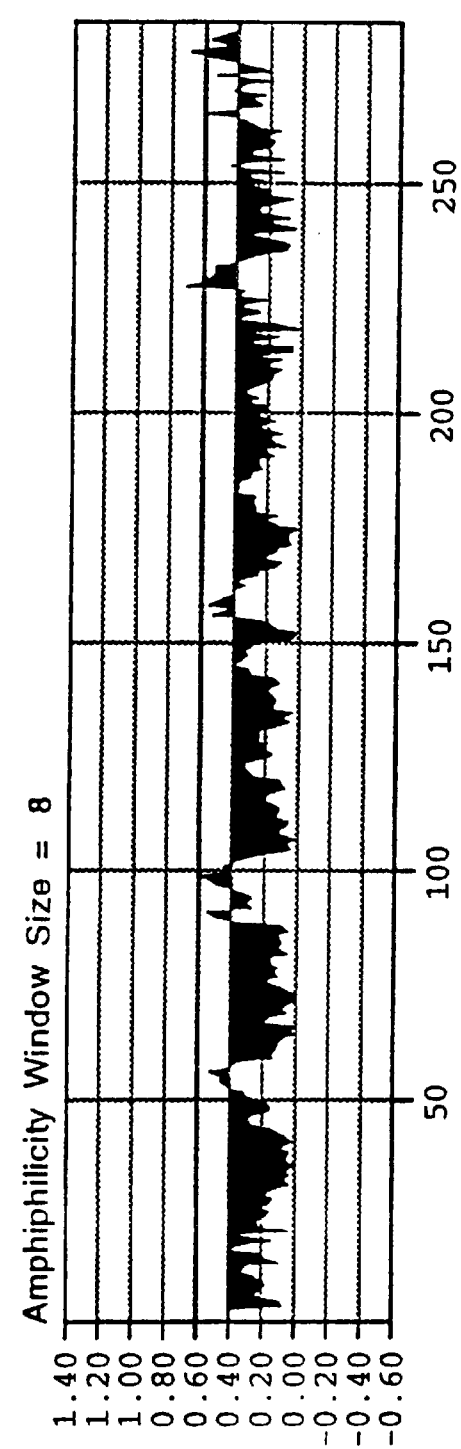

SEQUENCE LISTING (1) GENERAL INFORMATION:

(iii) NUMBER OF SEQUENCES: 49

(2) INFORMATION FOR SEQ ID NO:1:

(i) SEQUENCE CHARACTERISTICS:
      (A) LENGTH: 1379 base pairs
      (B) TYPE: nucleic acid
      (C) STRANDEDNESS: double
      (D) TOPOLOGY: linear (ii) MOLECULE TYPE: cDNA
      (A) DESCRIPTION: rat CIX-1 (Hoxb13) cDNA (iii) HYPOTHETICAL: NO (iv) ANTI-SENSE: NO (ix) FEATURE:
      (A) NAME/KEY: CDS
      (B) LOCATION: 64..927

(xi) SEQUENCE DESCRIPTION: SEQ ID NO:1:

```
TGAGAGAGCT TGCTGCCCCT AGAACCCCCA CCCTCGGCTC CCCATGAGCC GATCATTGGC          60

CCC ATG GAG CCC GGC AAT TAT GCC ACC TTG GAC GGG GCC AAG GAT ATC         108
    Met Glu Pro Gly Asn Tyr Ala Thr Leu Asp Gly Ala Lys Asp Ile
    1               5                  10                  15

GAA GGC TTG CTG GGA GCT GGA GGG GGT CGT CGG AAT TTA GTC GCC CAC         156
Glu Gly Leu Leu Gly Ala Gly Gly Gly Arg Arg Asn Leu Val Ala His
            20                  25                  30
```

| | | |
|---|---|---|
| TCC TCC CCA CTG GCT AGC CAT CCC GCA GCT CCA ACG CTG ATG CCG ACT<br>Ser Ser Pro Leu Ala Ser His Pro Ala Ala Pro Thr Leu Met Pro Thr<br>35 40 45 | | 204 |
| GTC AAC TAT GCC CCC TTG GAT CTG CCA GGC TCT GCA GAG CCA CCA AAG<br>Val Asn Tyr Ala Pro Leu Asp Leu Pro Gly Ser Ala Glu Pro Pro Lys<br>50 55 60 | | 252 |
| CAG TGC CAC CCT TGT CCT GGG GTG CCC CAG GGG GCA TCT CCA GCT CCT<br>Gln Cys His Pro Cys Pro Gly Val Pro Gln Gly Ala Ser Pro Ala Pro<br>65 70 75 | | 300 |
| GTG CCT TAT GGC TAC TTT GGA GGC GGG TAC TAC TCT TGC CGA GTA TCC<br>Val Pro Tyr Gly Tyr Phe Gly Gly Gly Tyr Tyr Ser Cys Arg Val Ser<br>80 85 90 95 | | 348 |
| AGG AGC TCA CTG AAA CCC TGT GCC CAG ACG GCC ACC CTG GCT ACT TAC<br>Arg Ser Ser Leu Lys Pro Cys Ala Gln Thr Ala Thr Leu Ala Thr Tyr<br>100 105 110 | | 396 |
| CCT TCG GAA ACC CCT GCA CCT GGG GAG GAG TAT CCT AGC CGT CCC ACC<br>Pro Ser Glu Thr Pro Ala Pro Gly Glu Glu Tyr Pro Ser Arg Pro Thr<br>115 120 125 | | 444 |
| GAG TTT GCC TTC TAT CCG GGC TAC CCG GGA CCT TAC CAG CCT ATG GCC<br>Glu Phe Ala Phe Tyr Pro Gly Tyr Pro Gly Pro Tyr Gln Pro Met Ala<br>130 135 140 | | 492 |
| AGT TAC CTG GAT GTG TCT GTG GTG CAG ACC CTG GGG GCC CCT GGG GAG<br>Ser Tyr Leu Asp Val Ser Val Val Gln Thr Leu Gly Ala Pro Gly Glu<br>145 150 155 | | 540 |
| CCT CGC CAC GAC TCT CTG CTT CCC GTG GAC AGT TAT CAG CCT TGG GCC<br>Pro Arg His Asp Ser Leu Leu Pro Val Asp Ser Tyr Gln Pro Trp Ala<br>160 165 170 175 | | 588 |
| CTG GCC GGT GGC TGG AAC AGC CAG ATG TGC TGC CAA GGT GAA CAG AAC<br>Leu Ala Gly Gly Trp Asn Ser Gln Met Cys Cys Gln Gly Glu Gln Asn<br>180 185 190 | | 636 |
| CCA CCA GGT CCA TTC TGG AAA GCA GCA TTT GCA GAG CCC AGT GTC CAG<br>Pro Pro Gly Pro Phe Trp Lys Ala Ala Phe Ala Glu Pro Ser Val Gln<br>195 200 205 | | 684 |
| CAC CCT CCT CCC GAC GGC TGC GCC TTC CGC CGC GGC CGC AAA AAA CGC<br>His Pro Pro Pro Asp Gly Cys Ala Phe Arg Arg Gly Arg Lys Lys Arg<br>210 215 220 | | 732 |
| ATT CCC TAT AGC AAG GGG CAG TTG CGA GAG CTG GAG CGA GAG TAT GCG<br>Ile Pro Tyr Ser Lys Gly Gln Leu Arg Glu Leu Glu Arg Glu Tyr Ala<br>225 230 235 | | 780 |
| GCC AAC AAG TTT ATC ACC AAG GAC AAG AGG CGC AAG ATC TCG GCA GCC<br>Ala Asn Lys Phe Ile Thr Lys Asp Lys Arg Arg Lys Ile Ser Ala Ala<br>240 245 250 255 | | 828 |
| ACC AGC CTC TCT GAA CGC CAG ATT ACC ATC TGG TTT CAG AAC CGC CGG<br>Thr Ser Leu Ser Glu Arg Gln Ile Thr Ile Trp Phe Gln Asn Arg Arg<br>260 265 270 | | 876 |
| GTC AAG GAG AAG AAG GTT CTT GCC AAG GTC AAG ACC AGC ACT ACT CCG<br>Val Lys Glu Lys Lys Val Leu Ala Lys Val Lys Thr Ser Thr Thr Pro<br>275 280 285 | | 924 |
| TGAGCACCAG TGGGGATGGG CAGGGGAAAG GGGCTTGGCC TGGAGAATTG GGAGCCCGCC | | 984 |
| AGGGCCAGGA CTGGCAGAGG ACTCGGCTGA GGGACCCCAA GAGATGACAC CTTTAGCAGG | | 1044 |
| CTACTGAGTT CTGGACTATT CCTCGGGGCT GTCCTGCATG TGCCAGAAGT GGGGGTCCGG | | 1104 |
| AAATCACAGT CCCCTTCATC GTGGTTCAGA AGAACCTGTA TCAGTCATAA TCATTCATCC | | 1164 |
| ATAACCAGTA CTAGTTGTCA TGATAATTAG CCTCATATTT TCTATCTAGA GCTCTGTTGA | | 1224 |
| GCGCTTAGAA ATCGCTTTCA TGAGTTGAGC TGATCGCGAA TAAATTTGGA ACCAAAGAGC | | 1284 |
| CACACCAACA AATCACCTTA TCTTTTATGC TCATTTCAAT TGCATTCTGA TTGCCTCAAA | | 1344 |
| TAAACTTATA CTCCGAAAAA GCAAACCCAT ATGAA | | 1379 |

(2) INFORMATION FOR SEQ ID NO:2:

(i) SEQUENCE CHARACTERISTICS:
        (A) LENGTH: 287 amino acids
        (B) TYPE: amino acid
        (D) TOPOLOGY: linear (ii) MOLECULE TYPE: protein
        (A) DESCRIPTION: rat CIX-1 (HoxB13) protein (xi) SEQUENCE DESCRIPTION: SEQ ID NO:2:

```
Met Glu Pro Gly Asn Tyr Ala Thr Leu Asp Gly Ala Lys Asp Ile Glu
 1               5                  10                  15

Gly Leu Leu Gly Ala Gly Gly Arg Arg Asn Leu Val Ala His Ser
                20                  25                  30

Ser Pro Leu Ala Ser His Pro Ala Ala Pro Thr Leu Met Pro Thr Val
                35                  40                  45

Asn Tyr Ala Pro Leu Asp Leu Pro Gly Ser Ala Glu Pro Pro Lys Gln
        50                  55                  60

Cys His Pro Cys Pro Gly Val Pro Gln Gly Ala Ser Pro Ala Pro Val
65                  70                  75                  80

Pro Tyr Gly Tyr Phe Gly Gly Gly Tyr Tyr Ser Cys Arg Val Ser Arg
                85                  90                  95

Ser Ser Leu Lys Pro Cys Ala Gln Thr Ala Thr Leu Ala Thr Tyr Pro
                100                 105                 110

Ser Glu Thr Pro Ala Pro Gly Glu Glu Tyr Pro Ser Arg Pro Thr Glu
                115                 120                 125

Phe Ala Phe Tyr Pro Gly Tyr Pro Gly Pro Tyr Gln Pro Met Ala Ser
        130                 135                 140

Tyr Leu Asp Val Ser Val Val Gln Thr Leu Gly Ala Pro Gly Glu Pro
145                 150                 155                 160

Arg His Asp Ser Leu Leu Pro Val Asp Ser Tyr Gln Pro Trp Ala Leu
                165                 170                 175

Ala Gly Gly Trp Asn Ser Gln Met Cys Cys Gln Gly Glu Gln Asn Pro
                180                 185                 190

Pro Gly Pro Phe Trp Lys Ala Ala Phe Ala Glu Pro Ser Val Gln His
                195                 200                 205

Pro Pro Pro Asp Gly Cys Ala Phe Arg Arg Gly Arg Lys Lys Arg Ile
        210                 215                 220

Pro Tyr Ser Lys Gly Gln Leu Arg Glu Leu Glu Arg Glu Tyr Ala Ala
225                 230                 235                 240

Asn Lys Phe Ile Thr Lys Asp Lys Arg Arg Lys Ile Ser Ala Ala Thr
                245                 250                 255

Ser Leu Ser Glu Arg Gln Ile Thr Ile Trp Phe Gln Asn Arg Arg Val
                260                 265                 270

Lys Glu Lys Lys Val Leu Ala Lys Val Lys Thr Ser Thr Thr Pro
                275                 280                 285
```

(2) INFORMATION FOR SEQ ID NO:3:

(i) SEQUENCE CHARACTERISTICS:
        (A) LENGTH: 2917 base pairs
        (B) TYPE: nucleic acid
        (C) STRANDEDNESS: double
        (D) TOPOLOGY: linear (ii) MOLECULE TYPE: DNA (genomic)
        (A) DESCRIPTION: Human HoxB13 gene (iii) HYPOTHETICAL: NO (iv) ANTI-SENSE: NO (ix) FEATURE:
    (A) NAME/KEY: CDS
    (B) LOCATION: 582..1184

(ix) FEATURE:
    (A) NAME/KEY: intron
    (B) LOCATION: 1185..2132

(ix) FEATURE:
    (A) NAME/KEY: CDS
    (B) LOCATION: 2133..2384

(xi) SEQUENCE DESCRIPTION: SEQ ID NO:3:

```
GAAAGCTAGG GAGGGAGAGG AGGAGAAGGA GGTGGGGCCC GGCTCCTCGT CCCCTCTTCC      60

TCCGCCCACC ACGCCTCCCC TCCCCCCGGA CGTGTAAATG AGACTCTGCA AACTGGAAAG     120

CAGCGAAAGA CACCTCCTTC CTTTTCTCTC TTGTTGTTTT TAAGTGGAAT GAGAGAGAGA     180

GGAGTGGAGA GGGCAAAGAA GAGAGAGAGG GAGAGAGAGA GAGGAGAGAA AGAGCGAGAG     240

AGCGAGAGAG AGACAGAGAG ACAGAGAGAG AGAGAGAGAG AGAGAGAGAG AGAGAGAGAA     300

AGAGAGAGAG AGAGAGAGAG AATAAGCTGG GGTAAAGTAT TTTCGCAGTT TCTGCCTTTA     360

GGATTTTATT AGCTTCTCTC CCCCAGGCCG CAGCCAATCA GCGCGCGTGC CCGGGCCCCT     420

GCGTCTCTTG CGTCAAGACG GCCGTGCTGA GCGAATGCAG GCGACTTGCG AGCTGGGAGC     480

GATTTAAAAC GCTTTGGATT CCCCCGGCCT GGGTGGGGAG AGCGAGCTGG GTGCCCCCTA     540
```

| GATTCCCCGC CCCCGCACCT CATGAGCCGA CCCTCGGCTC C | ATG GAG CCC GGC | 593 |
|---|---|---|
| | Met Glu Pro Gly | |
| | 1 | |

| AAT TAT GCC ACC TTG GAT GGA GCC AAG GAT ATC GAA GGC TTG CTG GGA | 641 |
|---|---|
| Asn Tyr Ala Thr Leu Asp Gly Ala Lys Asp Ile Glu Gly Leu Leu Gly | |
| 5               10               15               20 | |

| GCG GGA GGG GGG CGG AAT CTG GTC GCC CAC TCC CCT CTG ACC AGC CAC | 689 |
|---|---|
| Ala Gly Gly Gly Arg Asn Leu Val Ala His Ser Pro Leu Thr Ser His | |
| 25               30               35 | |

| CCA GCG GCG CCT ACG CTG ATG CCT GCT GTC AAC TAT GCC CCC TTG GAT | 737 |
|---|---|
| Pro Ala Ala Pro Thr Leu Met Pro Ala Val Asn Tyr Ala Pro Leu Asp | |
| 40               45               50 | |

| CTG CCA GGC TCG GCG GAG CCG CCA AAG CAA TGC CAC CCA TGC CCT GGG | 785 |
|---|---|
| Leu Pro Gly Ser Ala Glu Pro Pro Lys Gln Cys His Pro Cys Pro Gly | |
| 55               60               65 | |

| GTG CGC CAG GGG ACG TCC CCA GCT CCC GTG CCT TAT GGT TAC TTT GGA | 833 |
|---|---|
| Val Arg Gln Gly Thr Ser Pro Ala Pro Val Pro Tyr Gly Tyr Phe Gly | |
| 70               75               80 | |

| GGC GCG TAC TAC TCC TGC CGA GTG TCC CGG AGC TCG CTG AAA CCC TGT | 881 |
|---|---|
| Gly Ala Tyr Tyr Ser Cys Arg Val Ser Arg Ser Ser Leu Lys Pro Cys | |
| 85               90               95              100 | |

| GCC CAG GCA GCC ACC CTG GCC GCG TAC CCC GCG GAG ACT CCC ACG GCC | 929 |
|---|---|
| Ala Gln Ala Ala Thr Leu Ala Ala Tyr Pro Ala Glu Thr Pro Thr Ala | |
| 105              110             115 | |

| GGG GAA GAG TAC CCC AGC CGC CCC ACT GAG TTT GCC TTC TAT CCG GGA | 977 |
|---|---|
| Gly Glu Glu Tyr Pro Ser Arg Pro Thr Glu Phe Ala Phe Tyr Pro Gly | |
| 120              125             130 | |

| TAT CCG GGA ACC TAC CAG CCT ATG GCC AGT TAC CTG GAC GTG TCT GTG | 1025 |
|---|---|
| Tyr Pro Gly Thr Tyr Gln Pro Met Ala Ser Tyr Leu Asp Val Ser Val | |
| 135              140             145 | |

| GTG CAG ACT CTG GGT GCT CCT GGA GAA CCG CGA CAT GAC TCC CTG TTG | 1073 |
|---|---|
| Val Gln Thr Leu Gly Ala Pro Gly Glu Pro Arg His Asp Ser Leu Leu | |
| 150              155             160 | |

| CCT GTG GAC AGT TAC CAG TCT TGG GCT CTC GCT GGT GGC TGG AAC AGC | 1121 |

```
Pro Val Asp Ser Tyr Gln Ser Trp Ala Leu Ala Gly Gly Trp Asn Ser
165                 170                 175                 180

CAG ATG TGT TGC CAG GGA GAA CAG AAC CCA CCA GGT CCC TTT TGG AAG       1169
Gln Met Cys Cys Gln Gly Glu Gln Asn Pro Pro Gly Pro Phe Trp Lys
            185                 190                 195

GCA GCA TTT GCA G  GT ACCTCTATTA CCCTGGGTCC CCTGGGCTCT GAGCCTGGGG     1224
Ala Ala Phe Ala Asp
            200

TTGTGGGTCC CAATGGCATT TCCCTGGGAG GAGGAGGAGG GAGACTTGGA GCTGGTGAGG     1284

ATGAGCTTGG TGCTCCTCCC TTGGTTATTA GGACTCTGAA GGAGGTCTGA GTAGCTGGAG     1344

GGCCTGGATG GAGGTCAGTG TGAGGGGCCT GAGCTGGGTG CTATCTGAAG CCTGAAGGCC     1404

ACCTCACTTC TCCAGGAGGC CCTGGGACCA GCCTTTCAAC ATGTCTGAGA GGTTTAGTCT     1464

CTTTGCTGTT GAGTGGGGAT CAGGGTGTCC CTACCCAGCA CAATTCCAAA CTAATTCTAC     1524

ACAAAAGCTA AATAACTCTC AATTCGGTGC GTGGGGAGTG GGTGTGGGAG ATGGGTAAAA     1584

AGGTATTGGA TGTACTGTAG AGAATACAAC CTCTCACTTT CTATTAGATG AGTTTTCCAA     1644

TTTCCAAAGA AAAATTTAGG TTTCCTGCAG CCGTGACATA TGTGTGTGCA CTGGGATGGG     1704

TTAATGTGTG TGTGTGTGTG TGTATGCGCA TGTATTGGGA GTGGGGCAG AAACGTGTTT      1764

CCAGAATTTG CCTGTAGAAT CTAAAAGAGT GGCCAAGAGT CTGGAAATGC ATGAAGACTG     1824

GACGTATGTG ATGGTGGGCA AAGGCCTGAC TGTGTGTGGT GTGTGGGTAT GTTTGCAGAT     1884

TCGCGGGTGT GAGAGCAGTG ATGGGTGAGG GTGGCCTTCA GGAGCCAAGG CTGAGCGGTG     1944

GTGAGAGAAC AAGCCGGAAG CCAGGGTGCT GTCCTGGTAT GCTTTGGAGG AACAGGAGTT     2004

GCACGTGCCC TGTAGGGTGA CCTGTGTGCA CCTGTGAGAT GACTTAGCTT GGGGCTTGCA     2064

AGGCCTGGGT CTGCATGGGT GGGTATCTGA CCATGCCTTT TCCTCCCTCC CTTTCACGCC     2124

GCGCAG AC TCC AGC GGG CAG CAC CCT CCT GAC GCC TGC GCC TTT CGT CGC    2174
        Ser Ser Gly Gln His Pro Pro Asp Ala Cys Ala Phe Arg Arg
        202     205                 210                 215

GGC CGC AAG AAA CGC ATT CCG TAC AGC AAG GGG CAG TTG CGG GAG CTG       2222
Gly Arg Lys Lys Arg Ile Pro Tyr Ser Lys Gly Gln Leu Arg Glu Leu
            220                 225                 230

GAG CGG GAG TAT GCG GCT AAC AAG TTC ATC ACC AAG GAC AAG AGG CGC       2270
Glu Arg Glu Tyr Ala Ala Asn Lys Phe Ile Thr Lys Asp Lys Arg Arg
            235                 240                 245

AAG ATC TCG GCA GCC ACC AGC CTC TCG GAG CGC CAG ATT ACC ATC TGG       2318
Lys Ile Ser Ala Ala Thr Ser Leu Ser Glu Arg Gln Ile Thr Ile Trp
            250                 255                 260

TTT CAG AAC CGC CGG GTC AAA GAG AAG AAG GTT CTC GCC AAG GTG AAG       2366
Phe Gln Asn Arg Arg Val Lys Glu Lys Lys Val Leu Ala Lys Val Lys
            265                 270                 275

AAC AGC GCT ACC CCT TAAGAGATCT CCTTGCCTGG GTGGGAGGAG CGAAAGTGGG       2421
Asn Ser Ala Thr Pro
280

GGTGTCCTGG GGAGACCAGG AACCTGCCAA GCCCAGGCTG GGCCAAGGA CTCTGCTGAG      2481

AGGCCCCTAG AGACAACACC CTTCCCAGGC CACTGGCTGC TGGACTGTTC CTCAGGAGCG     2541

GCCTGGGTAC CCAGTATGTG CAGGGAGACG GAACCCCATG TGACAGCCCA CTCCACCAGG     2601

GTTCCCAAAG AACCTGGCCC AGTCATAATC ATTCATCCTG ACAGTGGCAA TAATCACGAT     2661

AACCAGTACT AGCTGCCATG ATCGTTAGCC TCATATTTTC TATCTAGAGC TCTGTAGAGC     2721

ACTTTAGAAA CCGCTTTCAT GAATTGAGCT AATTATGAAT AAATTTGGAA GGCGATCCCT     2781

TTGCAGGGAA GCTTTCTCTC AGACCCCCTT CCATTACACC TCTCACCCTG GTAACAGCAG     2841
```

-continued

GAAGACTGAG GAGAGGGGAA CGGGCAGATT CGTTGTGTGG CTGTGATGTC CGTTTAGCAT    2901

TTTTCTCAGC TGACAG                                                   2917

(2) INFORMATION FOR SEQ ID NO:4:

(i) SEQUENCE CHARACTERISTICS:
        (A) LENGTH: 1380 base pairs
        (B) TYPE: nucleic acid
        (C) STRANDEDNESS: double
        (D) TOPOLOGY: linear (ii) MOLECULE TYPE: cDNA
        (A) DESCRIPTION: HoxB13 cDNA (iii) HYPOTHETICAL: NO (iv) ANTI-SENSE: NO (ix) FEATURE:
        (A) NAME/KEY: CDS
        (B) LOCATION: 65..928

(xi) SEQUENCE DESCRIPTION: SEQ ID NO:4:

TGAGAGAGCT TGCTGNCCCC TAGAACCCCC ACCCTCGGCT CCCCATGAGC CGATCATTGG      60

CCCCATGGAG CCCGGCAATT ATGCCACCTT GGACGGGGCC AAGGATATCG AAGGCTTGCT     120

GGGAGCTGGA GGGGGTCGTC GGAATTTAGT CGCCCACTCC TCCCCACTGG CTAGCCATCC     180

CGCAGCTCCA ACGCTGATGC CGACTGTCAA CTATGCCCCC TTGGATCTGC CAGGCTCTGC     240

AGAGCCACCA AAGCAGTGCC ACCCTTGTCC TGGGGTGCCC CAGGGGGCAT CTCCAGCTCC     300

TGTGCCTTAT GGCTACTTTG GAGGCGGGTA CTACTCTTGC CGAGTATCCA GGAGCTCACT     360

GAAACCCTGT GCCCAGACGG CCACCCTGGC TACTTACCCT TCGGAAACCC CTGCACCTGG     420

GGAGGAGTAT CCTAGCCGTC CCACCGAGTT TGCCTTCTAT CCGGGCTACC CGGGACCTTA     480

CCAGCCTATG GCCAGTTACC TGGATGTGTC TGTGGTGCAG ACCCTGGGGG CCCCTGGGGA     540

GCCTCGCCAC GACTCTCTGC TTCCCGTGGA CAGTTATCAG CCTTGGGCCC TGGCCGGTGG     600

CTGGAACAGC CAGATGTGCT GCCAAGGTGA ACAGAACCCA CCAGGTCCAT TCTGGAAAGC     660

AGCATTTGCA GAGCCCAGTG TCCAGCACCC TCCTCCCGAC GGCTGCGCCT TCCGCCGCGG     720

CCGCAAAAAA CGCATTCCCT ATAGCAAGGG GCAGTTGCGA GAGCTGGAGC GAGAGTATGC     780

GGCCAACAAG TTTATCACCA AGGACAAGAG GCGCAAGATC TCGGCAGCCA CCAGCCTCTC     840

TGAACGCCAG ATTACCATCT GGTTTCAGAA CCGCCGCGTC AAGGAGAAGA AGGTTCTTGC     900

CAAGGTCAAG ACCAGCACTA CTCCGTGAGC ACCAGTGGGA TGGGCAGGG GAAAGGGGCT     960

TGGCCTGGAG AATTGGGAGC CGCCAGGGC CAGGACTGGC AGAGGACTCG GCTGAGGGAC    1020

CCCAAGAGAT GACACCTTTA GCAGGCTACT GAGTTCTGGA CTATTCCTCG GGGCTGTCCT    1080

GCATGTGCCA GAAGTGGGGG TCCGGAAATC ACAGTCCCCT TCATCGTGGT TCAGAAGAAC    1140

CTGTATCAGT CATAATCATT CATCCATAAC CAGTACTAGT TGTCATGATA ATTAGCCTCA    1200

TATTTTCTAT CTAGAGCTCT GTTGAGCGCT TAGAAATCGC TTTCATGAGT TGAGCTGATC    1260

GCGAATAAAT TTGGAACCAA AGAGCCACAC CAACAAATCA CCTTATCTTT TATGCTCATT    1320

TCAATTGCAT TCTGATTGCC TCAAATAAAC TTATACTCCG AAAAAGCAAA CCCATATGAA    1380

(2) INFORMATION FOR SEQ ID NO:5:

(i) SEQUENCE CHARACTERISTICS:
        (A) LENGTH: 284 amino acids
        (B) TYPE: amino acid
        (D) TOPOLOGY: linear (ii) MOLECULE TYPE: protein
        (A) DESCRIPTION: Human HoxB13 protein (xi) SEQUENCE DESCRIPTION: SEQ ID NO:5:

Met Glu Pro Gly Asn Tyr Ala Thr Leu Asp Gly Ala Lys Asp Ile Glu
 1               5                  10                  15

Gly Leu Leu Gly Ala Gly Gly Arg Asn Leu Val Ala His Ser Pro
            20                  25                  30

Leu Thr Ser His Pro Ala Ala Pro Thr Leu Met Pro Ala Val Asn Tyr
        35                  40                  45

Ala Pro Leu Asp Leu Pro Gly Ser Ala Glu Pro Lys Gln Cys His
    50                  55                  60

Pro Cys Pro Gly Val Arg Gln Gly Thr Ser Pro Ala Pro Val Pro Tyr
65                  70                  75                  80

Gly Tyr Phe Gly Gly Ala Tyr Tyr Ser Cys Arg Val Ser Arg Ser Ser
                85                  90                  95

Leu Lys Pro Cys Ala Gln Ala Ala Thr Leu Ala Ala Tyr Pro Ala Glu
                100                 105                 110

Thr Pro Thr Ala Gly Glu Glu Tyr Pro Ser Arg Pro Thr Glu Phe Ala
                115                 120                 125

Phe Tyr Pro Gly Tyr Pro Gly Thr Tyr Gln Pro Met Ala Ser Tyr Leu
130                 135                 140

Asp Val Ser Val Val Gln Thr Leu Gly Ala Pro Gly Glu Pro Arg His
145                 150                 155                 160

Asp Ser Leu Leu Pro Val Asp Ser Tyr Gln Ser Trp Ala Leu Ala Gly
                165                 170                 175

Gly Trp Asn Ser Gln Met Cys Cys Gln Gly Glu Gln Asn Pro Pro Gly
                180                 185                 190

Pro Phe Trp Lys Ala Ala Phe Ala Gly Ser Ser Gly Gln His Pro Pro
        195                 200                 205

Asp Ala Cys Ala Phe Arg Arg Gly Arg Lys Lys Arg Ile Pro Tyr Ser
210                 215                 220

Lys Gly Gln Leu Arg Glu Leu Glu Arg Glu Tyr Ala Ala Asn Lys Phe
225                 230                 235                 240

Ile Thr Lys Asp Lys Arg Arg Lys Ile Ser Ala Ala Thr Ser Leu Ser
                245                 250                 255

Glu Arg Gln Ile Thr Ile Trp Phe Gln Asn Arg Arg Val Lys Glu Lys
                260                 265                 270

Lys Val Leu Ala Lys Val Lys Asn Ser Ala Thr Pro
            275                 280

(2) INFORMATION FOR SEQ ID NO:6:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (primer)
        (A) DESCRIPTION: GCIX-1

(iii) HYPOTHETICAL: NO (iv) ANTI-SENSE: NO (xi) SEQUENCE DESCRIPTION: SEQ ID NO:6:

GCGACATGAC TCCCTGT                                                17

(2) INFORMATION FOR SEQ ID NO:7:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (primer)
        (A) DESCRIPTION: GCIX-2

(iii) HYPOTHETICAL: NO (iv) ANTI-SENSE: NO (xi) SEQUENCE DESCRIPTION: SEQ ID NO:7:

AGACTGGTAA CTGTCC                                          16

(2) INFORMATION FOR SEQ ID NO:8:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (primer)
        (A) DESCRIPTION: GCIX-3

(iii) HYPOTHETICAL: NO (iv) ANTI-SENSE: NO (xi) SEQUENCE DESCRIPTION: SEQ ID NO:8:

TTAACGACGT TGGGTATG                                       18

(2) INFORMATION FOR SEQ ID NO:9:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (primer)
        (A) DESCRIPTION: GCIX-4

(iii) HYPOTHETICAL: NO (iv) ANTI-SENSE: NO (xi) SEQUENCE DESCRIPTION: SEQ ID NO:9:

CCTATGTACA GGAAATAG                                       18

(2) INFORMATION FOR SEQ ID NO:10:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (primer)
        (A) DESCRIPTION: GCIX-5

(iii) HYPOTHETICAL: NO (iv) ANTI-SENSE: NO (xi) SEQUENCE DESCRIPTION: SEQ ID NO:10:

GTTGACAGCA GGCATCAG                                       18

```
(2) INFORMATION FOR SEQ ID NO:11:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (primer)
        (A) DESCRIPTION: CIXSOME-1

(iii) HYPOTHETICAL: NO (iv) ANTI-SENSE: NO (xi) SEQUENCE DESCRIPTION: SEQ ID NO:11:

GGTACCTGCA AATGCTGCCT TCCA                                              24

(2) INFORMATION FOR SEQ ID NO:12:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (primer)
        (A) DESCRIPTION: CIXSOME-2

(iii) HYPOTHETICAL: NO (iv) ANTI-SENSE: NO (xi) SEQUENCE DESCRIPTION: SEQ ID NO:12:

TGGGGAGAGC GAGCTGAGTG C                                                 21

(2) INFORMATION FOR SEQ ID NO:13:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (primer)
        (A) DESCRIPTION: HGCIX-6

(iii) HYPOTHETICAL: NO (iv) ANTI-SENSE: NO (xi) SEQUENCE DESCRIPTION: SEQ ID NO:13:

GGGGAATCCA AAGCGTT                                                      17

(2) INFORMATION FOR SEQ ID NO:14:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (primer)
        (A) DESCRIPTION: HGCIX-7

(iii) HYPOTHETICAL: NO (iv) ANTI-SENSE: NO (xi) SEQUENCE DESCRIPTION: SEQ ID NO:14:

AAACGCTTTG GATTCCC                                                      17
```

(2) INFORMATION FOR SEQ ID NO:15:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (primer)
        (A) DESCRIPTION: HGCIX-8

(iii) HYPOTHETICAL: NO (iv) ANTI-SENSE: NO (xi) SEQUENCE DESCRIPTION: SEQ ID NO:15:

AGAAGGTTCT CGCCAAG            17

(2) INFORMATION FOR SEQ ID NO:16:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (primer)
        (A) DESCRIPTION: HGCIX-9

(iii) HYPOTHETICAL: NO (iv) ANTI-SENSE: NO (xi) SEQUENCE DESCRIPTION: SEQ ID NO:16:

TCTGAAACCA GATGGTA            17

(2) INFORMATION FOR SEQ ID NO:17:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (primer)
        (A) DESCRIPTION: HGCIX-10

(iii) HYPOTHETICAL: NO (iv) ANTI-SENSE: NO (xi) SEQUENCE DESCRIPTION: SEQ ID NO:17:

GGGTAAAGTA TTTTCGC            17

(2) INFORMATION FOR SEQ ID NO:18:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (primer)
        (A) DESCRIPTION: HGCIX-11

(iii) HYPOTHETICAL: NO (iv) ANTI-SENSE: NO (xi) SEQUENCE DESCRIPTION: SEQ ID NO:18:

AGGTGCACAC AGGTCAC            17

(2) INFORMATION FOR SEQ ID NO:19:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (primer)
        (A) DESCRIPTION: HGCIX-12

(iii) HYPOTHETICAL: NO (iv) ANTI-SENSE: NO (xi) SEQUENCE DESCRIPTION: SEQ ID NO:19:

AAGGAGGTCT GAGTAGC         17

(2) INFORMATION FOR SEQ ID NO:20:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (primer)
        (A) DESCRIPTION: HGCIX-13

(iii) HYPOTHETICAL: NO (iv) ANTI-SENSE: NO (xi) SEQUENCE DESCRIPTION: SEQ ID NO:20:

CTGATGCCTG CTGTCAAC         18

(2) INFORMATION FOR SEQ ID NO:21:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (primer)
        (A) DESCRIPTION: HGCIX-14

(iii) HYPOTHETICAL: NO (iv) ANTI-SENSE: NO (xi) SEQUENCE DESCRIPTION: SEQ ID NO:21:

GATATCCCGG ATAGAAGG         18

(2) INFORMATION FOR SEQ ID NO:22:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (primer)
        (A) DESCRIPTION: HGCIX-15

(iii) HYPOTHETICAL: NO (iv) ANTI-SENSE: NO (xi) SEQUENCE DESCRIPTION: SEQ ID NO:22:

CCTTCTATCC GGGATATC         18

(2) INFORMATION FOR SEQ ID NO:23:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (primer)
        (A) DESCRIPTION: HGCIX-16

(iii) HYPOTHETICAL: NO (iv) ANTI-SENSE: NO (xi) SEQUENCE DESCRIPTION: SEQ ID NO:23:

CATATGTCAC GGCTGCAG                                  18

(2) INFORMATION FOR SEQ ID NO:24:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (primer)
        (A) DESCRIPTION: HGCIX-17

(iii) HYPOTHETICAL: NO (iv) ANTI-SENSE: NO (xi) SEQUENCE DESCRIPTION: SEQ ID NO:24:

CTGCAGCCGT GACATATG                                  18

(2) INFORMATION FOR SEQ ID NO:25:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (primer)
        (A) DESCRIPTION: HGCIX-18

(iii) HYPOTHETICAL: NO (iv) ANTI-SENSE: NO (xi) SEQUENCE DESCRIPTION: SEQ ID NO:25:

CCAGTTTGCA GAGTCTCA                                  18

(2) INFORMATION FOR SEQ ID NO:26:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (primer)
        (A) DESCRIPTION: HGCIX-19

(iii) HYPOTHETICAL: NO (iv) ANTI-SENSE: NO (xi) SEQUENCE DESCRIPTION: SEQ ID NO:26:

CATCTGGTTT CAGAACCG                                  18

(2) INFORMATION FOR SEQ ID NO:27:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (primer)
        (A) DESCRIPTION: ISL3-5

(iii) HYPOTHETICAL: NO (iv) ANTI-SENSE: NO (xi) SEQUENCE DESCRIPTION: SEQ ID NO:27:

CGAGTATCCA GGAGCTCACT G                                 21

(2) INFORMATION FOR SEQ ID NO:28:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (primer)
        (A) DESCRIPTION: ISL3-A (iii) HYPOTHETICAL: NO (iv) ANTI-SENSE: NO (xi) SEQUENCE DESCRIPTION: SEQ ID NO:28:

GGTCTTGACC TTGGCAAGAA C                                 21

(2) INFORMATION FOR SEQ ID NO:29:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (primer)
        (A) DESCRIPTION: ISL3-22

(iii) HYPOTHETICAL: NO (iv) ANTI-SENSE: NO (xi) SEQUENCE DESCRIPTION: SEQ ID NO:29:

GGATATCGAA GGCTTGCA                                     18

(2) INFORMATION FOR SEQ ID NO:30:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (primer)
        (A) DESCRIPTION: ISL3-21

(iii) HYPOTHETICAL: NO (iv) ANTI-SENSE: NO (xi) SEQUENCE DESCRIPTION: SEQ ID NO:30:

TAAGTAGCCA GGGTGGCC                                     18

(2) INFORMATION FOR SEQ ID NO:31:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (primer)
        (A) DESCRIPTION: GST-GGGS (iii) HYPOTHETICAL: NO (iv) ANTI-SENSE: NO (xi) SEQUENCE DESCRIPTION: SEQ ID NO:31:

GCCGGATCCG AGGCGGGTAC TACTCTTGC                                29

(2) INFORMATION FOR SEQ ID NO:32:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (primer)
        (A) DESCRIPTION: GST-FRRA (iii) HYPOTHETICAL: NO (iv) ANTI-SENSE: NO (xi) SEQUENCE DESCRIPTION: SEQ ID NO:32:

GCCGGATCCT CAGCGGCGGA AGGCGCAGCC                               30

(2) INFORMATION FOR SEQ ID NO:33:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (primer)
        (A) DESCRIPTION: GAL/ISL3-1

(iii) HYPOTHETICAL: NO (iv) ANTI-SENSE: NO (xi) SEQUENCE DESCRIPTION: SEQ ID NO:33:

GGCGGATCCA TGGAGCCCGG CAAT                                     24

(2) INFORMATION FOR SEQ ID NO:34:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (primer)
        (A) DESCRIPTION: GST/ISL3-2

(iii) HYPOTHETICAL: NO (iv) ANTI-SENSE: NO (xi) SEQUENCE DESCRIPTION: SEQ ID NO:34:

GGCGGATCCA TGCCGACTGT CAAC                                     24

(2) INFORMATION FOR SEQ ID NO:35:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (primer)
        (A) DESCRIPTION: GST/ISL3-3

(iii) HYPOTHETICAL: NO (iv) ANTI-SENSE: NO (xi) SEQUENCE DESCRIPTION: SEQ ID NO:35:

GGCGGATCCA TGGCTCCTGT GCCTTATGGC          30

(2) INFORMATION FOR SEQ ID NO:36:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (primer)
        (A) DESCRIPTION: GST/ISL3-4

(iii) HYPOTHETICAL: NO (iv) ANTI-SENSE: NO (xi) SEQUENCE DESCRIPTION: SEQ ID NO:36:

GGCGGATCCA TGTCGGAAAC CCCTGCACCT          30

(2) INFORMATION FOR SEQ ID NO:37:

(i) SEQUENCE CHARACTERISTICS:
        (A) LENGTH: 5 amino acids
        (B) TYPE: amino acid
        (D) TOPOLOGY: linear (ii) MOLECULE TYPE: protein
        (A) DESCRIPTION: amino acids 16-20 of the homeobox homeodomain (vi) ORIGINAL SOURCE:
        (A) ORGANISM: Rat (xi) SEQUENCE DESCRIPTION: SEQ ID NO:37:

Leu Glu Lys Glu Phe
1            5

(2) INFORMATION FOR SEQ ID NO:38:

(i) SEQUENCE CHARACTERISTICS:
        (A) LENGTH: 5 amino acids
        (B) TYPE: amino acid
        (D) TOPOLOGY: linear (ii) MOLECULE TYPE: protein
        (A) DESCRIPTION: amino acids 47-51 of the homeobox homeodomain (vi) ORIGINAL SOURCE:
        (A) ORGANISM: Rat (xi) SEQUENCE DESCRIPTION: SEQ ID NO:38:

Ile Trp Phe Gln Asn
1            5

(2) INFORMATION FOR SEQ ID NO:39:

(i) SEQUENCE CHARACTERISTICS:
    (A) LENGTH: 26 base pairs
    (B) TYPE: nucleic acid
    (C) STRANDEDNESS: single
    (D) TOPOLOGY: linear (ii) MOLECULE TYPE: DNA (primer)
    (A) DESCRIPTION: GST/ISL1

(iii) HYPOTHETICAL: NO (iv) ANTI-SENSE: NO (xi) SEQUENCE DESCRIPTION: SEQ ID NO:39:

GGCGGATCCC CATGGAGCCC GGCAAT                                    26

(2) INFORMATION FOR SEQ ID NO:40:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (primer)
        (A) DESCRIPTION: GST/ISL2

(iii) HYPOTHETICAL: NO (iv) ANTI-SENSE: NO (xi) SEQUENCE DESCRIPTION: SEQ ID NO:40:

GCCGGATCCT CACGGAGTAG TGCT                                      24

(2) INFORMATION FOR SEQ ID NO:41:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (primer)
        (A) DESCRIPTION: FLAT-S (iii) HYPOTHETICAL: NO (iv) ANTI-SENSE: NO (xi) SEQUENCE DESCRIPTION: SEQ ID NO:41:

GATCCCCTTG TTAATAATCT AATTACCCTA GG                             32

(2) INFORMATION FOR SEQ ID NO:42:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (primer)
        (A) DESCRIPTION: FLAT-A (iii) HYPOTHETICAL: NO (iv) ANTI-SENSE: NO (xi) SEQUENCE DESCRIPTION: SEQ ID NO:42:

GATCCCTAGG GTAATTAGAT TATTAACAAG GG                             32

(2) INFORMATION FOR SEQ ID NO:43:

(i) SEQUENCE CHARACTERISTICS:
        (A) LENGTH: 99 amino acids
        (B) TYPE: amino acid
        (C) STRANDEDNESS: single
        (D) TOPOLOGY: linear (ii) MOLECULE TYPE: peptide
        (A) DESCRIPTION: Amino acids 189-287 of rat CIX-1 (HoxB13)
            protein (iii) HYPOTHETICAL: NO (v) FRAGMENT TYPE: C-terminal (xi) SEQUENCE DESCRIPTION: SEQ ID NO:43:

Glu Gln Asn Pro Pro Gly Pro Phe Trp Lys Ala Ala Phe Ala Glu Pro
1               5                  10                  15

Ser Val Gln His Pro Pro Asp Gly Cys Ala Phe Arg Arg Gly Arg
            20                  25                  30

Lys Lys Arg Ile Pro Tyr Ser Lys Gly Gln Leu Arg Glu Leu Glu Arg
            35                  40                  45

Glu Tyr Ala Ala Asn Lys Phe Ile Thr Lys Asp Lys Arg Arg Lys Ile
        50                  55                  60

Ser Ala Ala Thr Ser Leu Ser Glu Arg Gln Ile Thr Ile Trp Phe Gln
65                  70                  75                  80

Asn Arg Arg Val Lys Glu Lys Lys Val Leu Ala Lys Val Lys Thr Ser
                85                  90                  95

Thr Thr Pro (2) INFORMATION FOR SEQ ID NO:44:

(i) SEQUENCE CHARACTERISTICS:
        (A) LENGTH: 66 amino acids
        (B) TYPE: amino acid
        (C) STRANDEDNESS: single
        (D) TOPOLOGY: linear (ii) MOLECULE TYPE: peptide
        (A) DESCRIPTION: portion of human HoxA13 sequence (v) FRAGMENT TYPE: internal (vi) ORIGINAL SOURCE:
        (A) ORGANISM: Homo sapiens (xi) SEQUENCE DESCRIPTION: SEQ ID NO:44:

Gly Arg Lys Lys Arg Val Pro Tyr Thr Lys Val Gln Leu Lys Glu Leu
1               5                  10                  15

Glu Arg Glu Tyr Ala Thr Asn Lys Phe Ile Thr Lys Asp Lys Arg Arg
            20                  25                  30

Arg Ile Ser Ala Thr Thr Asn Leu Ser Glu Arg Gln Val Thr Ile Trp
        35                  40                  45

Phe Gln Asn Arg Arg Val Lys Glu Lys Lys Val Ile Asn Lys Leu Lys
    50                  55                  60

Thr Thr
65

(2) INFORMATION FOR SEQ ID NO:45:

(i) SEQUENCE CHARACTERISTICS:
        (A) LENGTH: 66 amino acids
        (B) TYPE: amino acid
        (C) STRANDEDNESS: single
        (D) TOPOLOGY: linear (ii) MOLECULE TYPE: peptide (A) DESCRIPTION: portion of human HoxC13 sequence (v) FRAGMENT TYPE: internal (vi) ORIGINAL SOURCE:
    (A) ORGANISM: Homo sapiens (xi) SEQUENCE DESCRIPTION: SEQ ID NO:45:

```
Gly Arg Lys Lys Arg Val Pro Tyr Thr Lys Val Gln Leu Lys Glu Leu
1               5                   10                  15

Glu Lys Glu Tyr Ala Ala Ser Lys Phe Ile Thr Lys Glu Lys Arg Arg
            20                  25                  30

Arg Ile Ser Ala Thr Thr Asn Leu Ser Glu Arg Gln Val Thr Ile Trp
        35                  40                  45

Phe Gln Asn Arg Arg Val Lys Glu Lys Lys Val Ser Lys Ser Lys
    50                  55                  60

Ala Pro
65
```

(2) INFORMATION FOR SEQ ID NO:46:

(i) SEQUENCE CHARACTERISTICS:
        (A) LENGTH: 68 amino acids
        (B) TYPE: amino acid
        (C) STRANDEDNESS: single
        (D) TOPOLOGY: linear (ii) MOLECULE TYPE: peptide
        (A) DESCRIPTION: portion of chick HoxD13 sequence (v) FRAGMENT TYPE: internal (vi) ORIGINAL SOURCE:
        (A) ORGANISM: Homo sapiens (xi) SEQUENCE DESCRIPTION: SEQ ID NO:46:

```
Gly Arg Lys Lys Arg Val Pro Tyr Thr Lys Leu Gln Leu Lys Glu Leu
1               5                   10                  15

Glu Asn Glu Tyr Ala Ile Asn Lys Phe Ile Asn Lys Asp Lys Arg Arg
            20                  25                  30

Arg Ile Ser Ala Ala Thr Asn Leu Ser Glu Arg Gln Val Thr Ile Trp
        35                  40                  45

Phe Gln Asn Arg Arg Val Lys Asp Lys Lys Ile Val Ser Lys Leu Lys
    50                  55                  60

Asp Asn Val Ser
65
```

(2) INFORMATION FOR SEQ ID NO:47:

(i) SEQUENCE CHARACTERISTICS:
        (A) LENGTH: 44 amino acids
        (B) TYPE: amino acid
        (C) STRANDEDNESS: single
        (D) TOPOLOGY: linear (ii) MOLECULE TYPE: Peptide
        (A) DESCRIPTION: rat CIX-1

(vi) ORIGINAL SOURCE:
        (A) ORGANISM: Rat (xi) SEQUENCE DESCRIPTION: SEQ ID NO:47:

```
Met Cys Cys Gln Gly Glu Gln Asn Pro Pro Gly Pro Phe Trp Lys Ala
1               5                   10                  15

Ala Phe Ala Glu Pro Ser Val Gln His Pro Pro Pro Asp Gly Cys Ala
            20                  25                  30
```

```
Phe Arg Arg Gly Arg Lys Lys Arg Ile Pro Tyr Ser
        35                  40
```

(2) INFORMATION FOR SEQ ID NO:48:

(i) SEQUENCE CHARACTERISTICS:
        (A) LENGTH: 36 amino acids
        (B) TYPE: amino acid
        (C) STRANDEDNESS: single
        (D) TOPOLOGY: linear (ii) MOLECULE TYPE: peptide
        (A) DESCRIPTION: rat CIX-1

(vi) ORIGINAL SOURCE:
        (A) ORGANISM: Rat (iii) HYPOTHETICAL: NO (v) FRAGMENT TYPE: internal (xi) SEQUENCE DESCRIPTION: SEQ ID NO:48:

```
Thr Leu Ala Thr Tyr Pro Ser Glu Thr Pro Ala Pro Gly Glu Glu Tyr
1               5                   10                  15

Pro Ser Arg Pro Thr Glu Phe Ala Phe Tyr Pro Gly Tyr Pro Gly Pro
            20                  25                  30

Tyr Gln Pro Met
        35
```

(2) INFORMATION FOR SEQ ID NO:49:

(i) SEQUENCE CHARACTERISTICS:
        (A) LENGTH: 55 amino acids
        (B) TYPE: amino acid
        (C) STRANDEDNESS: single
        (D) TOPOLOGY: linear (ii) MOLECULE TYPE: Peptide
        (A) DESCRIPTION: rat CIX-1

(vi) ORIGINAL SOURCE:
        (A) ORGANISM: Rat (iii) HYPOTHETICAL: NO (v) FRAGMENT TYPE: internal (xi) SEQUENCE DESCRIPTION: SEQ ID NO:49:

```
Gln Met Cys Cys Gln Gly Glu Gln Asn Pro Pro Gly Pro Phe Trp Lys
1               5                   10                  15

Ala Ala Phe Ala Glu Pro Ser Val Gln His Pro Pro Asp Gly Cys
            20                  25                  30

Ala Phe Arg Arg Gly Arg Lys Lys Arg Ile Pro Tyr Ser Lys Gly Gln
        35                  40                  45

Leu Arg Glu Leu Glu Arg Glu
    50                  55
```

ISLET-SPECIFIC HOMEOPROTEIN AND TRANSCRIPTIONAL REGULATOR OF INSULIN GENE EXPRESSION, HOXB13

CROSS-REFERENCE TO RELATED APPLICATIONS

This application is related to U.S. patent application Ser. No. 08/106,936, filed Aug. 16, 1993, the contents of which are hereby incorporated herein by reference in their entirety.

TECHNICAL FIELD OF THE INVENTION

The present invention relates generally to homeoprotein regulators of insulin gene expression. In particular, the invention relates to a homeotic selector gene which controls insulin gene expression in a calcium-sensitive manner.

BACKGROUND OF THE INVENTION

Glucose homeostasis requires the concerted efforts of numerous neuroendocrine systems. Pancreatic islets, however, are considered to be the primary "glucose sensor" in mammals. Islets contain four populations of cells which are characterized primarily by their production of insulin, glucagon, somatostatin or pancreatic polypeptide. Among these, insulin-producing β-cells predominate. Insulin secretion and production are stimulated by increases in serum glucose, an event which is mandatory for subsequent glucose uptake in certain tissues. Hence, dysfunction or destruction of β-cells results in elevated serum glucose levels, ultimately developing into diabetes.

Genetic linkage analysis indicates that hereditary factors strongly influence susceptibility to acquisition of the diabetic state. For example, at least 18 genetic loci have some degree of linkage to insulin-dependent diabetes mellitus (IDDM). One disease susceptibility locus, termed IDDM2, encompasses the human insulin gene and is associated with altered transcriptional regulation of insulin promoter function. Hence, disruption of the processes that regulate insulin gene expression may account in part for diabetogenesis. Consistent with this hypothesis, impaired β-cell function is a very common feature of diabetes.

Non-insulin dependent diabetes mellitus (NIDDM) is thought to occur as a result of both external and complex genetic influences. Interestingly, allelic variants at the insulin locus itself have been associated with the disease. These variants appear to contain a normal insulin gene, but exhibit altered properties with regard to transcriptional regulation.

Estimates indicate that as many as 20 million Americans may suffer from Type II diabetes. The progression of the disease appears to require both environmental factors and certain as yet largely unidentified diabetes susceptibility genes, which may contribute to the peripheral insulin resistance of type II diabetics, in which tissues fail to utilize glucose appropriately in response to the insulin signal. Alternatively, genetic factors may account for the reduced glucose sensitivity of the insulin-producing pancreatic β-cells in these individuals. The end result of both of these physiological states is the marked hyperglycemia which constitutes the primary hallmark of diabetes.

Transcriptional control of the insulin gene is achieved through a short region of flanking DNA that interacts with cell-specific and glucose-sensitive signalling molecules. The precise nature of this regulatory organization remains poorly understood, although it is generally acknowledged that basic helix-loop-helix (bHLH) and homeodomain-containing factors are critical components of the transcriptional machinery that governs β-cell-specific expression of insulin. An islet-specific bHLH complex interacts with a proximal E-box that has been variously termed Nir, IEB1 or ICE; this element is present twice in the rat insulin I gene, but only once in the rat insulin II and human insulin genes.

Transient assays in insulin-producing cell lines suggest that E-box-binding factors synergize with β-cell-specific proteins that bind a nearby AT-rich sequence termed FLAT, which bears the hallmarks of a homeodomain recognition sequence. Indeed, several characterized homeodomain proteins have been shown to bind the FLAT element, including Isl-1, lmx-1, cdx-3 and STF-1. In addition, the latter of these corresponds to the principal binding activity at an evolutionarily conserved AT-rich sequence termed the P-element. Isl-1 binds the FLAT element weakly and does not appear to be present in the FLAT-binding complexes detected with extracts from insulin-producing cells; current evidence supports a more important role for Isl-1 in neural development. The homeodomain factors lmx-1 and cdx-3 have interesting transactivation properties with regard to insulin promoter function in heterologous cells, but their cellular distribution and FLAT-binding ability inside the β-cell remains unclear. In addition, there is little data that directly address the function of these factors in β-cell lines. Hence, there is currently no conclusive evidence that establishes any of these factors as a principal regulator of insulin gene expression.

Within the group of factors with insulin promoter-binding activity, STF-1 is perhaps the most promising candidate for a bona fide regulator of insulin promoter function. In mice, STF-1 is first detected at embryonic day 8.5 in the nuclei of primordial cells that gives rise to the pancreas, shortly prior to the earliest detected expression of insulin in this region. Throughout the ensuing development of the endocrine pancreas, STF-1 and insulin are largely coexpressed. In addition, in extracts from insulin-producing cell lines, STF-1 appears to be a component of the enidogenous DNA-binding activity at both the FLAT and P elements in the insulin promoter. STF-1 also strongly synergizes with the E-box-binding factor Pan-1, as might be expected from a FLAT-binding factor. However, DNA-binding assays indicate that other, unknown, factors from β-cell extracts also make a large contribution to the detected FLAT-binding activity. It remains unclear whether FLAT-mediated insulin promoter activity requires all, or only a subset, of these detected species.

In addition to a clear role for the FLAT-binding factors in determining β-cell-specific insulin gene expression, substantial evidence also implicates these factors in glucose-responsive insulin promoter function. However, there is currently no data whatsoever which evaluates the possible role of currently cloned FLAT-binding factors as mediators of the latter function.

SUMMARY OF THE INVENTION

In accordance with the present invention are provided islet-specific homeoprotein which are transcriptional regulators of insulin gene expression. Homeoprotein which are embodied by the present invention are preferentially expressed in insulin producing cells, and act as activators of insulin gene expression.

In its broadest aspect, the present invention extends to homeoprotein regulators of insulin gene expression having the following characteristics: binding to an element of an insulin gene promoter; being modulated by a $Ca^{++}$-dependent CaM kinase IV; and having homology to a nucleotide sequence encoded by a Hox gene complex.

In a further aspect, the homeoprotein of the invention have the following properties: (1) they bind the FLAT element of the insulin gene promoter; (2) they are synergistic with another regulator of insulin gene expression, namely Pan-1; (3) their active region is at or near the N-terminus of the protein; and (4) they map to a human chromosomal location on the long arm of chromosome 17.

In a specific example, the homeoprotein regulator of insulin gene expression is localized to human chromosome 17, at 17q21, and has the sequence of FIG. 2A (SEQ ID NO:5), encoded by the genomic nucleotide sequence of FIG. 2A (SEQ ID NO:3), or by the cDNA sequence of FIG. 2B (SEQ ID NO:4). In another specific example, the homeoprotein regulator of insulin gene expression is derived from rat, and has the sequence of FIG. 1 (SEQ ID NO:2) encoded by the nucleotide sequence of FIG. 1 (SEQ ID NO:1).

The present invention also relates to a recombinant DNA molecule or cloned gene, or a degenerate variant thereof, which encodes a homeoprotein regulator of insulin gene expression; preferably a nucleic acid molecule, in particular a recombinant DNA molecule or cloned gene, encoding the homeoprotein regulator of insulin gene expression and has a nucleotide sequence or is complementary to a DNA sequence shown in FIG. 1 (SEQ ID NO:1) or FIG. 2B (SEQ ID NO:4). In another embodiment, the DNA molecule has the sequence shown in FIG. 2A (SEQ ID NO:3).

The human and rat DNA sequences of the homeoprotein regulators of insulin gene expression of the present invention or portions thereof, may be prepared as probes to screen for complementary sequences and genomic clones in the same or alternate species. The present invention extends to probes so prepared that may be provided for screening cDNA and genomic libraries for the homeoprotein regulators of insulin gene expression. For example, the probes may be prepared with a variety of known vectors, such as the phage λ vector. The present invention also includes the preparation of plasmids including such vectors, and the use of the DNA sequences to construct vectors expressing antisense RNA or ribozymes which would attack the mRNAs of any or all of the DNA sequences set forth in FIGS. 1 and 2 (SEQ ID NOS:1 and 4, respectively). Correspondingly, the preparation of antisense RNA and ribozymes are included herein.

The present invention also includes homeoprotein regulators of insulin gene expression having the activities noted herein, and that display the amino acid sequences set forth and described above and selected from SEQ ID NOS:2 and 5.

In a further embodiment of the invention, the full DNA sequence of the recombinant DNA molecule or cloned gene so determined may be operatively linked to an expression control sequence which may be introduced into an appropriate host. The invention accordingly extends to unicellular hosts transformed with the cloned gene or recombinant DNA molecule comprising a DNA sequence encoding the present homeoprotein regulator(s) of insulin gene expression, and more particularly, the complete DNA sequence determined from the sequences set forth above and in SEQ ID NOS:1 and 4.

According to other preferred features of certain preferred embodiments of the present invention, a recombinant expression system is provided to produce biologically active animal or human homeoprotein regulators of insulin gene expression.

The concept of the homeoprotein regulators of insulin gene expression contemplates that specific factors exist for correspondingly specific ligands, such as HoxB13 for the FLAT element of the insulin gene promoter and the like, as described earlier. Accordingly, the exact structure of each homeoprotein regulator of insulin gene expression will understandably vary so as to achieve this ligand and activity specificity. It is this specificity and the direct involvement of the homeoprotein regulator of insulin gene expression in the chain of events leading to gene activation, that offers the promise of a broad spectrum of diagnostic and therapeutic utilities.

The present invention naturally contemplates several means for preparation of the homeoprotein regulator of insulin gene expression, including as illustrated herein known recombinant techniques, and the invention is accordingly intended to cover such synthetic preparations within its scope. The isolation of the cDNA and amino acid sequences disclosed herein facilitates the reproduction of the homeoprotein regulators of insulin gene expression by such recombinant techniques, and accordingly, the invention extends to expression vectors prepared from the disclosed DNA sequences for expression in host systems by recombinant DNA techniques, and to the resulting transformed hosts.

The invention includes an assay system for screening of potential drugs effective to modulate transcriptional activity of target mammalian cells by interrupting or potentiating the binding of the homeoprotein regulator of insulin gene expression. In one instance, the test drug could be administered to a cellular sample with the ligand which is activated by the homeoprotein regulator of insulin gene expression, or an extract containing the homeoprotein regulator of insulin gene expression, to determine its effect upon the binding activity of the homeoprotein regulator of insulin gene expression to any chemical sample (including DNA), or to the test drug, by comparison with a control.

The assay system could more importantly be adapted to identify drugs or other entities that are capable of binding to the homeoprotein regulator of insulin gene expression and/ or transcription factors or proteins, either in the cytoplasm or in the nucleus, thereby inhibiting or potentiating transcriptional activity. Such assay would be useful in the development of drugs that would be specific against particular cellular activity, or that would potentiate such activity, in time or in level of activity. For example, such drugs might be used to modulate cellular responses, or to treat pathologies, as for example, in making homeoprotein regulators of insulin gene expression more potent activators of insulin gene expression to increase levels of insulin in diabetic patients, or in making homeoprotein regulators of insulin gene expression less potent activators of insulin gene expression to decrease levels of insulin in hypoglycemic patients.

In yet a further embodiment, the invention contemplates antagonists of the activity of a homeoprotein regulator of insulin gene expression. In a specific embodiment, the antagonist can be a peptide having the sequence of a portion of a domain, particularly an N-terminal domain, of a homeoprotein regulator of insulin gene expression. Such peptides may be capable of disrupting binding of a homeoprotein regulator of insulin gene expression.

The diagnostic utility of the present invention extends to the use of the present homeoprotein regulator of insulin gene expression in assays to screen for the presence of the insulin gene or allelic variants or mutants thereof.

The present invention likewise extends to the development of antibodies against the homeoprotein regulator(s) of insulin gene expression, including naturally raised and recombinantly prepared antibodies. For example, the antibodies could be used to screen expression libraries to obtain the gene or genes that encode the homeoprotein regulator(s) of insulin gene expression. Such antibodies could include both polyclonal and monoclonal antibodies prepared by known genetic techniques, as well as bi-specific (chimeric) antibodies, and antibodies including other functionalities suiting them for additional diagnostic use conjunctive with their capability of modulating transcriptional activity.

In particular, antibodies against the homeoprotein regulators of insulin gene expression can be selected and are included within the scope of the present invention for their particular ability in following protein. Thus, activity of the homeoprotein regulators of insulin gene expression or of the specific polypeptides believed to be causally connected thereto may therefore be followed directly by the assay techniques discussed later on, through the use of an appropriately labeled quantity of the homeoprotein regulator of insulin gene expression or antibodies or analogs thereof.

Thus, the homeoprotein regulators of insulin gene expression, anal analogs and/or analogs, and any antagonists or antibodies that may be raised thereto, are capable of use in connection with various diagnostic techniques, including immunoassays, such as a radioimmunoassay, using for example, an antibody to the homeoprotein regulator of insulin gene expression that has been labeled by either radioactive addition, reduction with sodium borohydride, or radioiodination.

In an immunoassay, a control quantity of the antagonists or antibodies thereto, or the like may be prepared and labeled with an enzyme, a specific binding partner and/or a radioactive element, and may then be introduced into a cellular sample. After the labeled material or its binding partner(s) has had an opportunity to react with sites within the sample, the resulting mass may be examined by known techniques, which may vary with the nature of the label attached. For example, antibodies against specifically phosphorylated factors may be selected and appropriately employed in the exemplary assay protocol, for the purpose of following activated protein as described above.

In the instance where a radioactive label, such as the isotopes $^{3}H$, $^{14}C$, $^{32}P$, $^{35}S$, $^{36}Cl$, $^{51}Cr$, $^{57}Co$, $^{58}Co$, $^{59}Fe$, $^{90}Y$, $^{125}I$, $^{131}I$, and $^{186}Re$ are used, known currently available counting procedures may be utilized. In the instance where the label is an enzyme, detection may be accomplished by any of the presently utilized calorimetric, spectrophotometric, fluorospectrophotometric, ampierometric or gasonmetric techniques known in the art.

The present invention includes an assay system which may be prepared in the form of a test kit for the quantitative analysis of the extent of the presence of the homeoprotein regulators of insulin gene expression, or to identify drugs or other agents that may mimic or block their activity. The system or test kit may comprise a labeled component prepared by one of the radioactive and/or enzymatic techniques discussed herein, coupling a label to the homeoprotein regulators of insulin gene expression, their agonists and/or antagonists, and one or more additional immunochemical reagents, at least one of which is a free or immobilized ligand, capable either of binding with the labeled component, its binding partner, one of the components to be determined or their binding partner(s).

In a further embodiment, the present invention relates to certain therapeutic methods which would be based upon the activity of the homeoprotein regulators of insulin gene expression, its (or their) subunits, or active fragments thereof, or upon agents or other drugs determined to possess the same activity. A first therapeutic method is associated with the prevention of the manifestations of conditions causally related to or following from the binding activity of the homeoprotein regulator of insulin gene expression or its subunits, and comprises administering an agent capable of modulating the production and/or activity of the homeoprotein regulator of insulin gene expression or subunits thereof, either individually or in mixture with each other in an amount effective to prevent the development of those conditions in the host.

For example, drugs or other binding partners to the homeoprotein regulators of insulin gene expression or proteins may be administered to inhibit or potentiate transcriptional activity, as in the potentiation of homeoprotein regulators of insulin gene expression in diabetes therapy.

More specifically, the therapeutic method generally referred to herein could include the method for the treatment of various pathologies or other cellular dysfunctions and derangements by the administration of pharmaceutical compositions that may comprise effective inhibitors or enhancers of activation of the homeoprotein regulator of insulin gene expression or its subunits, or other equally effective drugs developed for instance by a drug screening assay prepared and used in accordance with a further aspect of the present invention. For example, drugs or other binding partners to the homeoprotein regulators of insulin gene expression or proteins, as represented by SEQ ID NOS:2 and 5, may be administered to inhibit or potentiate transcriptional activity, as in the potentiation of homeoprotein regulators of insulin gene expression in diabetes therapy. Correspondingly, the inhibition or blockade of the activation or binding of the homeoprotein regulators of insulin gene expression would affect MHC Class II expression and consequently, would promote immunosuppression. Materials exhibiting this activity, as illustrated later on herein by staurosporine, may be useful in instances such as the treatment of autoimmune diseases and graft rejection, where a degree of immunosuppression is desirable.

In particular, the proteins whose sequences are presented in SEQ ID NOS:2 and 5 herein, their antibodies, agonists, antagonists, or active fragments thereof, could be prepared in pharmaceutical formulations for administration in instances wherein insulin therapy is appropriate, such as to treat diabetes, hyper- or hypoglycemia. The specificity of the homeoprotein regulators of insulin gene expression hereof would make it possible to better manage the aftereffects of current diabetes therapy, and would thereby make it possible to apply homeoprotein regulators of insulin gene expression as a general anti-diabetic agent.

Accordingly, it is a principal object of the present invention to provide a homeoprotein regulator of insulin gene expression and its subunits in purified form that exhibits certain characteristics and activities associated with transcriptional promotion of cellular activity.

It is a further object of the present invention to provide antibodies to the homeoprotein regulator of insulin gene expression and its subunits, and methods for their preparation, including recombinant means.

It is a further object of the present invention to provide a method for detecting the presence of the homeoprotein regulator of insulin gene expression and its subunits in mammals in which invasive, spontaneous, or idiopathic pathological states are suspected to be present.

It is a further object of the present invention to provide a method and associated assay system for screening substances such as drugs, agents and the like, potentially effective in either mimicking the activity or combating the adverse effects of the homeoprotein regulator of insulin gene expression and/or its subunits in mammals.

It is a still further object of the present invention to provide a method for the treatment of mammals to control the amount or activity of the homeoprotein regulator of insulin gene expression or subunits thereof, so as to alter the adverse consequences of such presence or activity, or where beneficial, to enhance such activity.

It is a still further object of the present invention to provide a method for the treatment of mammals to control the amount or activity of the homeoprotein regulator of insulin gene expression or its subunits, so as to treat or avert the adverse consequences of invasive, spontaneous or idiopathic pathological states.

It is a still further object of the present invention to provide pharmaceutical compositions for use in therapeutic methods which comprise or are based upon the homeoprotein regulator of insulin gene expression, its subunits, their binding partner(s), or upon agents or drugs that control the production, or that mimic or antagonize the activities of the homeoprotein regulator of insulin gene expression.

With the foregoing and other objects, advantages and features of the invention that will become hereinafter apparent, the nature of the invention may be more clearly understood by reference to the following detailed description of the preferred embodiments of the invention and to the appended claims, taken in conjunction with the following illustrative drawings.

BRIEF DESCRIPTION OF THE DRAWINGS

FIG. 2A depicts the human HoxB13 gene (SEQ ID NO:3) and 2B depicts the HoxB13 cDNA (SEQ ID NO:4) and protein sequence (SEQ ID NO:5).

FIG. 8 is a computer-generated homology analysis of HoxB13. It can be seen that HoxB13 (SEQ ID NO:43) shares 80.3% identity in a 66 amino acid overlap with the human HoxA13 (SEQ ID NO:44) sequence, 75.8% identity in a 66 amino acid overlap with the human HoxC13 (SEQ ID NO:45) sequence, and a 72.1% identity in a 68 amino acid overlap with chick HoxD13 (SEQ ID NO:46).

FIG. 9 is a Southern blot of PCR amplifications of chromosomal DNA demonstrating 17q21 localization for HoxB13. Cell lines 498 (which contains all of chromosome 17), 500 and 600 are positive for 17q21 localization. Cell lines 660 (p arm of chromosome) and 659 (17q23— telomere) do not amplify.

FIG. 10 is a Southern blot of PCR amplifications of chromosomal DNA from a YAC termed Hox2 B160B1, which demonstrates that the HoxB13 sequence is not amplified from this YAC.

FIG. 13 is a Kyte-Doolittle analysis of the rat CIX-1 protein sequence. FIG. 13F shows the same analysis [(1)–(7)] of the entire rat CIX-1 coding sequence with a hydrophilicity window size of 4.

DETAILED DESCRIPTION

Figure 3:
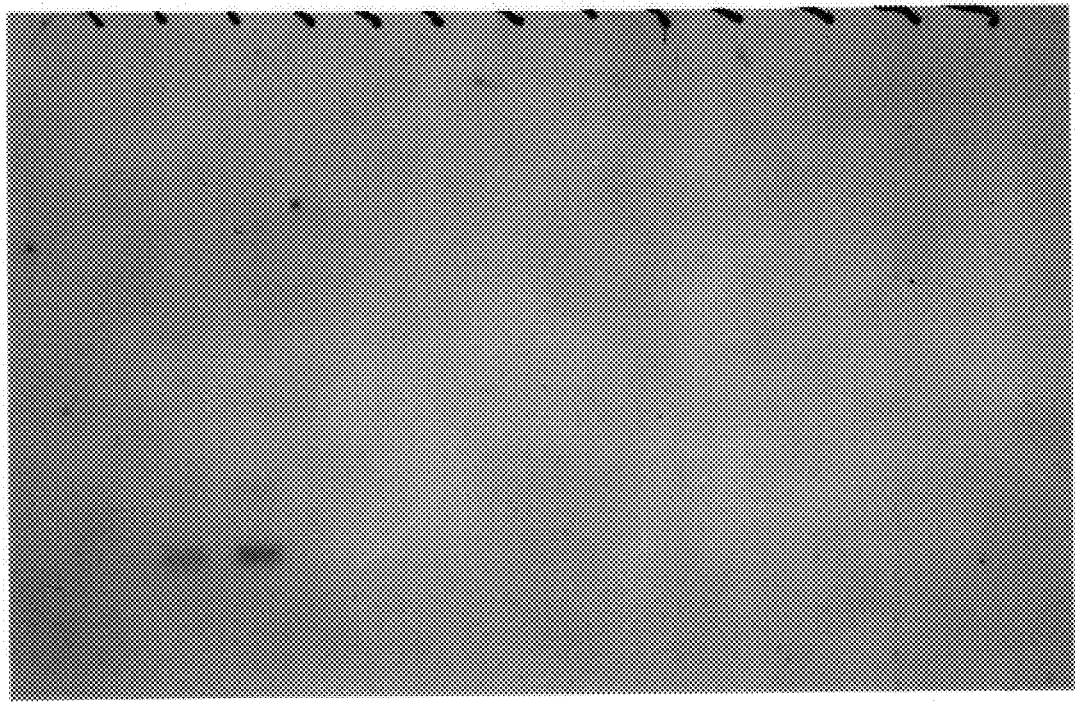
FIG. 3 is RNA analysis (Northern blot) of various cell lines probed with Isl-3. 10 μg of each RNA was run on a 1% agarose/formaldehyde gel at 150V for 2¾ hours. A 3-day exposure shows expression of a predominant band at 1.5 kb. The expression of HoxB13 is similar to that of STF-1. Results show HoxB13 only in two insulin-producing cell lines (Tu6 and RIN).

The present invention utilizes a PCR-based approach to identify novel, islet-specific homeoprotein and to subsequently evaluate their role in the transcriptional control of the insulin gene.

Preliminary Considerations

The human genome contains four clusters of genes, termed Hox or homeotic selector genes, which are critical determinants of axial body pattern formation during embryogenesis (Krumlauf, 1994 Cell 78: 191–201). The four clusters each contain up to 13 genes, and a given gene in one cluster usually has particularly high homology with a member of the other three families. Such related genes are termed paralogs; hence HoxA1, HoxB1, HoxC1 and HoxD1 are all closely related paralogs, each in a different Hox cluster on a different chromosome. The HoxB complex is on the long arm of chromosome 17, and until the present invention only HoxB1 through HoxB9 had been identified. The HoxB13 gene, which is a particular embodiment of the present invention, is highly related to HoxA13, HoxC13 and HoxD13 (FIG. 8), and moreover maps to the same subregion of chromosome 17 as the HoxB complex (FIGS. 9 and 10).

Abundant evidence suggests that homeodomain-containing proteins are crucial regulators of insulin gene expression. However, there is currently no conclusive evidence as to which homeoprotein, or how many, are involved in this process. The identification of one of genes of the present invention as HoxB13 suggests that HoxB13 functions both as an important player in body pattern formation during embryogenesis and in the control of insulin gene expression in the adult. The present invention relates in particular to HoxB13, which is so termed because of its location in the human HoxB locus at 17q21 and its homology to paralogous loci in the other Hox complexes. The assignment of this gene to a Hox locus suggests a possible role in axial pattern formation during embryogenesis. However, when 17 cell lines were analyzed for HoxB13 expression, HoxB13 mRNA was detected in only two of these, both of which are islet-derived, insulin-producing lines. Thus, the possibility that HoxB13 might participate in the transcriptional control of insulin expression was pursued.

Glucose-dependent regulation of the insulin gene appears to occur in concert with glucose-mediated increases in the secretion of insulin. This may be due in part to increases in intracellular calcium. In addition, glucose-responsive insulin promoter function may occur at least in part by modulating the activity of FLAT-binding proteins. HoxB13 binds the functionally important FLAT element of the insulin promoter with high affinity. Additionally, HoxB13 and the insulin ICE/Nir element-binding factor Pan-1 strongly activate the insulin promoter when added in combination. This is consistent with the observation that the FLAT and Nir elements function synergistically in insulin-producing cells. Collectively, these data suggested that calcium-dependent signaling pathways might regulate the function of HoxB13. Remarkably, it was found that the activity of HoxB13 was strongly enhanced in the presence of co-transfected calmodulin-dependent protein kinase IV (CaM kinase IV). Thus, HoxB13 appears to be a critical regulator of insulin gene expression.

Moreover, the location of HoxB13 in the vicinity of the gene implicated in hereditary breast cancer, BRCA-1, and the fact that (1) the BRCA-1 gene appears normal in the sporadic breast cancers evaluated to date; and (2) mutations in the chromosomal region of BRCA-1 are also associated with sporadic breast cancer, indicates that HoxB13 may also be an additional breast cancer susceptibility gene. Thus, the HoxB13 gene could also be used in pharmaceutical compositions or in gene therapy methods as a treatment for breast cancer.

In accordance with the present invention there may be employed conventional molecular biology, microbiology, and recombinant DNA techniques within the skill of the art. Such techniques are explained fully in the literature. See, e.g., Maniatis, Fritsch & Sambrook, "Molecular Cloning: A Laboratory Manual" (1982); "DNA Cloning: A Practical Approach," Volumes I and II (D. N. Glover ed. 1985); "Oligonucleotide Synthesis" (M. J. Gait ed. 1984); "Nucleic Acid Hybridization" [B. D. Hames & S. J. Higgins eds. (1985)]; "Transcription And Translation" [B. D. Hames & S. J. Higgins, eds. (1984)]; "Animal Cell Culture" [R. I. Freshney, ed. (1986)]; "Immobilized Cells And Enzymes" [IRL Press, (1986)]; B. Perbal, "A Practical Guide To Molecular Coiling" (1984).

Therefore, if appearing herein, the following terms shall have the definitions set out below.

Figures 5, 13A:
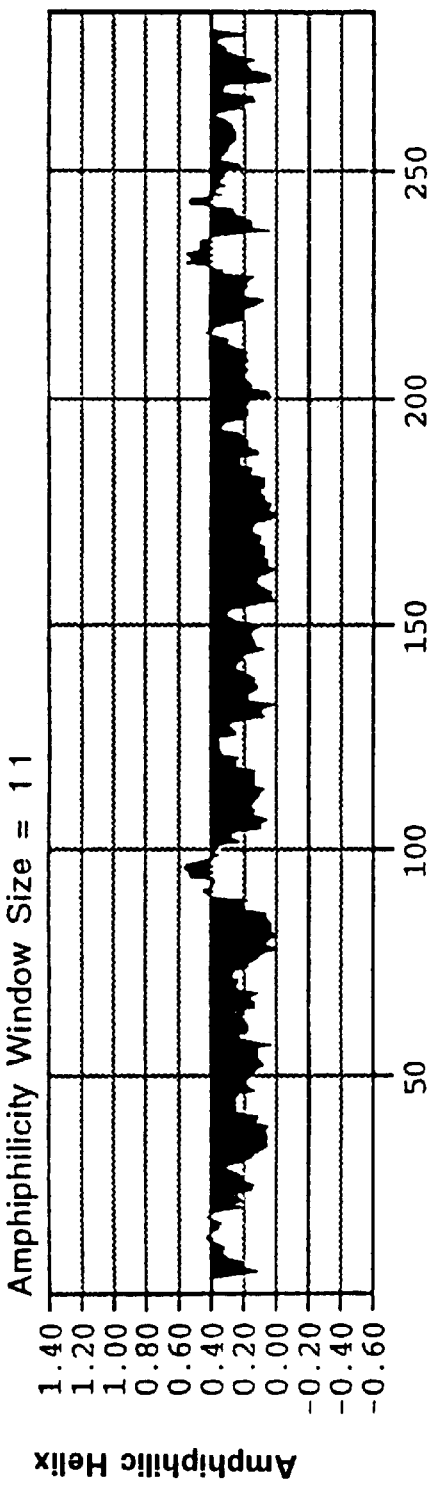
FIG. 13A shows the (1) hydrophilicity; (2) surface probability; (3) flexibility; (4) antigenic index; (5) amphiphilic helix; (6) amphiphilic sheet; and (7) secondary structure of the entire coding sequence with a hydrophilicity window size of 7.
Figures 6, 13A:
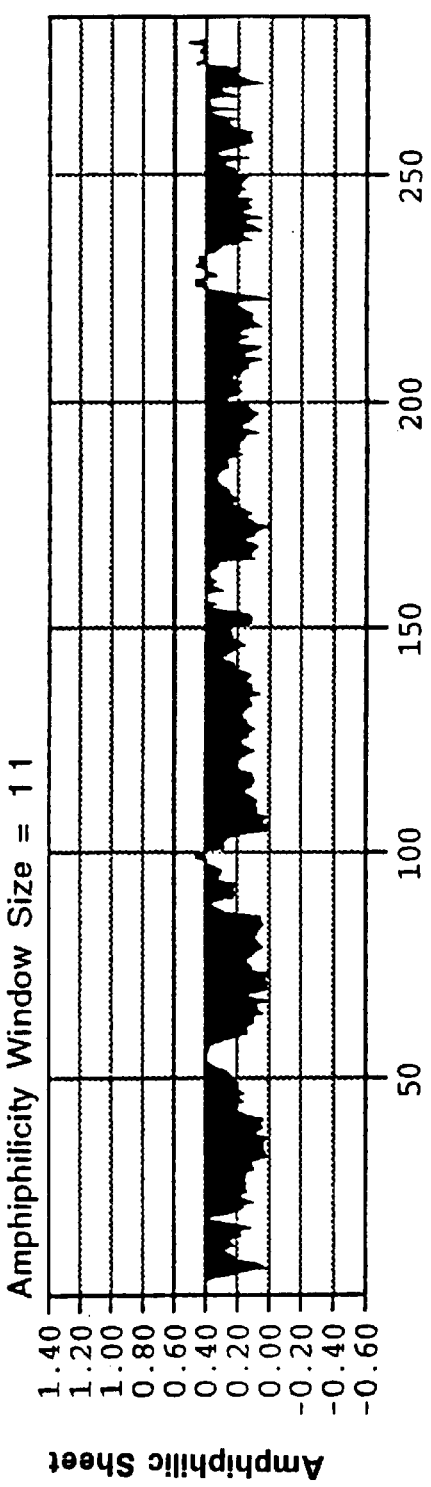
Figures 7, 13A:
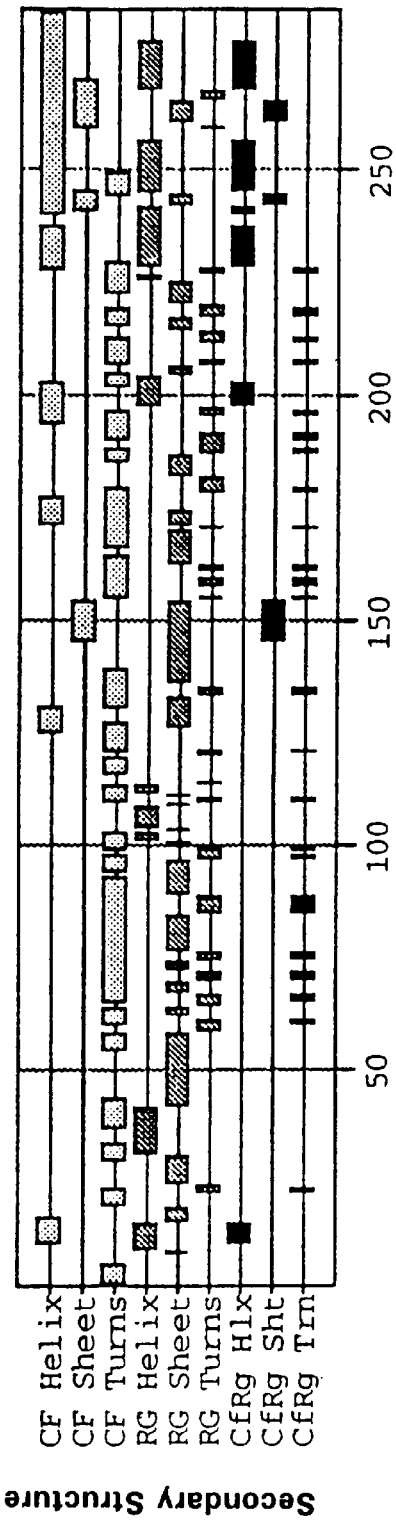
Figures 1, 13B:
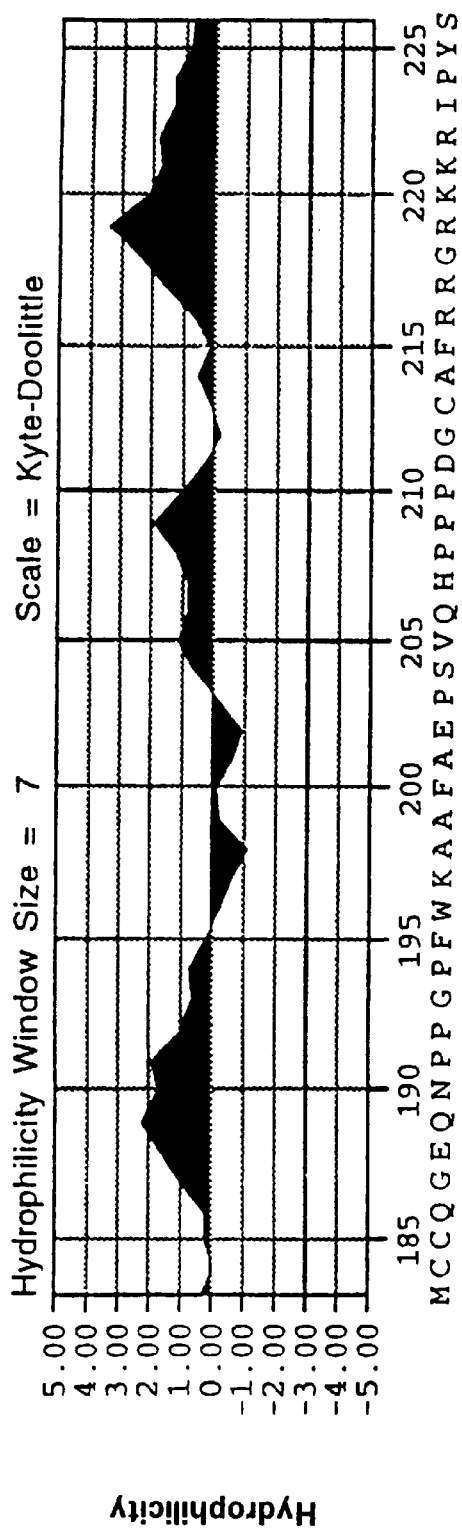
FIG. 1 depicts the rat CIX-1 (HoxB13) cDNA (SEQ ID NO:1) and translated protein sequence (SEQ ID NO:2). The homeodomain is underlined.
FIG. 13B shows the same analysis [(1)–(7)] for amino acids 183–226 (SEQ ID NO:47) of the rat CIX-1.
Figures 6, 13B:
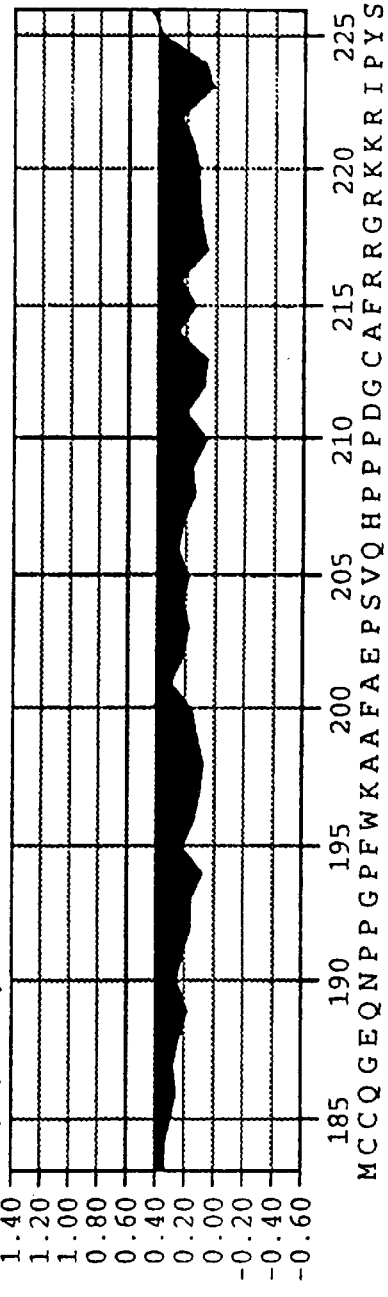
Figures 7, 13B:
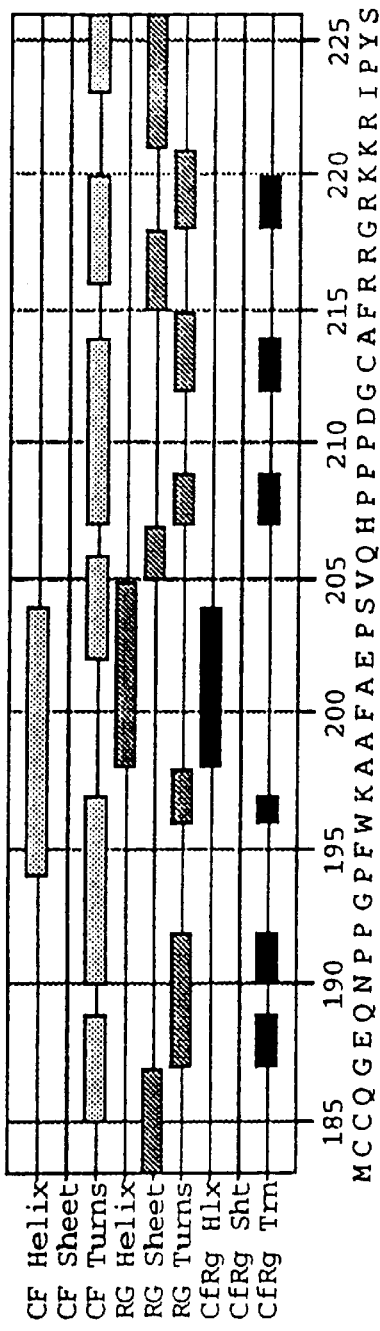
Figures 3, 13C:
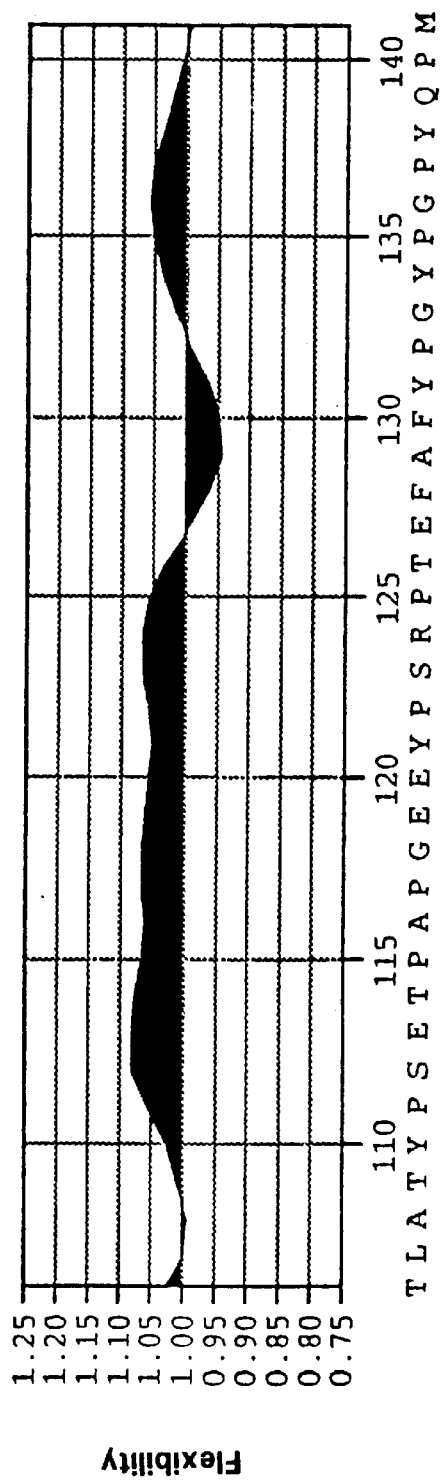
FIG. 13C shows the same analysis [(1)–(7)] for amino acids 106–141 (SEQ ID NO:48) of the rat CIX-1.
Figures 4, 13C:
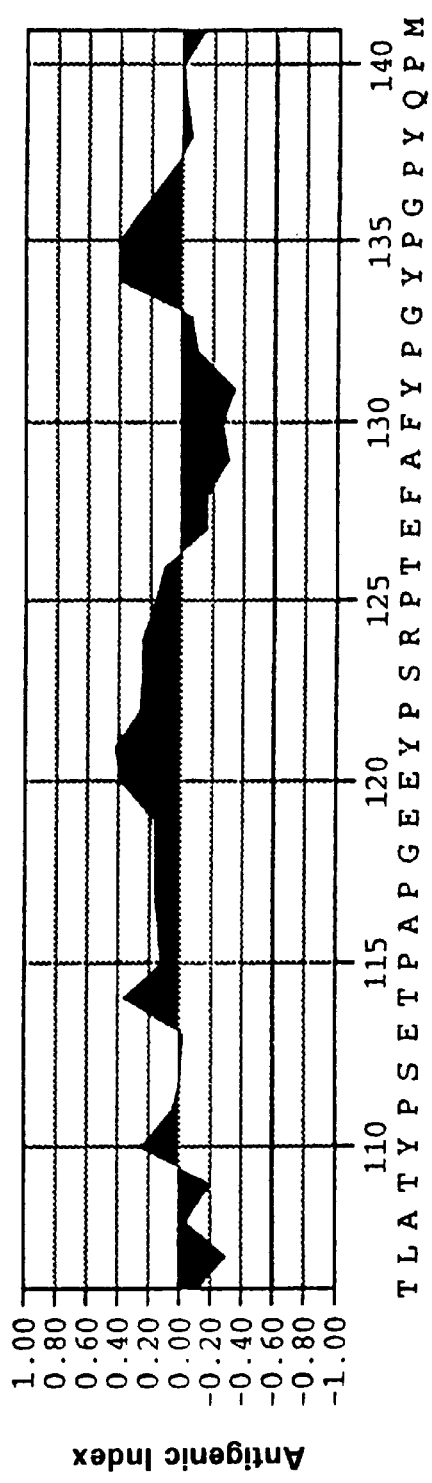
Figures 2, 13D:
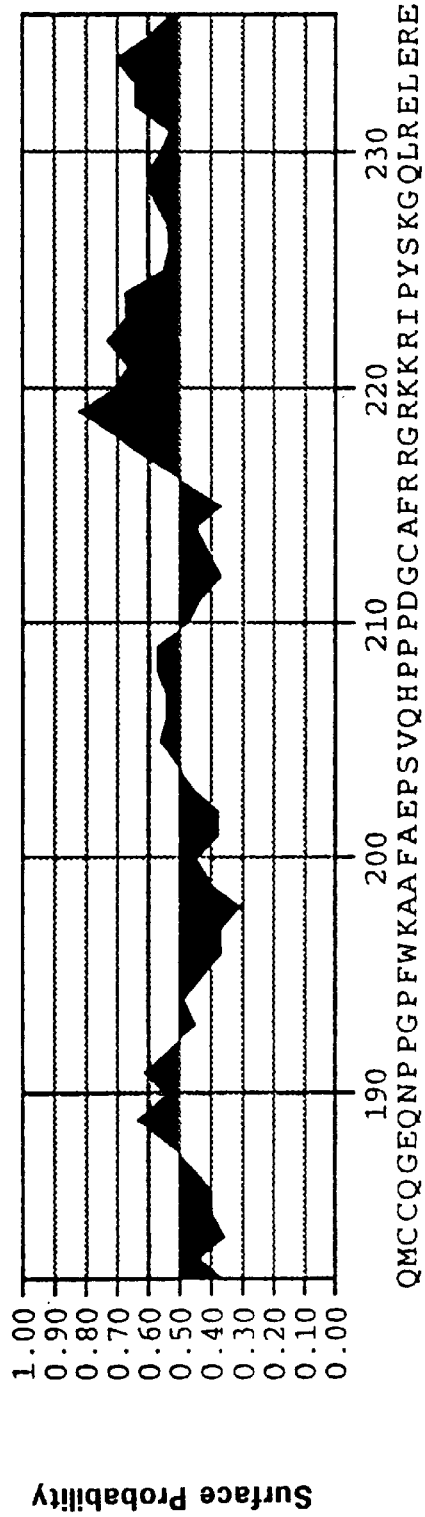
FIG. 13D shows the same analysis [(1)–(7)] for amino acids 182–236 (SEQ ID NO:49) of the rat CIX-1.
Figures 3, 13D:
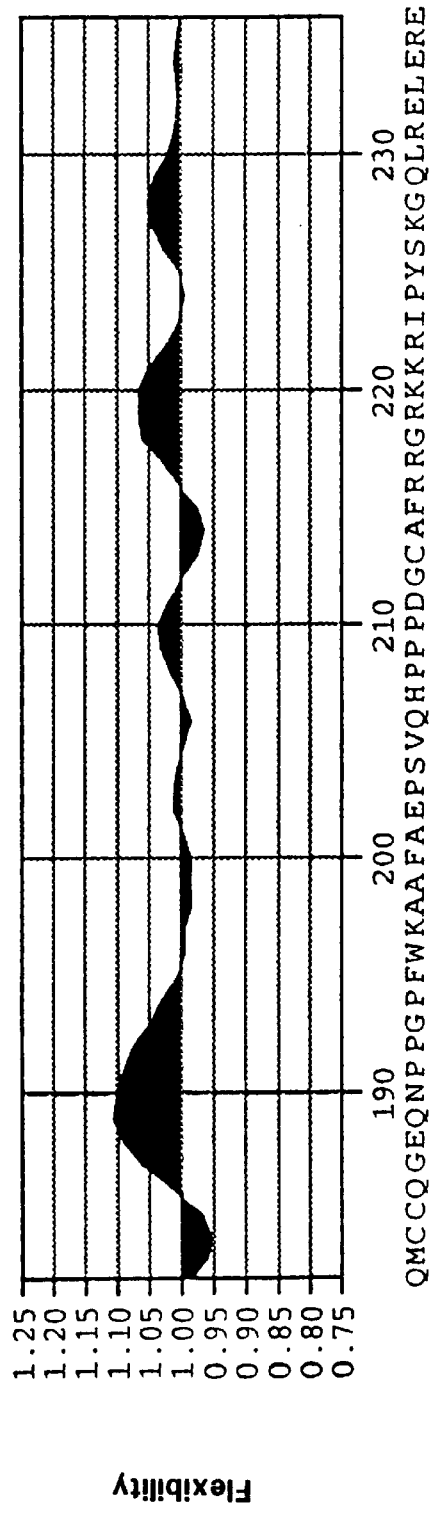
Figures 4, 13D:
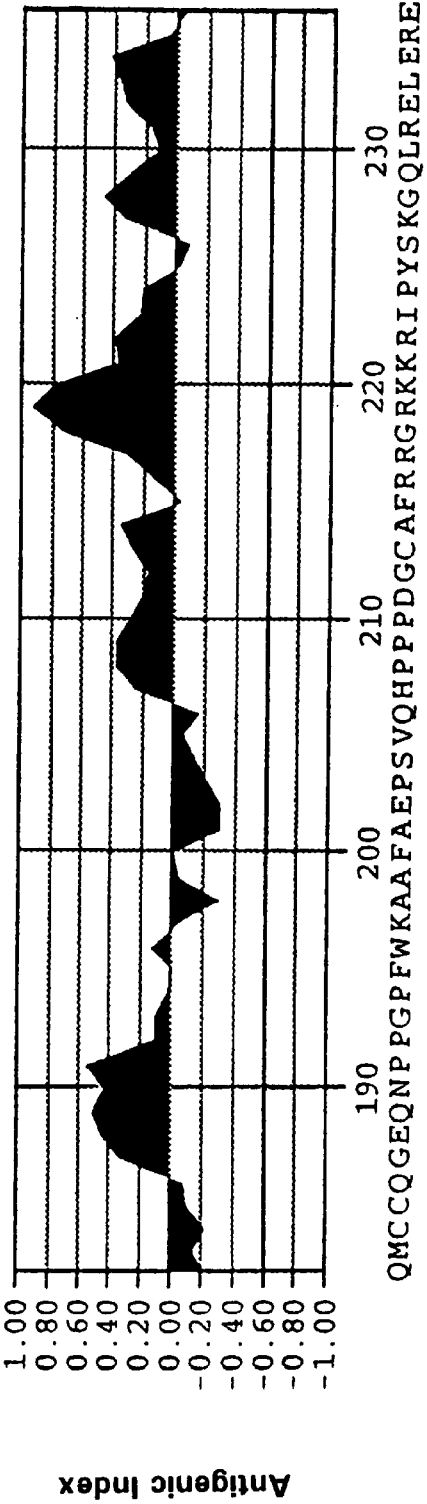
Figures 5, 13D:
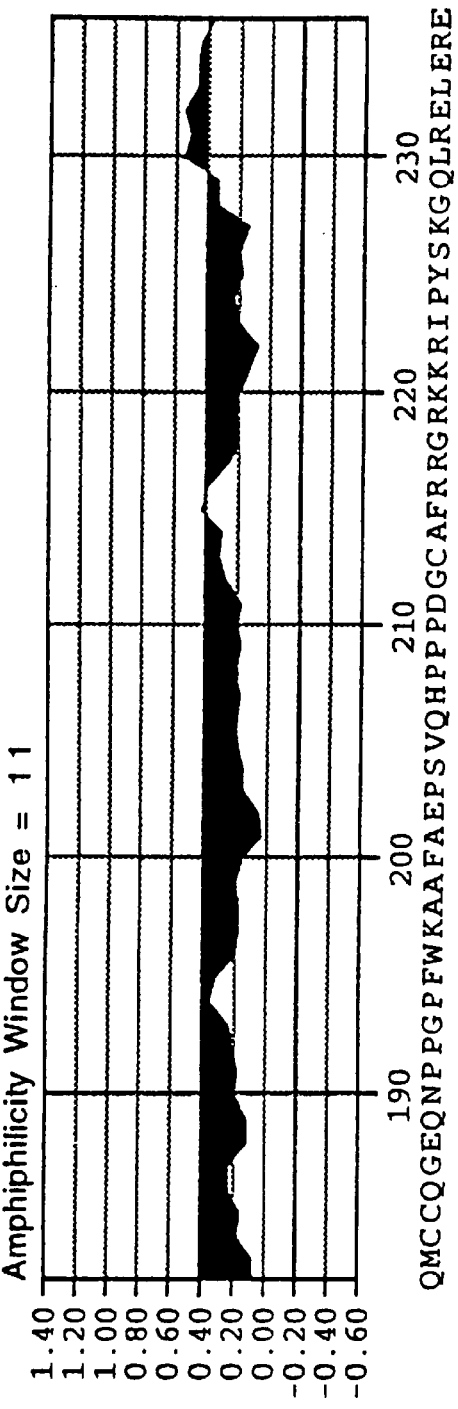
Figures 6, 13D:
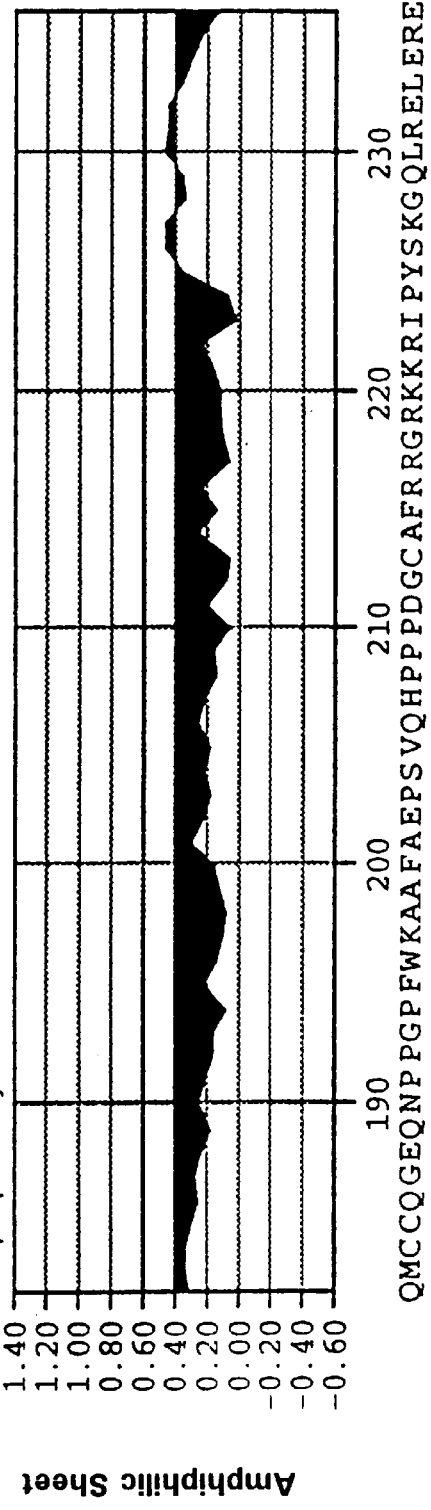
Figures 7, 13D:
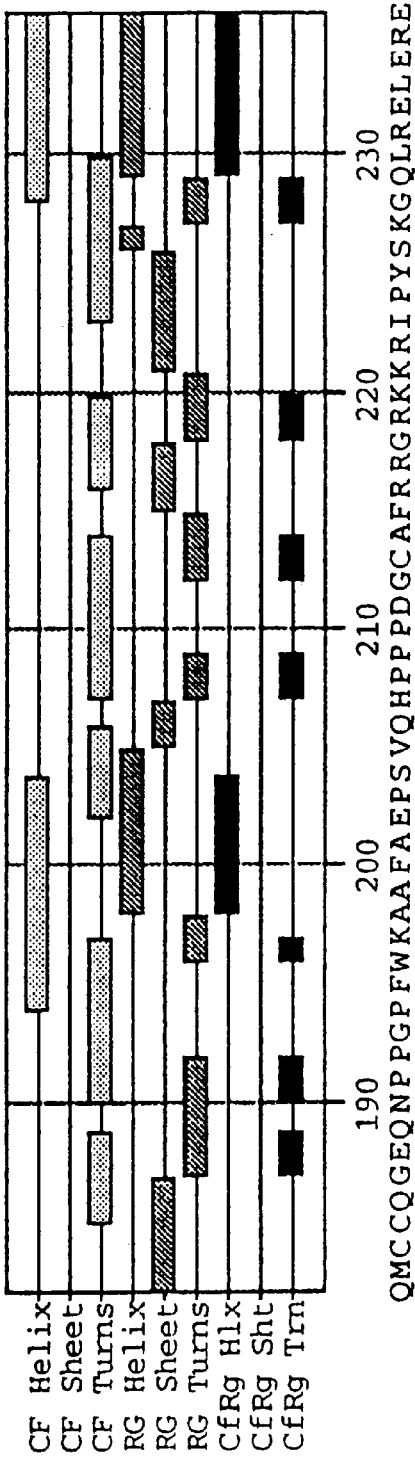
Figures 3, 13E:
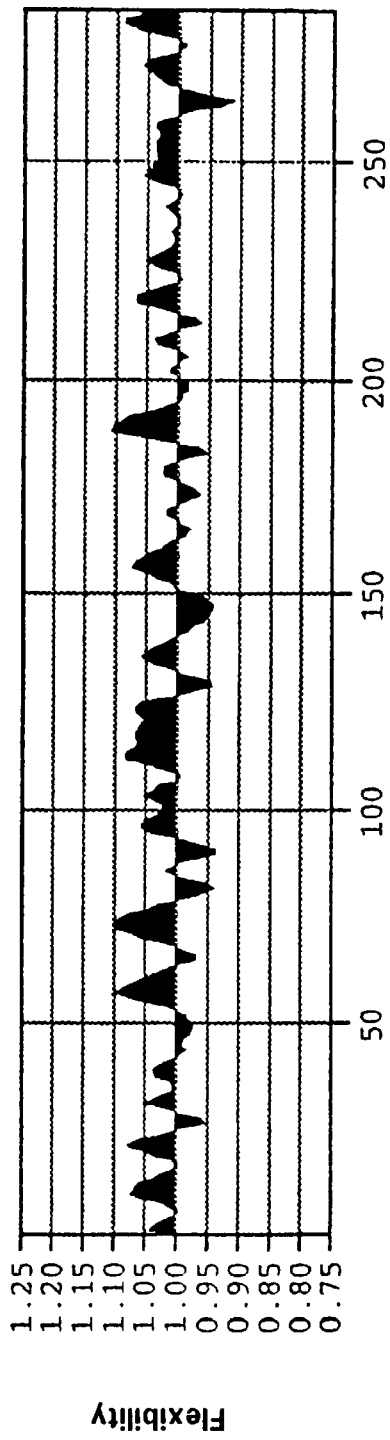
FIG. 13E shows the same analysis [(1)–(7)] for amino acids 182–236 (SEQ ID NO:49) of the rat CIX-1.
Figures 4, 13E:
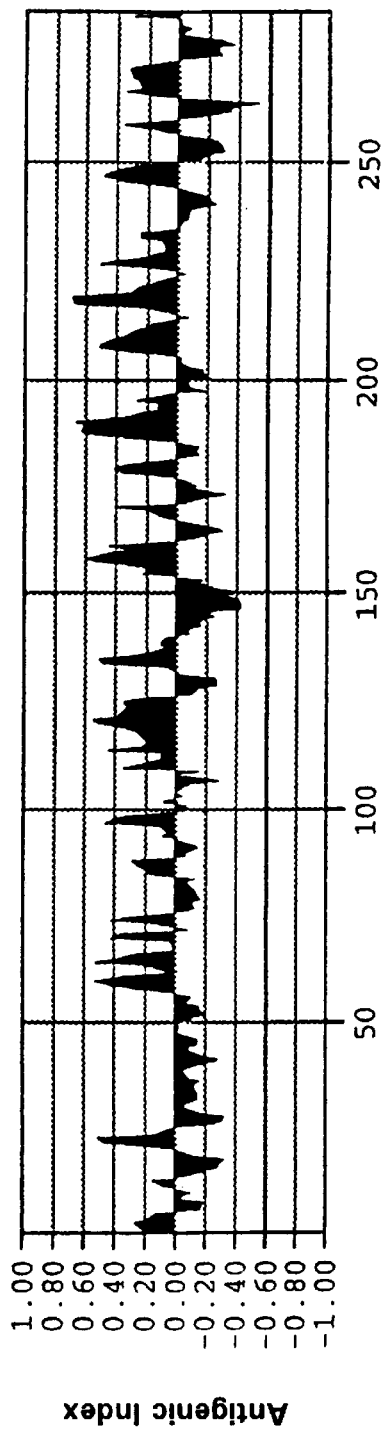
Figures 7, 13E:
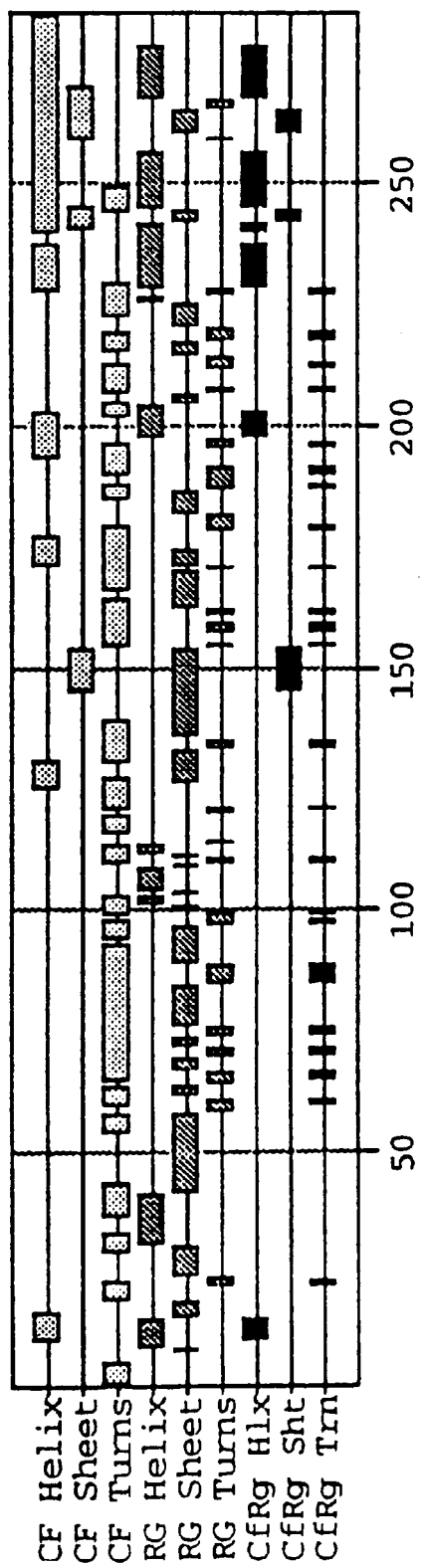

The terms "gene encoding a homeoprotein regulator of insulin gene expression," "homeoprotein gene," "homeotic selector gene," and "gene encoding a homeodomain-containing protein or factor," and any variants not specifically listed, may be used herein interchangeably, and as used throughout the present application and claims refer to proteinaceous material including single or multiple proteins, and extends to those proteins having the amino acid sequence data described herein and presented in FIG. 1 (SEQ ID NO:2) or FIG. 2 (SEQ ID NO:5), and the profile of activities set forth herein and in the Claims. More specifically, the terms "Isl-3," "CIX-1" and "HoxB13 ", and any variants not specifically listed, may be used herein interchangeably, and as used throughout the present application and claims refer to proteinaceous material including single or multiple proteins, and extends to those proteins having the amino acid sequence data described herein and presented in FIG. 1 (SEQ ID NO:2) and FIG. 2 (SEQ ID NO:5), and the profile of activities set forth herein and in the Claims. Accordingly, proteins displaying substantially equivalent or altered activity are likewise contemplated. These modifications may be deliberate, for example, such as modifications obtained through site-directed mutagenesis, or may be accidental, such as those obtained through mutations in hosts that are producers of the complex or its named subunits. Also, the terms "homeoprotein regulator of insulin gene expression," "homeodomain protein," "homeotic selector protein" and "homeoprotein" are intended to include within their scope proteins specifically recited herein as well as all substantially homologous analogs and allelic variations.

The amino acid residues described herein are preferred to be in the "L" isomeric form. However, residues in the "D" isomeric form can be substituted for any L-amino acid residue, as long as the desired functional property of immunoglobulin-binding is retained by the polypeptide. NH2 refers to the free amino group present at the amino terminus of a polypeptide. COOH refers to the free carboxy group present at the carboxy terminus of a polypeptide. In keeping with standard polypeptide nomenclature, *J. Biol. Chem.*, 243: 3552–59 (1969), abbreviations for amino acid residues are shown in the following Table of Correspondence:

| TABLE OF CORRESPONDENCE | | |
|---|---|---|
| SYMBOL | | |
| 1-Letter | 3-Letter | AMINO ACID |
| Y | Tyr | tyrosine |
| G | Gly | glycine |
| F | Phe | phenylalanine |
| M | Met | methionine |
| A | Ala | alanine |
| S | Ser | serine |
| I | Ile | isoleucine |
| L | Leu | leucine |
| T | Thr | threonine |
| V | Val | valine |
| P | Pro | proline |
| K | Lys | lysine |
| H | His | histidine |
| Q | Gln | glutamine |
| E | Glu | glutamic acid |
| W | Trp | tryptophan |
| R | Arg | arginine |
| D | Asp | aspartic acid |
| N | Asn | asparagine |
| C | Cys | cysteine |

It should be noted that all amino-acid residue sequences are represented herein by formulae whose left and right orientation is in the conventional direction of amino-terminus to carboxy-terminus. Furthermore, it should be noted that a dash at the beginning or end of an amino acid residue sequence indicates a peptide bond to a further sequence of one or more amino-acid residues. The above Table is presented to correlate the three-letter and one-letter notations which may appear alternately herein.

A "replicon" is any genetic element (e.g., plasmid, chromosome, virus) that functions as an autonomous unit of DNA replication in vivo; i.e., capable of replication under its own control.

A "vector" is a replicon, such as plasmid, phage or cosmid, to which another DNA segment may be attached so as to bring about the replication of the attached segment.

A "DNA molecule" refers to the polymeric form of deoxyribonucleotides (adenine, guanine, thymine, or cytosine) in its either single stranded form, or a double-stranded helix. This term refers only to the primary and secondary structure of the molecule, and does not limit it to any particular tertiary forms. Thus, this term includes double-stranded DNA found, inter alia, in linear DNA molecules (e.g., restriction fragments), viruses, plasmids, and chromosomes. In discussing the structure of particular double-stranded DNA molecules, sequences may be described herein according to the normal convention of giving only the sequence in the 5' to 3' direction along the nontranscribed strand of DNA (i.e., the strand having a sequence homologous to the mRNA).

An "origin of replication" refers to those DNA sequences that participate in DNA synthesis.

A DNA "coding sequence" is a double-stranded DNA sequence which is transcribed and translated into a polypeptide in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, prokaryotic sequences, cDNA from eukaryotic mRNA, genomic DNA sequences from eukaryotic (e.g., mammalian) DNA, and even synthetic DNA sequences. A polyadenylation signal and transcription termination sequence will usually be located 3' to the coding sequence.

Transcriptional and translational control sequences are DNA regulatory sequences, such as promoters, enhancers, polyadenylation signals, terminators, and the like, that provide for the expression of a coding sequence in a host cell.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined by mapping with nuclease S1), as well as protein binding domains (consensus sequences) responsible for the binding of RNA polymerase. Eukaryotic promoters will often, but not always, contain "TATA" boxes and "CAT" boxes. Prokaryotic promoters contain Shine-Dalgarno sequences in addition to the −10 and −35 consensus sequences.

An "expression control sequence" is a DNA sequence that controls and regulates the transcription and translation of another DNA sequence. A coding sequence is "under the control" of transcriptional and translational control sequences in a cell when RNA polymerase transcribes the coding sequence into mRNA, which is then translated into the protein encoded by the coding sequence.

A "signal sequence" can be included before the coding sequence. This sequence encodes a signal peptide, N-terminal to the polypeptide, that communicates to the host cell to direct the polypeptide to the cell surface or secrete the polypeptide into the media, and this signal peptide is clipped off by the host cell before the protein leaves the cell. Signal sequences can be found associated with a variety of proteins native to prokaryotes and eukaryotes.

The term "oligonucleotide", as used herein in referring to the probe of the present invention, is defined as a molecule comprised of two or more ribonucleotides, preferably more than three. Its exact size will depend upon many factors which, in turn, depend upon the ultimate function and use of the oligonucleotide.

The term "primer" as used herein refers to an oligonucleotide, whether occurring naturally as in a purified restriction digest or produced synthetically, which is capable of acting as a point of initiation of synthesis when placed under conditions in which synthesis of a primer extension product, which is complementary to a nucleic acid strand, is induced, i.e., in the presence of nucleotides and an inducing agent such as a DNA polymerase and at a suitable temperature and pH. The primer may be either single-stranded or double-stranded and must be sufficiently long to prime the synthesis of the desired extension product in the presence of the inducing agent. The exact length of the primer will depend upon many factors, including temperature, source of primer and use of the method. For example, for diagnostic applications, depending on the complexity of the target sequence, the oligonucleotide primer typically contains 15–25 or more nucleotides, although it may contain fewer nucleotides.

The primers herein are selected to be "substantially" complementary to different strands of a particular target DNA sequence. This means that the primers must be sufficiently complementary to hybridize with their respective strands. Therefore, the primer sequence need not reflect the exact sequence of the template. For example, a non-complementary nucleotide fragment may be attached to the 5' end of the primer, with the remainder of the primer sequence being complementary to the strand. Alternatively, non-complementary bases or longer sequences can be interspersed into the primer, provided that the primer sequence has sufficient complementarity with the sequence of the strand to hybridize therewith and thereby form the template for the synthesis of the extension product.

As used herein, the terms "restriction endonucleases" and "restriction enzymes" refer to bacterial enzymes, each of which cut double-stranded DNA at or near a specific nucleotide sequence.

A cell has been "transformed" by exogenous or heterologous DNA when such DNA has been introduced inside the cell. The transforming DNA may or may not be integrated (covalently linked) into chromosomal DNA making up the genome of the cell. In prokaryotes, yeast, and mammalian cells for example, the transforming DNA may be maintained on an episomal element such as a plasmid. With respect to eukaryotic cells, a stably transformed cell is one in which the transforming DNA has become integrated into a chromosome so that it is inherited by daughter cells through chromosome replication. This stability is demonstrated by the ability of the eukaryotic cell to establish cell lines or clones comprised of a population of daughter cells containing the transforming DNA. A "clone" is a population of cells derived from a single cell or common ancestor by mitosis. A "cell line" is a clone of a primary cell that is capable of stable growth in vitro for many generations.

Two DNA sequences are "substantially homologous" when at least about 75% (preferably at least about 80%, and most preferably at least about 90 or 95%) of the nucleotides match over the defined length of the DNA sequences. Sequences that are substantially homologous can be identified by comparing the sequences using standard software available in sequence data banks, or in a Southern hybridization experiment under, for example, stringent conditions as defined for that particular system. Defining appropriate hybridization conditions is within the skill of the art. See, e.g., Maniatis et al., supra; DNA Cloning, Vols. I & II, supra; Nucleic Acid Hybridization, supra.

A "heterologous" region of the DNA construct is an identifiable segment of DNA within a larger DNA molecule that is not found in association with the larger molecule in nature. Thus, when the heterologous region encodes a mammalian gene, the gene will usually be flanked by DNA that does not flank the mammalian genomic DNA in the genome of the source organism. Another example of a heterologous coding sequence is a construct where the coding sequence itself is not found in nature (e.g., a cDNA where the genomic coding sequence contains introns, or synthetic sequences having codons different than the native gene). Allelic variations or naturally-occurring mutational events do not give rise to a heterologous region of DNA as defined herein.

An "antibody" is any immunoglobulin, including antibodies and fragments thereof, that binds a specific epitope. The term encompasses polyclonal, monoclonal, and chimeric antibodies, the last mentioned described in further detail in U.S. Pat. Nos. 4,816,397 and 4,816,567.

An "antibody combining site" is that structural portion of an antibody molecule comprised of heavy and light chain variable and hypervariable regions that specifically binds antigen.

The phrase "antibody molecule" in its various grammatical forms as used herein contemplates both an intact immunoglobulin molecule and an immunologically active portion of an immunoglobulin molecule.

Exemplary antibody molecules are intact immunoglobulin molecules, substantially intact immunoglobulin molecules and those portions of an immunoglobulin molecule that contains the paratope, including those portions known in the art as Fab, Fab', F(ab')$_2$ and F(v), which portions are preferred for use in the therapeutic methods described herein.

Fab and F(ab')$_2$ portions of antibody molecules are prepared by the proteolytic reaction of papain and pepsin, respectively, on substantially intact antibody molecules by methods that are well-known. See for example, U.S. Pat. No. 4,342,566 to Theofilopolous et al. Fab' antibody molecule portions are also well-known and are produced from F(ab')$_2$ portions followed by reduction of the disulfide bonds linking the two heavy chain portions as with mercaptoethanol, and followed by alkylation of the resulting protein mercaptan with a reagent such as iodoacetamide. An antibody containing intact antibody molecules is preferred herein.

The phrase "monoclonal antibody" in its various grammatical forms refers to an antibody having only one species of antibody combining site capable of immunoreacting with a particular antigen. A monoclonal antibody thus typically displays a single binding affinity for any antigen with which it immunoreacts. A monoclonal antibody may therefore contain an antibody molecule having a plurality of antibody combining sites, each immunospecific for a different antigen; e.g., a bispecific (chimeric) monoclonal antibody.

The phrase "pharmaceutically acceptable" refers to molecular entities and compositions that are physiologically tolerable and do not typically produce an allergic or similar untoward reaction, such as gastric upset, dizziness and the like, when administered to a human.

The phrase "therapeutically effective amount" is used herein to mean an amount sufficient to prevent, and preferably reduce by at least about 30 percent, more preferably by at least 50 percent, most preferably by at least 90 percent, a clinically significant change in the S phase activity of a target cellular mass, or other feature of pathology such as for example, elevated blood pressure, fever or white cell count as may attend its presence and activity.

A DNA sequence is "operatively linked" to an expression control sequence when the expression control sequence controls and regulates the transcription and translation of that DNA sequence. The term "operatively linked" includes having an appropriate start signal (e.g., ATG) in front of the DNA sequence to be expressed and maintaining the correct reading frame to permit expression of the DNA sequence under the control of the expression control sequence and production of the desired product encoded by the DNA sequence. If a gene that one desires to insert into a recombinant DNA molecule does not contain an appropriate start signal, such a start signal can be inserted in front of the gene.

The term "standard hybridization conditions" refers to salt and temperature conditions substantially equivalent to 5×SSC and 65° C. for both hybridization and wash.

In its primary aspect, the present invention relates to all members of the herein disclosed family of homeotic regulators of gene expression.

In a particular embodiment, the present invention concerns the identification of a homeoprotein regulator of insulin gene expression.

As stated above, the present invention also relates to a recombinant DNA molecule or cloned gene, or a degenerate variant thereof, which encodes a homeoprotein regulator of insulin gene expression, or a fragment thereof, that possesses a molecular weight of about 31 kD has an amino acid sequence set forth in FIGS. 1 and 2 (SEQ ID NOS:2 and 5, respectively); preferably a nucleic acid molecule, in particular a recombinant DNA molecule or cloned gene, encoding the approximately 31 kD homeoprotein regulator of insulin gene expression and has a nucleotide sequence or is complementary to a DNA sequence shown in FIGS. 1 and 2 (SEQ ID NOS:1, 3 and 5).

The possibilities both diagnostic and therapeutic that are raised by the existence of the hlomeoprotein regulator of insulin gene expression, derive from the fact that the factors appear to participate in direct and causal protein-protein interaction between the receptor that is occupied by its ligand, and those factors that thereafter directly interface with the gene and effect transcription and accordingly gene activation. As suggested earlier and elaborated further on herein, the present invention contemplates pharmaceutical intervention in the cascade of reactions in which the homeoprotein regulator of insulin gene expression is implicated, to modulate the activity initiated by the stimulus bound to the cellular receptor.

Thus, in instances where it is desired to reduce or inhibit the gene activity resulting from a particular stimulus or factor, an appropriate inhibitor of the homeoprotein regulator of insulin gene expression could be introduced to block the interaction of the homeoprotein regulator of insulin gene expression with those factors causally connected with gene activation. Correspondingly, instances where insufficient gene activation is taking place could be remedied by the introduction of additional quantities of the homeoprotein regulator of insulin gene expression or its chemical or pharmaceutical cognates, analogs, fragments and the like.

As discussed earlier, the homeoprotein regulators of insulin gene expression or their binding partners or other ligands or agents exhibiting either mimicry or antagonism to the homeoprotein regulators of insulin gene expression or control over their production, may be prepared in pharmaceutical compositions, with a suitable carrier and at a strength effective for administration by various means to a patient experiencing an adverse medical condition associated specific transcriptional stimulation for the treatment thereof. A variety of administrative techniques may be utilized, among them parenteral techniques such as subcutaneous, intravenous and intraperitoneal injections, catheterizations and the like. Average quantities of the homeoprotein regulator of insulin gene expression or their subunits may vary and in particular should be based upon the recommendations and prescription of a qualified physician or veterinarian.

Also, antibodies including both polyclonal and monoclonal antibodies, and drugs that modulate the production or activity of the homeoprotein regulator of insulin gene expression and/or their subunits may possess certain diagnostic applications and may for example, be utilized for the purpose of detecting and/or measuring conditions such as viral infection or the like. For example, the homeoprotein regulator of insulin gene expression or its subunits may be used to produce both polyclonal and monoclonal antibodies to themselves in a variety of cellular media, by known techniques such as the hybridoma technique utilizing, for example, fused mouse spleen lymphocytes and myeloma cells. Likewise, small molecules that mimic or antagonize the activity(ies) of the homeoprotein regulator of insulin gene expression of the invention may be discovered or synthesized, and may be used in diagnostic and/or therapeutic protocols.

The general methodology for making monoclonal antibodies by hybridomas is well known. Immortal, antibody-producing cell lines can also be created by techniques other than fusion, such as direct transformation of B lymphocytes with oncogenic DNA, or transfection with Epstein-Barr virus. See, e.g., M. Schreier et al., "Hybridoma Techniques" (1980); Hammerling et al., "Monoclonal Antibodies And T-cell Hybridomas" (1981); Kennett et al., "Monoclonal Antibodies" (1980); see also U.S. Pat. Nos. 4,341,761; 4,399,121; 4,427,783; 4,444,887; 4,451,570; 4,466,917; 4,472,500; 4,491,632; 4,493,890.

Panels of monoclonal antibodies produced against homeotic insulin gene expression-regulating peptides can be screened for various properties; i.e., isotype, epitope, affinity, etc. Of particular interest are monoclonal antibodies that neutralize the activity of the homeoprotein regulator of insulin gene expression or its subunits. Such monoclonals can be readily identified by their ability to inhibit the action of homeoprotein regulators of insulin gene expression in assays such as CAT assays, or electromobility shift assays (EMSAs). High affinity antibodies are also useful when immunoaffinity purification of the native or recombinant homeoprotein regulator of insulin gene expression is possible.

Preferably, the anti-homeoprotein regulator of insulin gene expression antibody used in the diagnostic methods of this invention is an affinity purified polyclonal antibody. More preferably, the antibody is a monoclonal antibody (mAb). In addition, it is preferable for the anti-homeoprotein regulator of insulin gene expression antibody molecules used herein be in the form of Fab, Fab', F(ab')$_2$ or F(v) portions of whole antibody molecules.

As suggested earlier, the diagnostic method of the present invention comprises examining a cellular sample or medium by means of an assay including an effective amount of an antagonist to a homeoprotein regulator of insulin gene expression, such as an anti-homeoprotein regulator of insulin gene expression antibody, preferably an affinity-purified polyclonal antibody, and more preferably a mAb. In addition, it is preferable for the anti-homeoprotein regulator of insulin gene expression antibody molecules used herein be in the form of Fab, Fab', F(ab')$_2$ or F(v) portions or whole antibody molecules. As previously discussed, patients capable of benefiting from this method include those suffering from diabetes of other impairment of glucose homeostasis such as hypo- or hyperglycemia, breast cancer or other like pathological derangements. Methods for isolating the homeoprotein regulator of insulin gene expression and inducing anti-homeoprotein regulator of insulin gene expression antibodies and for determining and optimizing the ability of anti-homeoprotein regulator of insulin gene expression antibodies to assist in the examination of the target cells are all well-known in the art.

Methods for producing polyclonal anti-polypeptide antibodies are well-known in the art. See U.S. Pat. No. 4,493,795 to Nestor et al. A monoclonal antibody, typically containing Fab and/or F(ab')$_2$ portions of useful antibody molecules, can be prepared using the hybridoma technology described in *Antibodies—A Laboratory Manual*, Harlow and Lane, eds., Cold Spring Harbor Laboratory, New York (1988), which is incorporated herein by reference. Briefly, to form the hybridoma from which the monoclonal antibody composition is produced, a myeloma or other self-perpetuating cell line is fused with lymphocytes obtained from the spleen of a mammal hyperimmunized with a homeoprotein regulator of insulin gene expression-binding portion thereof, or homeoprotein regulator of insulin gene expression, or an origin-specific DNA-binding portion thereof.

Splenocytes are typically fused with myeloma cells using polyethylene glycol (PEG) 6000. Fused hybrids are selected by their sensitivity to HAT. Hybridomas producing a monoclonal antibody useful in practicing this invention are identified by their ability to immunoreact with the present homeoprotein regulator of insulin gene expression and their ability to inhibit specified transcriptional activity in target cells.

A monoclonal antibody useful in practicing the present invention can be produced by initiating a monoclonal hybridoma culture comprising a nutrient medium containing a hybridoma that secretes antibody molecules of the appropriate antigen specificity. The culture is maintained under conditions and for a time period sufficient for the hybridoma to secrete the antibody molecules into the medium. The antibody-containing medium is then collected. The antibody molecules can then be further isolated by well-known techniques.

Media useful for the preparation of these compositions are both well-known in the art and commercially available and include synthetic culture media, inbred mice and the like. An exemplary synthetic medium is Dulbecco's minimal essential medium (DMEM; Dulbecco et al., *Virol.* 8: 396 (1959)) supplemented with 4.5 gm/l glucose, 20 mM glutamine, and 20% fetal calf serum. An exemplary inbred mouse strain is the Balb/c.

Methods for producing monoclonal anti-homeoprotein regulator of insulin gene expression antibodies are also well-known in the art. See Niman et al., *Proc. Natl. Acad. Sci. USA,* 80: 4949–4953 (1983). Typically, the present homeoprotein regulator of insulin gene expression or a peptide analog is used either alone or conjugated to an immunogenic carrier, as the immunogen in the before-described procedure for producing anti-homeoprotein regulator of insulin gene expression monoclonal antibodies. The hybridomas are screened for the ability to produce an antibody that immunoreacts with the homeotic insulin gene expression-regulating peptide analog and the present homeoprotein regulator of insulin gene expression.

The present invention further contemplates therapeutic compositions useful in practicing the therapeutic methods of this invention. A subject therapeutic composition includes, in admixture, a pharmaceutically acceptable excipient (carrier) and one or more of a homeoprotein regulator of insulin gene expression, polypeptide analog thereof or fragment thereof, as described herein as an active ingredient. In a preferred embodiment, the composition comprises an antigen capable of modulating the specific binding of the present homeoprotein regulator of insulin gene expression within a target cell.

The preparation of therapeutic compositions which contain polypeptides, analogs or active fragments as active ingredients is well understood in the art. Typically, such compositions are prepared as injectables, either as liquid solutions or suspensions, however, solid forms suitable for solution in, or suspension in, liquid prior to injection can also be prepared. The preparation can also be emulsified. The active therapeutic ingredient is often mixed with excipients which are pharmaceutically acceptable and compatible with the active ingredient. Suitable excipients are, for example, water, saline, dextrose, glycerol, ethanol, or the like and combinations thereof. In addition, if desired, the composition can contain minor amounts of auxiliary substances such as wetting or emulsifying agents, pH buffering agents which enhance the effectiveness of the active ingredient.

A polypeptide, analog or active fragment can be formulated into the therapeutic composition as neutralized pharmaceutically acceptable salt forms. Pharmaceutically acceptable salts include the acid addition salts (formed with the free amino groups of the polypeptide or antibody molecule) and which are formed with inorganic acids such as, for example, hydrochloric or phosphoric acids, or such organic acids as acetic, oxalic, tartaric, mandelic, and the like. Salts formed from the free carboxyl groups can also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

The therapeutic polypeptide-, analog- or active fragment-containing compositions are conventionally administered intravenously, as by injection of a unit dose, for example. The term "unit dose" when used in reference to a therapeutic composition of the present invention refers to physically discrete units suitable as unitary dosage for humans, each unit containing a predetermined quantity of active material calculated to produce the desired therapeutic effect in association with the required diluent; i.e., carrier, or vehicle.

The compositions are administered in a manner compatible with the dosage formulation, and in a therapeutically effective amount. The quantity to be administered depends on the subject to be treated, capacity of the subject's immune system to utilize the active ingredient, and degree of inhibition or neutralization of homeoprotein regulator of insulin gene expression binding capacity desired. Precise amounts of active ingredient required to be administered depend on the judgment of the practitioner and are peculiar to each individual. However, suitable dosages may range from about 0.1 to 20, preferably about 0.5 to about 10, and more preferably one to several, milligrams of active ingredient per kilogram body weight of individual per day and depend on the route of administration. Suitable regimes for initial administration and booster shots are also variable, but are typified by an initial administration followed by repeated doses at one or more hour intervals by a subsequent injection or other administration. Alternatively, continuous intravenous infusion sufficient to maintain concentrations of ten nanomolar to ten micromolar in the blood are contemplated.

The therapeutic compositions may further include an effective amount of the homeoprotein regulator of insulin gene expression/insulin promoter antagonist or analog thereof, and one or more of the following active ingredients: an antibiotic, a steroid. Exemplary formulations are given below:

| Ingredient | mg/ml |
|---|---|
| Intravenous Formulation I | |
| cefotaxime | 250.0 |
| homeoprotein regulator of insulin gene expression | 10.0 |
| dextrose USP | 45.0 |
| sodium bisulfite USP | 3.2 |
| edetate disodium USP | 0.1 |
| water for injection q.s.a.d. | 1.0 ml |
| Intravenous Formulation II | |
| ampicillin | 250.0 |
| homeoprotein regulator of insulin gene expression | 10.0 |
| sodium bisulfite USP | 3.2 |
| disodium edetate USP | 0.1 |
| water for injection q.s.a.d. | 1.0 ml |
| Intravenous Formulation III | |
| gentamicin (charged as sulfate) | 40.0 |
| homeoprotein regulator of insulin gene expression | 10.0 |
| sodium bisulfite USP | 3.2 |
| disodium edetate USP | 0.1 |
| water for injection q.s.a.d. | 1.0 ml |
| Intravenous Formulation IV | |
| homeoprotein regulator of insulin gene expression | 10.0 |
| dextrose USP | 45.0 |
| sodium bisulfite USP | 3.2 |
| edetate disodium USP | 0.1 |
| water for injection q.s.a.d. | 1.0 ml |
| Intravenous Formulation V | |
| homeoprotein regulator of insulin gene expression antagonist | 5.0 |
| sodium bisulfite USP | 3.2 |
| disodium edetate USP | 0.1 |
| water for injection q.s.a.d. | 1.0 ml |

As used herein, "pg" means picogram, "ng" means nanogram, "ug" or "$\mu g$" mean microgram, "mg" means milligram, "ul" or "$\mu l$" mean microliter, "ml" means milliliter, "l" means liter.

Another feature of this invention is the expression of the DNA sequences disclosed herein. As is well known in the art, DNA sequences may be expressed by operatively linking them to an expression control sequence in an appropriate expression vector and employing that expression vector to transform an appropriate unicellular host.

Such operative linking of a DNA sequence of this invention to an expression control sequence, of course, includes, if not already part of the DNA sequence, the provision of an initiation codon, ATG, in the correct reading frame upstream of the DNA sequence.

A wide variety of host/expression vector combinations may be employed in expressing the DNA sequences of this invention. Useful expression vectors, for example, may consist of segments of chromosomal, non-chromosomal and Synthetic DNA sequences. Suitable vectors include derivatives of SV40 and known bacterial plasmids, e.g., E. coli plasmids col E1, pCR1, pBR322, pMB9 and their derivatives, plasmids such as RP4; phage DNAS, e.g., the numerous derivatives of phage λ, e.g., NM989, and other phage DNA, e.g., M13 and Filamentous single stranded phage DNA; yeast plasmids such as the $2\mu$ plasmid or derivatives thereof; vectors useful in eukaryotic cells, such as vectors useful in insect or mammalian cells; vectors derived from combinations of plasmids and phage DNAS, such as plasmids that have been modified to employ phage DNA or other expression control sequences; and the like.

Any of a wide variety of expression control sequences—sequences that control the expression of a DNA sequence operatively linked to it—may be used in these vectors to express the DNA sequences of this invention. Such useful expression control sequences include, for example, the early or late promoters of SV40, CMV, vaccinia, polyoma or adenovirus, the lac system, the trp system, the TAC system, the TRC system, the LTR system, the Inajor operator and promoter regions of phage λ, the control regions of fd coat protein, the promoter for 3-phosphoglycerate kinase or other glycolytic enzymes, the promoters of acid phosphatase (e.g., Pho5), the promoters of the yeast (α-mating factors, and other sequences known to control the expression of genes of prokaryotic or eukaryotic cells or their viruses, and various combinations thereof.

A wide variety of unicellular host cells are also useful in expressing the DNA sequences of this invention. These hosts may include well known eukaryotic and prokaryotic hosts, such as strains of E. coli, Pseudomonas, Bacillus, Streptoinyces, fungi such as yeasts, and animal cells, such as CHO, R1.1, B-W and L-M cells, African Green Monkey kidney cells (e.g., COS 1, COS 7, BSC1, BSC40, and BMT10), insect cells (e.g., Sf9), and human cells and plant cells in tissue culture.

It will be understood that not all vectors, expression control sequences and hosts will function equally well to express the DNA sequences of this invention. Neither will all hosts function equally well with the same expression system. However, one skilled in the art will be able to select the proper vectors, expression control sequences, and hosts without undue experimentation to accomplish the desired expression without departing from the scope of this invention. For example, in selecting a vector, the host must be considered because the vector must function in it. The vector's copy number, the ability to control that copy number, and the expression of any other proteins encoded by the vector, such as antibiotic markers, will also be considered.

In selecting an expression control sequence, a variety of factors will normally be considered. These include, for example, the relative strength of the system, its controllability, and its compatibility with the particular DNA sequence or gene to be expressed, particularly as regards potential secondary structures. Suitable unicellular hosts will be selected by consideration of, e.g., their compatibility with the chosen vector, their secretion characteristics, their ability to fold proteins correctly, and their fermentation requirements, as well as the toxicity to the host of the product encoded by the DNA sequences to be expressed, and the ease of purification of the expression products.

Considering these and other factors a person skilled in the art will be able to construct a variety of vector/expression control sequence/lost combinations that will express the DNA sequences of this invention on fermentation or in large scale animal culture.

It is further intended that the homeoprotein regulator of insulin gene expression analogs may be prepared from nucleotide sequences of the protein complex/subunit derived within the scope of the present invention. Analogs, such as fragments, may be produced, for example, by pepsin digestion of the homeoprotein material. Other analogs, such as muteins, can be produced by standard site-directed mutagenesis of homeoprotein regulator of insulin gene expression coding sequences. Analogs exhibiting "insulin gene expression-regulating activity" such as small molecules, whether functioning as promoters or inhibitors, may be identified by known in vivo and/or in vitro assays.

As mentioned above, a DNA sequence encoding a homeoprotein regulator of insulin gene expression can be prepared synthetically rather than cloned. The DNA sequence can be designed with the appropriate codons for the homeoprotein regulator of insulin gene expression amino acid sequence. In general, one will select preferred codons for the intended host if the sequence will be used for expression. The complete sequence is assembled from overlapping oligonucleotides prepared by standard methods and assembled into a complete coding sequence. See, e.g., Edge, Nature, 292: 756 (1981); Nambair et al., Science, 223: 1299 (1984); Jay et al., J. Biol. Chem., 259: 6311 (1984).

Synthetic DNA sequences allow convenient construction of genes which will express homeotic insulin gene expression-regulator analogs or "muteins". Alternatively, DNA encoding muteins can be made by site-directed mutagenesis of native homeoprotein regulator of insulin gene expression genes or cDNAs, and muteins can be made directly using conventional polypeptide synthesis.

A general method for site-specific incorporation of unnatural amino acids into proteins is described in Christopher J. Noren, Spencer J. Anthony-Cahill, Michael C. Griffith, Peter G. Schultz, Science, 244: 182–188 (April 1989). This method may be used to create analogs with unnatural amino acids.

The present invention extends to the preparation of antisense nucleotides and ribozymes that may be used to interfere with the expression of the homeoprotein regulator of insulin gene expression at the translational level. This approach utilizes antisense nucleic acid and ribozymes to block translation of a specific mRNA, either by masking that mRNA with an antisense nucleic acid or cleaving it with a ribozyme.

Antisense nucleic acids are DNA or RNA molecules that are complementary to at least a portion of a specific mRNA molecule. (See Weintraub, 1990; Marcus-Sekura, 1988.) In the cell, they hybridize to that mRNA, forming a double stranded molecule. The cell does not translate an mRNA in this double-stranded form.

Therefore, antisense nucleic acids interfere with the expression of mRNA into protein. Oligomers of about fifteen nucleotides and molecules that hybridize to the AUG initiation codon will be particularly efficient, since they are easy to synthesize and are likely to pose fewer problems than larger molecules when introducing them into homeoprotein regulator of insulin gene expression-producing cells. Antisense methods have been used to inhibit the expression of many genes in vitro (Marcus-Sekura, 1988; Hambor et al., 1988).

Ribozymes are RNA molecules possessing the ability to specifically cleave other single stranded RNA molecules in a manner somewhat analogous to DNA restriction endonucleases. Ribozymes were discovered from the observation that certain mRNAs have the ability to excise their own introns. By modifying the nucleotide sequence of these RNAs, researchers have been able to engineer molecules that recognize specific nucleotide sequences in an RNA molecule and cleave it (Cech, 1988.). Because they are sequence-specific, only mRNAs with particular sequences are inactivated.

Investigators have identified two types of ribozymes, Tetrahymena-type and "hammerhead"-type. (Hasselhoff and Gerlachi, 1988) Tetrahymena-type ribozymes recognize four-base sequences, while "hammerhead"-type recognize eleven- to eighteen-base sequences. The longer the recognition sequence, the more likely it is to occur exclusively in the target mRNA species. Therefore, hammerhead-type ribozymes are preferable to Tetrahymena-type ribozymes for inactivating a specific mRNA species, and eighteen base recognition sequences are preferable to shorter recognition sequences.

The DNA sequences described herein may thus be used to prepare antisense molecules against, and ribozymes that cleave mRNAs for homeoprotein regulator of insulin gene expression and their ligands.

The present invention also relates to a variety of diagnostic applications, including methods for detecting the presence of stimuli such as the earlier referenced polypeptide ligands, by reference to their ability to elicit the activities which are mediated by the present homeoprotein regulator of insulin gene expression. As mentioned earlier, the homeoprotein regulator of insulin gene expression can be used to produce antibodies to itself by a variety of known techniques, and such antibodies could then be isolated and utilized as in tests for the presence of particular transcriptional activity in suspect target cells.

As described in detail above, antibody(ies) to the homeoprotein regulator of insulin gene expression can be produced and isolated by standard methods including the well known hybridoma techniques. For convenience, the antibody(ies) to the homeoprotein regulator of insulin gene expression will be referred to herein as $Ab_1$ and antibody (ies) raised in another species as $Ab_2$.

The presence of homeoprotein regulator of insulin gene expression in cells can be ascertained by the usual immunological procedures applicable to such determinations. A number of useful procedures are known. Three such procedures which are especially useful utilize either the homeoprotein regulator of insulin gene expression labeled with a detectable label, antibody $Ab_1$ labeled with a detectable label, or antibody $Ab_2$ labeled with a detectable label. The procedures may be summarized by the following equations wherein the asterisk indicates that the particle is labeled, and "HRIGE" stands for the homeoprotein regulator of insulin gene expression:

HRIGE*+$Ab_1$=HRIGE*$Ab_1$      A.

HRIGE+Ab*=HRIGE$Ab_1$*      B.

HRIGE+$Ab_1$+$Ab_2$*=HRIGE$Ab_1Ab_2$*      C.

The procedures and their application are all familiar to those skilled in the art and accordingly may be utilized within the scope of the present invention. The "competitive" procedure, Procedure A, is described in U.S. Pat. Nos. 3,654,090 and 3,850,752. Procedure C, the "sandwich" procedure, is described in U.S. Pat. Nos. RE 31,006 and 4,016,043. Still other procedures are known such as the "double antibody", or "DASP" procedure.

In each instance, the homeoprotein regulator of insulin gene expression forms complexes with one or more antibody (ies) or binding partners and one member of the complex is labeled with a detectable label. The fact that a complex has formed and, if desired, the amount thereof, can be determined by known methods applicable to the detection of labels.

It will be seen from the above, that a characteristic property of $Ab_2$ is that it will react with $Ab_1$. This is because $Ab_1$ raised in one mammalian species has been used in another species as an antigen to raise the antibody $Ab_2$. For example, $Ab_2$ may be raised in goats using rabbit antibodies as antigens. $Ab_2$ therefore would be anti-rabbit antibody raised in goats. For purposes of this description and claims, $Ab_1$ will be referred to as a primary or anti-homeoprotein regulator of insulin gene expression antibody, and $Ab_2$ will be referred to as a secondary or anti-$Ab_1$ antibody.

The labels most commonly employed for these studies are radioactive elements, enzymes, chemicals which fluoresce when exposed to ultraviolet light, and others.

A number of fluorescent materials are known and can be utilized as labels. These include, for example, fluorescein, rhodamine, auramine, Texas Red, AMCA blue and Lucifer Yellow. A particular detecting material is anti-rabbit antibody prepared in goats and conjugated with fluorescein through an isothiocyanate.

The homeoprotein regulator of insulin gene expression or its binding partner(s) can also be labeled with a radioactive element or with an enzyme. The radioactive label can be detected by any of the currently available counting procedures. The preferred isotope may be selected from $^3H$, $^{14}C$, $^{32}P$, $^{35}S$, $^{36}Cl$, $^{51}Cr$, $^{57}Co$, $^{58}Co$, $^{59}Fe$, $^{90}Y$, $^{125}I$, $^{131}I$, and $^{186}Re$.

Enzyme labels are likewise useful, and can be detected by any of the presently utilized calorimetric, spectrophotometric, fluorospectrophotometric, amperometric or gasometric techniques. The enzyme is conjugated to the selected particle by reaction with bridging molecules such as carbodiumides, diisocyanates, glutaraldehyde and the like. Many enzymes which can be used in these procedures are known and can be utilized. The preferred are peroxidase, β-glucuronidase, β-D-glucosidase, β-D-galactosidase, urease, glucose oxidase plus peroxidase and alkaline phosphatase. U.S. Pat. Nos. 3,654,090; 3,850,752; and 4,016,043 are referred to by way of example for their disclosure of alternate labeling material and methods.

A particular assay system developed and utilized in accordance with the present invention, is known as a receptor assay. In a receptor assay, the material to be assayed is appropriately labeled and then certain cellular test colonies are inoculated with a quantity of both the labeled and unlabeled material after which binding studies are conducted to determine the extent to which the labeled material binds to the cell receptors. In this way, differences in affinity between materials can be ascertained.

Accordingly, a purified quantity of the homeoprotein regulator of insulin gene expression may be radiolabeled and combined, for example, with antibodies or other inhibitors thereto, after which binding studies would be carried out. Solutions would then be prepared that contain various quantities of labeled and unlabeled uncombined homeoprotein regulator of insulin gene expression, and cell samples would then be inoculated and thereafter incubated. The resulting cell monolayers are then washed, solubilized and then counted in a gamma counter for a length of time sufficient to yield a standard error of <5%. These data are then subjected to Scatchard analysis after which observations and conclusions regarding material activity can be drawn. While the foregoing is exemplary, it illustrates the manner in which a receptor assay may be performed and utilized, in the instance where the cellular binding ability of the assayed material may serve as a distinguishing characteristic.

An assay useful and contemplated in accordance with the present invention is known as a "cis/trans" assay. Briefly, this assay employs two genetic constructs, one of which is typically a plasmid that continually expresses a particular receptor of interest when transfected into an appropriate cell line, and the second of which is a plasmid that expresses a reporter such as luciferase, under the control of a receptor/ligand complex. Thus, for example, if it is desired to evaluate a compound as a ligand for a particular receptor, one of the plasmids would be a construct that results in expression of the receptor in the chosen cell line, while the second plasmid would possess a promoter linked to the luciferase gene in which the response element to the particular receptor is inserted. If the compound under test is an agonist for the receptor, the ligand will complex with the receptor, and the resulting complex will bind the response element and initiate transcription of the luciferase gene. The resulting chemiluminescenice is then measured photometrically, and dose response curves are obtained and compared to those of known ligands. The foregoing protocol is described in detail in U.S. Pat. No. 4,981,784 and PCT International Publication No. WO 88/03168, for which purpose the artisan is referred.

In a further embodiment of this invention, commercial test kits suitable for use by a medical specialist may be prepared to determine the presence or absence of predetermined transcriptional activity or predetermined transcriptional activity capability in suspected target cells. In accordance with the testing techniques discussed above, one class of such kits will contain at least the labeled homeoprotein regulator of insulin gene expression or its binding partner, for instance an antibody specific thereto, and directions, of course, depending upon the method selected, e.g., "competitive", "sandwich", "DASP" and the like. The kits may also contain peripheral reagents such as buffers, stabilizers, etc.

Accordingly, a test kit may be prepared for the demonstration of the presence or capability of cells for predetermined transcriptional activity, comprising:

(a) a predetermined amount of at least one labeled immunochemically reactive component obtained by the direct or indirect attachment of the present lhomeoprotein regulator of insulin gene expression factor or a specific binding partner thereto, to a detectable label;

(b) other reagents; and (c) directions for use of said kit.

More specifically, the diagnostic test kit may comprise:

(a) a known amount of the homeoprotein regulator of insulin gene expression as described above (or a binding partner) generally bound to a solid phase to form an immunosorbent, or in the alternative, bound to a suitable tag, or plural such end products, etc. (or their binding partners) one of each;

(b) if necessary, other reagents; and (c) directions for use of said test kit.

In a further variation, the test kit may be prepared and used for the purposes stated above, which operates according to a predetermined protocol (e.g. "competitive", "sandwich", "double antibody", etc.), and comprises:

(a) a labeled component which has been obtained by coupling the homeoprotein regulator of insulin gene expression to a detectable label;

(b) one or more additional immunochemical reagents of which at least one reagent is a ligand or an immobilized ligand, which ligand is selected from the group consisting of:

(i) a ligand capable of binding with the labeled component (a);

(ii) a ligand capable of binding with a binding partner of the labeled component (a);

(iii) a ligand capable of binding with at least one of the component(s) to be determined; and (iv) a ligand capable of binding with at least one of the binding partners of at least one of the component(s) to be determined; and (c) directions for the performance of a protocol for the detection and/or determination of one or more components of an immunochemical reaction between the homeoprotein regulator of insulin gene expression and a specific binding partner thereto.

In accordance with the above, an assay system for screening potential drugs effective to modulate the activity of the homeoprotein regulator of insulin gene expression may be prepared. The homeoprotein regulator of insulin gene expression may be introduced into a test system, and the prospective drug may also be introduced into the resulting cell culture, and the culture thereafter examined to observe any changes in the transcriptional activity of the cells, due either to the addition of the prospective drug alone, or due to the effect of added quantities of the known homeoprotein regulator of insulin gene expression.

The following examples are presented in order to more fully illustrate the preferred embodiments of the invention. They should in no way be construed, however, as limiting the broad scope of the invention.

EXAMPLES

The following is a list of primers used in the Examples, some of which are specifically listed within a particular Example:

| | | | |
|---|---|---|---|
| GCIX-1 | 5' | GCGACATGACTCCCTGT 3' | (SEQ ID NO:6) |
| GCIX-2 | 5' | AGACTGGTAACTGTCC 3' | (SEQ ID NO:7) |
| GCIX-3 | 5' | TTAACGACGTTGGGTATG 3' | (SEQ ID NO:8) |
| GCIX-4 | 5' | CCTATGTACAGGAAATAG 3' | (SEQ ID NO:9) |
| GCIX-5 | 5' | GTTGACAGCAGGCATCAG 3' | (SEQ ID NO:10) |
| CIXSOME-1 | 5' | GGTACCTGCAAATGCTGCCTTCCA 3' | (SEQ ID NO:11) |
| CIXSOME-2 | 5' | TGGGGAGAGCGAGCTGAGTGC 3' | (SEQ ID NO:12) |
| HGCIX-6 | 5' | GGGGAATCCAAAGCGTT 3' | (SEQ ID NO:13) |
| HGCIX-7 | 5' | AAACGCTTTGGATTCCC 3' | (SEQ ID NO:14) |
| HGCIX-8 | 5' | AGAAGGTTCTCGCCAAG 3' | (SEQ ID NO:15) |
| HGCIX-9 | 5' | TCTGAAACCAGATGGTA 3' | (SEQ ID NO:16) |
| HGCIX-10 | 5' | GGGTAAAGTATTTTCGC 3' | (SEQ ID NO:17) |
| HGCIX-11 | 5' | AGGTGCACACAGGTCAC 3' | (SEQ ID NO:18) |
| HGCIX-12 | 5' | AAGGAGGTCTGAGTAGC 3' | (SEQ ID NO:19) |
| HGCIX-13 | 5' | CTGATGCCTGCTGTCAAC 3' | (SEQ ID NO:20) |
| HGCIX-14 | 5' | GATATCCCGGATAGAAGG 3' | (SEQ ID NO:21) |
| HGCIX-15 | 5' | CCTTCTATCCGGGATATC 3' | (SEQ ID NO:22) |
| HGCIX-16 | 5' | CATATGTCACGGCTGCAG 3' | (SEQ ID NO:23) |
| HGCIX-17 | 5' | CTGCAGCCGTGACATATG 3' | (SEQ ID NO:24) |
| HGCIX-18 | 5' | CCAGTTTGCAGAGTCTCA 3' | (SEQ ID NO:25) |
| HGCIX-19 | 5' | CATCTGGTTTCAGAACCG 3' | (SEQ ID NO:26) |
| ISL3-5 | 5' | CGAGTATCCAGGAGCTCACTG 3' | (SEQ ID NO:27) |
| ISL3-A | 5' | GGTCTTGACCTTGGCAAGAAC 3' | (SEQ ID NO:28) |
| ISL3-22 | 5' | GGATATCGAAGGCTTGCA 3' | (SEQ ID NO:29) |
| ISL3-21 | 5' | TAAGTAGCCAGGGTGGCC 3' | (SEQ ID NO:30) |
| CST-GGGS | 5' | GCCGGATCCGAGGCGGGTACTACTCTTGC 3' | (SEQ ID NO:31) |
| GST-FRRA | 5' | GCCGGATCCTCAGCGGCGGAAGGCGCAGCC 3' | (SEQ ID NO:32) |
| GAL/ISL3-1 | 5' | GGCGGATCCATGGAGCCCGGCAAT 3' | (SEQ ID NO:33) |
| GAL/ISL3-2 | 5' | GGCGGATCCATGCCGACTGTCAAC 3' | (SEQ ID NO:34) |
| GAL/ISL3-3 | 5' | GGCGGATCCATGGCTCCTGTGCCTTATGGC 3' | (SEQ ID NO:35) |
| GAL/ISL3-4 | 5' | GGCGGATCCATGTCGGAAACCCCTGCACCT 3' | (SEQ ID NO:36) |

Example 1

Cloning of Full-length Rat cDNA Encoding HoxB13 Protein

To isolate factors that might regulate insulin expression in Tu6 cells, degenerate sense and antisense oligos corresponding to the most conserved regions of the homeodomain, amino acids 16–20 (LEKEF) (SEQ ID NO:37) and amino acids 47–51 (IWFQN) (SEQ ID NO:38) of the homeobox, respectively. Using these primers for PCR amplification of sequences in a Tu6 cDNA library, a fragment of the predicted size was obtained, subcloned into the plasmid Bluescript SK II(+) (Stratagene, La Jolla, Calif.). Five of the recombinant clones corresponded to a fragment of STF-1 (Leonard et al, 1993, *Mol. Endocrinol.* 7: 1275). One clone contained a distinct, novel sequence corresponding to the subject of this application. The presumptive gene corresponding to this fragment was initially termed Isl-3, then CIX-1, then ultimately HoxB13 (see below). This fragment was used to screen a Tu6 cDNA library. Of the 500,000 plaques screened, one positive clone was obtained which contained a 3.2 kb insert. A 1.2 kb Eco RI subfragment of this insert was subcloned into pGEM-3Z(f-) (Promega, Madison, Wis.), and the resultant plasmid was termed plsl-3(1.2). DNA sequencing revealed that this fragment encoded the C-terminal 200 amino acids of HoxB13.

$10^6$ pfu of phage λ constituting a Tu6 library were added to Y1090 cells at 37° C. for 30 minutes and plated in 10 ml top agarose onto 17 dishes containing LB agar. Filters were lifted from each dish and denatured using a standard protocol. Filters were air dried for 3- to 60 minutes and DNA was immobilized using a Stratalinker 2400 (Stratagene, La Jolla, Calif.) in autocrosslink mode. Filters were prehybridized at 65° C. for 1 to 2 hours using about 100 ml Churclh/Gilbert buffer (0.5M NaHPO$_4$, pH 7.2, 7% SDS, 1 mM EDTA and 1% BSA (fraction V)). A 400 kb Not I fragment, corresponding to the 5'-most region of the 1.2 kb rat cDNA clone (pIsl-3(1.2)) was denatured at 95° C. for 2 minutes and placed on ice, and then labelled by random priming with α-$^{32}$-P-dCTP and Klenow at 37° C. for 30 minutes. The Klenow was inactivated at 65° C. for 15 minutes, and the probed ethanol precipitated in 3M NaOAc. Analysis by Geiger counter indicated approximately 50% incorporation.

The probe was resuspended in 500 μl H$_2$O, denatured at 100° C. for 2 minutes and placed on ice. Filters were immersed individually in 45 ml hybridization buffer and prehybridized at 65° C., and the probe was added overnight. Filters were washed twice quickly in 2×SSC/0.1% SDS at room temperature, three times in 0.2×SSC/0.1% SDS at 65° C., and then once for twenty minutes in 0.2×SSC/0.1% SDS at 65° C. Filters were exposed to film approximately 5 hours and 4 positives were picked and eluted 1 hour in 500 μl SM buffer with rocking. 2 μl of a 1:10 and 1:100 dilution were added to fresh competent Y1090 cells and plated. Four positives were picked and eluted into 100 μl SM and 90 μl was plated for amplification. 5 μl of the amplified material from each (Isl-3.2-1a, 1b, 2, 3) was plated. 50 μl of the amplified SM stocks were used to grow Isl-3.2 plaques for phage preps. Plates were overlayed with 8 ml λ diluent (10 mM Tris, pH 8.0), 2 mM MgCl$_2$) overnight at 4° C.

Minipreps were prepared using standard protocols and digested with Not I. Half of the digest was run on a 0.8% agarose analytical gel and half was saved for ligation. Clones 1a and 3 gave bands of about 800 kb and 700 kb. 10 μg pIsl-3(1.2) was digested with Not I and vector was isolated for overnight ligation at 16° C. to the digested inserts. Ligations were used to transform XL1-blue competent cells (Stratagene) overnight at 37° C. 20 colonies were picked and grown 6 hours at 37° C. Boiling minipreps were prepared and digested with Not I overnight at 37° C. The digested phage DNA was ligated to freshly isolated SK II which was digested with Not I and phosphatased, overnight at 16° C.

One positive clone was obtained, whose insert was approximately 1.6 kb in size. The entire Eco RI fragment was cloned into Bluescript SK II(+), yielding the plasmid SK/B13. The sequenced region of the insert is shown in FIG. 1. This cDNA contains one large open reading frame which is predicted to encode a protein of 287 amino acids. Nucleic acid and protein databases were searched with this sequence, and the homeodomain of HoxA13, HoxC13 and HoxD13 were identified as highly homologous to the insert in SK/B13 (FIG. 8). Because the chromosomal location of the human homologue for this sequence is in the HoxB complex, the gene was termed HoxB13.

Example 2

Cloning of Genomic HoxB13 Sequence

An HL1067j genomic library (Clontech, Palo Alto, Calif.) was titered in K802 competent cells to be approximately 10$^{10}$ pfu/ml. 40 plates were then prepared using 50,000 pfu/plate. The plates wee blotted and hybridized with Isl-3 (1–286). Positive plagues were eluted in 500 ml SM, and replated in 2 ml of a 10$^{-2}$ or 10$^{-3}$ dilution. Blots were again made and hybridized to Isl-3 (1–286), positive plaques were eluted and 500 μl K802 competent cells were infected with 250 μl of the elution, and plated. 8 ml of SM was added to each plate and eluted overnight at 4° C. The SM elution was titered and 10$^7$–10$^8$ pfu was plated grown 7 hours and again eluted with 8 ml diluent overnight at 4° C. Phage DNA was prepared using standard methods, and sequenced using T3 and T7 primers, GCIX-1-5 or HGCIX primers, as follows:

| | | |
|---|---|---|
| GCIX-1 | 5' GCGACATGACTCCCTGT 3' | (SEQ ID NO:6) |
| GCIX-2 | 5' AGACTGGTAACTGTCC 3' | (SEQ ID NO:7) |
| GCIX-3 | 5' TTAACGACGTTGGGTATG 3' | (SEQ ID NO:8) |
| GCIX-4 | 5' GTTGACAGCAGGCATCAG 3' | (SEQ ID NO:9) |
| GCIX-5 | 5' GTTGACAGCAGGCATCAG 3' | (SEQ ID NO:10) |

As a result of the screen, four plaque-purified positive clones were identified. DNAs from these clones were digested with Sac I, Eco RI or Sal I, transferred to nitrocellulose, and probed with 5' or 3' cDNA fragments. One clone contained fragments which hybridized to both probes, indicating that it might contain the entire gene. Three contiguous Sac I fragments were cloned into Bluescript SK II(+). DNA sequence analysis with T3 and T7 primers (and primers having SEQ ID NOS:6–26) permitted deduction of the approximately 3 kb human HoxB13 genomic sequence shown in FIG. 2A. A candidate for the TATA box is underlined, as is the Homeodomain. Of the 287 amino acids encoded by rat HoxB13, 267 are conserved in the human gene (93% sequence identity).

Example 3

HoxB13 is Preferentially Expressed in Insulin-Producing Cells

The following is a list of cell lines used in the studies below:

| | |
|---|---|
| HIT | hamster insulinoma |
| Tu6 | subclone of liver metastasis of rat insulinoma |
| RIN | rat insulinoma |
| αTC | mouse glucagonoma |
| STC | mouse secretin/glucagon expressing line from intestinal tumor |
| PC12 | rat pheochromocytoma |
| AR42J | rat exocrine pancreatic tumor |
| R33 | retinal cell line |
| HeLa | human cervical carcinoma |
| JEG | human choriocarcinoma |
| F9 | mouse embryonal carcinoma |
| MMEC | mouse mammary epithelial cells |
| T1/Pr1 | mouse mammary tumor from in vivo-passaged, ras-transfected MMEC cells |

FIG. 3 shows an RNA analysis (Northern blot) of various cell lines probed with Isl-3. 10 μg of each RNA was run on a 1% agarose/formaldehyde gel at 150V for 2¾ hours. The gels were transferred overnight onto Hybond-N$^+$ membrane. An Isl-3 probe was prepared by digesting pIsl-3 (1.2) with Not I, to liberate a fragment which is immediately 5' to the homeodomain. Digests were run on a 0.8% agarose gel (low melting), and the appropriate bands were electroeluted. Bands electroeluted onto membrane were heated at 70° C. for 2–3 minutes, followed by addition of ⅒ volume of 5M NaCl. Phenol was added to the tubes, mixed and incubated for 5 minutes at room temperature, followed by microcentrifugation at 4° C. for 10 minutes. This mixture was extracted twice with phenol/chloroform, ethanol precipitated and resuspended in 15 μl H$_2$O.

The fragments were labelled by random priming. Membranes were prehybridized for 30 minutes, and hybridized with 10⁶ cpm/ml in Amersham rapid hybridization buffer (Arlington Heights, Ill.). Membranes were washed twice for 10 minutes in @×SSC/0.1% SDS at room temperature, and twice for 20 minutes in 0.2×SSC/0.1% SDS at 65° C. A 3-day exposure shows expression of a predominant band at 1.5 kb. The expression of HoxB13 is similar to that of STF-1. Results show HoxB13 only in two insulin-producing cell lines (Tu6 and RIN).

Example 4

Bacterially-expressed HoxB13 Protein Binds the Functionally important FLAT Element of the Insulin Promoter In order to prepare a full-length HoxB13 fragment for insertion into pGEX3X, PCR was performed on the Isl-3 (1.6 kb) clone using the following primers:

GST-ISL1:
5'GGCGGATCCCCATGGAGCCCGGCAAT3'(SEQ ID NO:39)

GST-ISL2: 5'GCCGGATCCTCACGGAGTAGTGCT3' (SEQ ID NO:40)

which were designed to permit the in-frame insertion of HoxB13 into the GST expression plasmid pGEX-3X. The resultant plasmid was transformed into protease-deficient BL21 cells, bacterial culture s were grown to log phase, and recombinant protein expression was induced with 0.4 mM IPTG. Bacterial extracts were passed over a glutathione-Sepharose column to permit binding of the GST-B13 fusion o protein to the glutathione moiety, then washed extensively. HoxB13 protein was then liberated by cleavage with factor Xa. Purified HoxB13 protein was then used in gel shift assays to test for specific binding to the FLAT element of the insulin promoter.

Gel shift assays indicated that HoxB13 binds the functionally critical FLAT element of both rat insulin promoters with high affinity. Briefly, synthetic, double-stranded FLAT element-containing fragment was created by annealing the primers:

FLAT-S 5' GATCCCCTTGTTAATAATCTAATTACCCTAGG 3' (SEQ ID NO:41)

FLAT-1 5' GATCCCTAGGGTAATTAGATTATTAACAAGGG 3' (SEQ ID NO:42).

100 μ of FLAT-S and FLAT-A were annealed in 0.1M NaCl at 85° C. for 2 minutes, 65° C. for 10 minutes, 37° C. for 10 minutes, and room temperature for 5 minutes. The ends were filled in with Klenow at 30° C. for 20–30 minutes and the double-stranded DNA precipitated with NaOAc and 70% ethanol.

Figure 4:
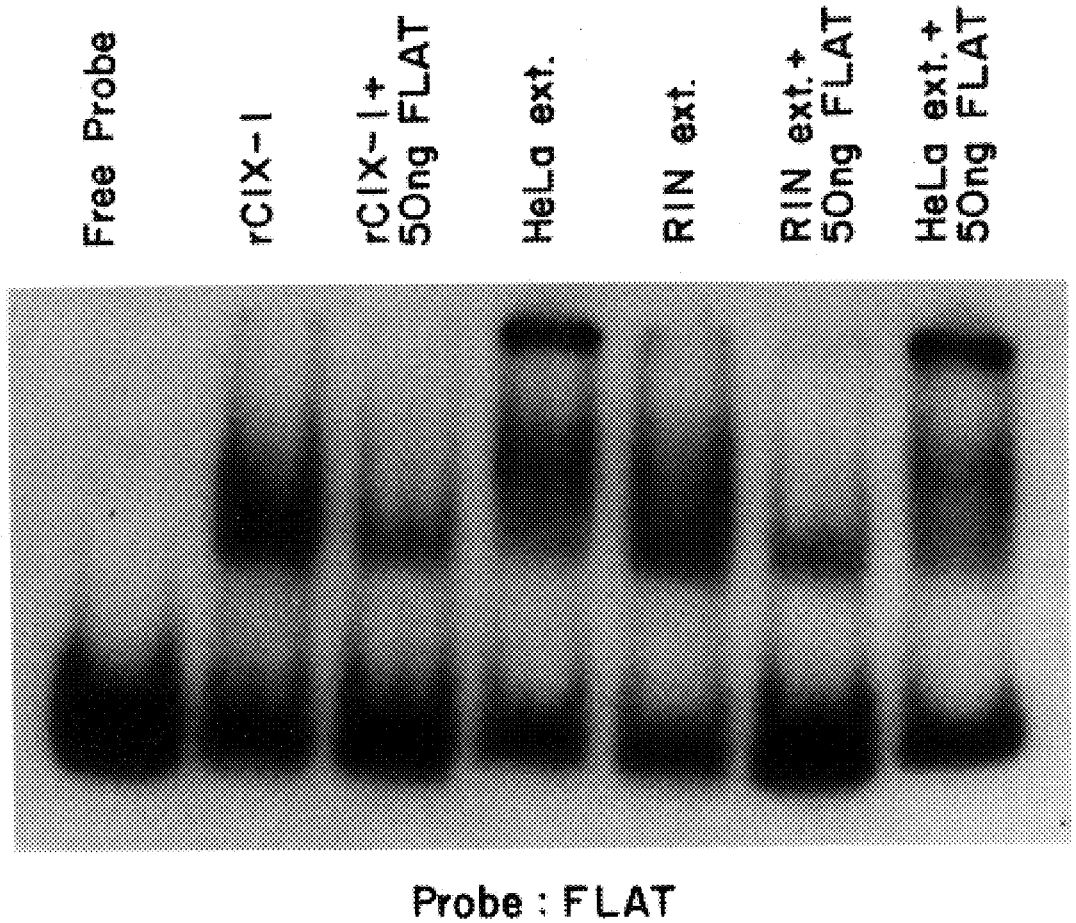
FIG. 4 is an electromobility shift assay (EMSA) which demonstrates that recombinant, purified HoxB13 binds FLAT element with high affinity.

For gel shift assays, the labeled fragment was incubated 15 minutes at room temperature with buffer alone (50 mM KCI, 20 mM HEPES pH 7.8, 1 mM EDTA, 20% glycerol, 1 mM DTt and 1 mM PMSF), 1 μl bacterially expressed HoxB13 (see Example 3; "rCIX-1" in FIG. 4), 1 μl HoxB13 and 50 ng unlabeled FLAT DNA ("rCIX-1+50 ng FLAT" in FIG. 4), 5 μg Hela cell nuclear extract, 5 μg RIN cell nuclear extract, 5 μg RIN extract and 50 ng FLAT, 5 μg HeLa extract and 50 ng FLAT (respectively, as shown in FIG. 4). The samples were then run on a 5% acrylamide gel in 0.5× TBE.

FIG. 4 shows that HoxB13 protein binds the FLAT probe with specificity, since the binding can be competed by coincubation with excess unlabeled FLAT DNA. Additionally, insulin-producing RIN cells, but not HeLa cells, contain a FLAT-binding species which shifts the probe similarly to HoxB13 and is also competed by unlabeled FLAT DNA.

Example 5

HoxB13 is a Potent Activator of Insulin Gene Expression

In HeLa cells, HoxB13 and the helix-loop-helix factor Pan-1 transactivate the insulin promoter in a highly synergistic fashion. HeLa cells were transfected with 15 μg of a rat insulin promoter/CAT reporter plasmid and: 2 μg of a pCMX/Pan-1 expression vector, or 2 μg of a pCMX/STF-1 expression vector, or both the STF-1 and Pan-1 expression vectors together, or 2 μg of a pCMX/HoxB13 expression vector, or the HoxB13 and Pan-1 expression vectors together. 48 hours after transfection, cell extracts were analyzed for CAT activity.

Figure 5:
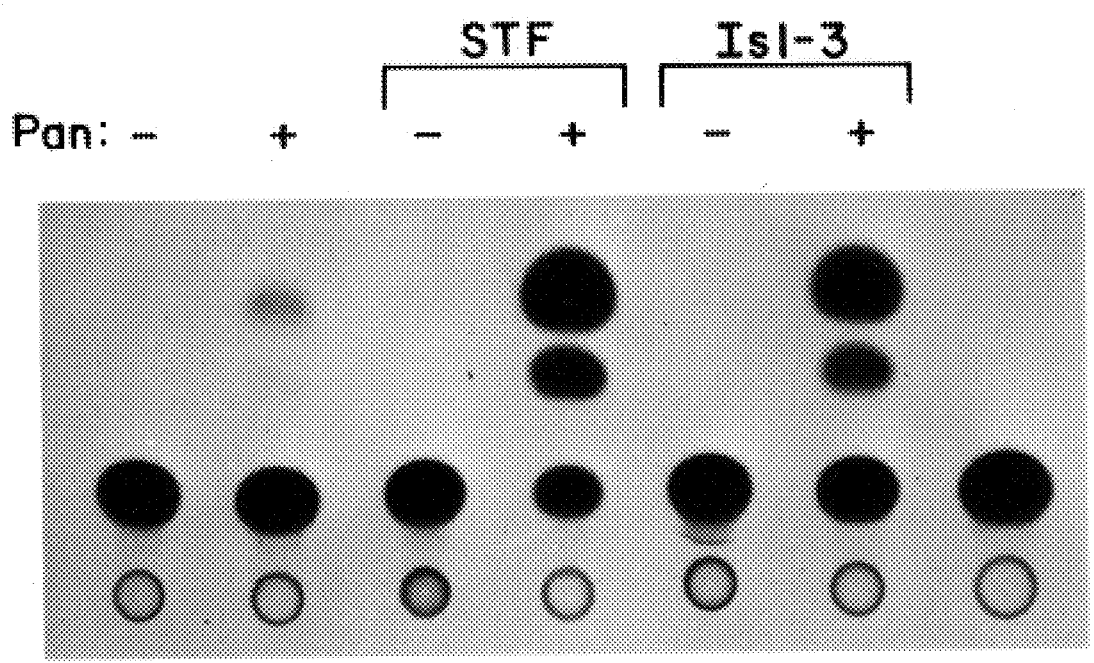
FIG. 5 is a CAT assay which demonstrates that HoxB13, like STF-1, strongly activates the insulin promoter when added in combination with the E-box binding factor Pan-1.

The data indicate that Pan-1 and HoxB13 exhibit a dramatic synergy in their ability to activate the insulin promoter (FIG. 5). The magnitude of synergy between HoxB13 and Pan-1 is similar to that observed with the homeoprotein STF-1, which has also been proposed to be an important regulator of insulin gene expression (Leonard et at, 1993, *Molecular Endocrinology* 7: 1275–1283; Peers et al, 1994, *Molecular Endocrinology* 8: 1798–1806; Petersen et at, 1994, *Proc. Nat. Acad. Sci. USA* 91: 10465–10469).

Example 6

HoxB13 is Sensitive to Stimulation by Calcium

Figure 6:
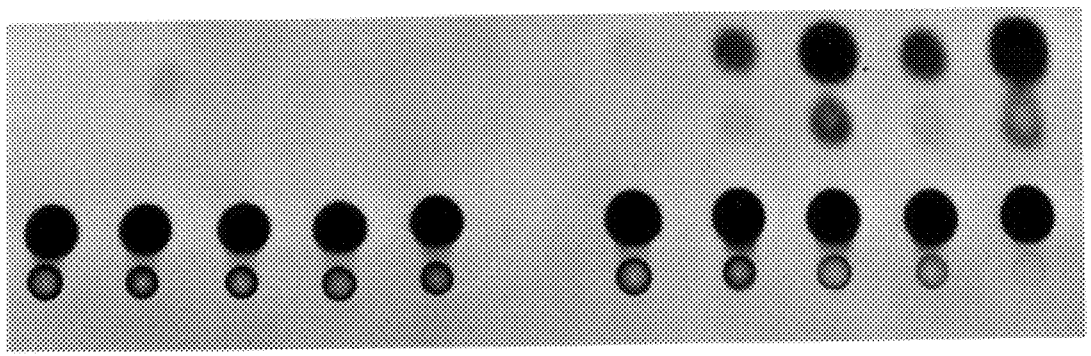
FIG. 6 is a CAT assay which demonstrates that HoxB13 function is increased by a calcium-dependent kinase.

A remarkable distinction of HoxB13 from other homeotic factors lies in the ability of HoxB13 to be selectively modulated by the calcium-dependent kinase CaM kinase IV. HeLa cells were transfected with 15 μg of an insulin promoter/CAT reporter plasmid, and 2 μg of a pCX/STF-1 expression plasmid (with or without 3 μg of a CaM kinase IV expression plasmid), or 2 μg of a HoxB13 expression plasmid (with or without 3 μg of a CaM kinase IV expression plasmid). Where indicated (FIG. 6), transfected cells were also stimulated with 10 μM forskolin or the calcium ionophore A23187. 48 hours after transfection, cell extracts were analyzed for CAT activity.

In the presence of constitutively active CaM kinase IV, HoxB13 was 10-fold more potent with regard to its effect on insulin promoter function in HeLa cells, while STF-1 was unaffected. Since substantial evidence suggests that both calcium influx and the FLAT element participate in glucose-sensitive transcription from the insulin promoter, these characteristics of HoxB13 function are consistent with a possible role of this factor in glucose signaling within the pancreatic β-cell.

Example 7

Identification of Functional Domains of HoxB13

Constructs containing various fragments of the B13 cDNA (generated by PCR) linked in-frame with the Gal4 DNA-binding domain were made as follows:

PCR was performed with the plasmid SK/CIX-1(1.6) and with the following pairs of primers, wherein the number of bp is the expected size of PCR fragments and the range of numbers is the region of HoxB13 encoded by these fragments:

| | |
|---|---|
| Gal Isl-1/FRRA | ~660 bp (1–219) |
| Gal Isl-2/FRRA | ~530 bp (45–219) |
| Gal Isl-3/FRRA | ~430 bp (78–219) |
| Gal Isl-4/FRRA | ~325 bp (113–219) |

10 µl of each PCR product was digested with Bam HI at 37° C. for 5 hours. The enzyme was inactivated at 65° C. for 10 minutes, and the DNA was purified on an SR300 spin column, ethanol precipitated and resuspended in 10 µl. 2 µg plasmid pM2 (containing the DNA binding domain of the yeast factor, Gal4) was likewise digested with Bam HI at 37° C. for 2 hours, was treated with calf intestinal phosphatase (CIP), CIP was inactivated at 65° C. for 10 minutes, and was phenol/chloroform extracted, precipitated and resuspended in 35 µl H$_2$O. 1 µl of vector was ligated to 8 µl of each PCR digest for 2 hours at room temperature. The ligation reactions were used to transform DH5α cells.

Boiling minipreps were prepared from the transformed DH5α cells. DNA was resuspended in 40 µl TE containing RNase A, and 6.5 µl was digested with Bam HI at 37° C. for 1.5 hours. Digests were analyzed on a 0.8% agarose gel. Orientation of the inserts was determined by digesting miniprep DNA with Sma I at 25° C. for 1.5 hours and electrophoresis on a 3% NuSieve/1% agarose gel. Four constructs were picked for large scale preps.

The resulting expression plasmids were termed:

pM2/HoxB13(1–219)
pM2/HoxB13(45–219)
pM2/HoxB13(78–219)
pM2/HoxB13(113–219)

The pM2/HoxB13(1–219) expression vector was also used as a parent vector for the generation of the following additional expression plasmids, by cutting and religating with the indicated restriction enzymes:

pM2/HoxB13(1–154) Apa I (blunted)/Hind III (blunted)
pM2/HoxB13(1–95) Sac I(blunted)/Hind III (blunted)
pM2/HoxB13(1–59) Pst I Hamster BHK cells were transfected with 1.6 µg of a G5B-CAT reporter containing 5 binding sites for the yeast factor Gal4, along with 0.4 µg of the pM2 parent plasmid, or the above-listed pM2/HoxB13 expression plasmids containing various portions of the HoxB13 coding region. For comparison to the activation domain of STF-1, a sample cotransfected with the expression plasmid pM2/STF-1 (1–147) was also included. 48 hours after transfection, cell extracts were tested for CAT activity.

Figure 7:
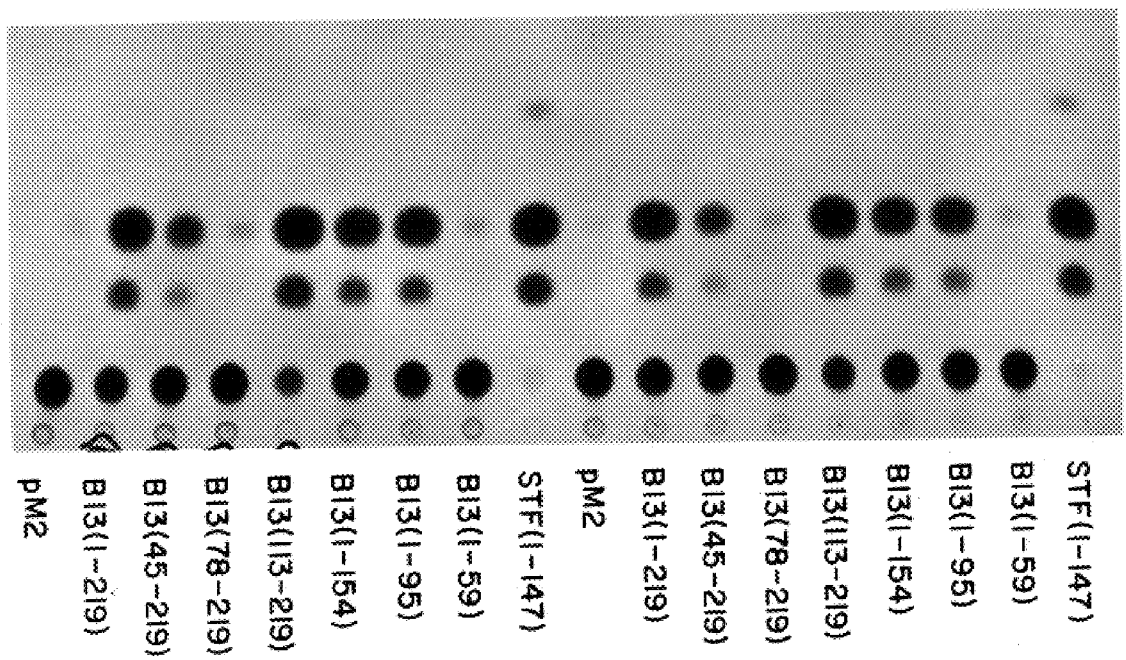
FIG. 7 is a CAT assay using various fragments of B13 cDNA linked in-frame with the Gal4 DNA-binding domain.
Figure 11:
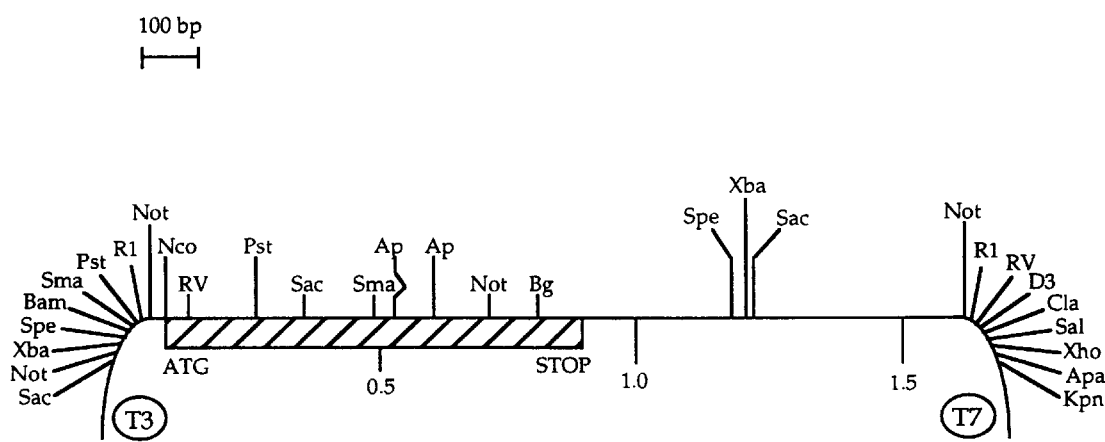
FIG. 11 is a restriction map of SK/B13, which is an SKII(+) vector containing an ISL-3 insert of approximately 1.6 kb. A T7 primer can be used to make an antisense probe. Linearizing with Not I gives a 800 bp probe, while linearizing with Nco I gives a 1.5 kb probe. There are no sites for the following enzymes: Bam HI, Hind III, Sal I, Xho I and Pvu II.
Figure 12:
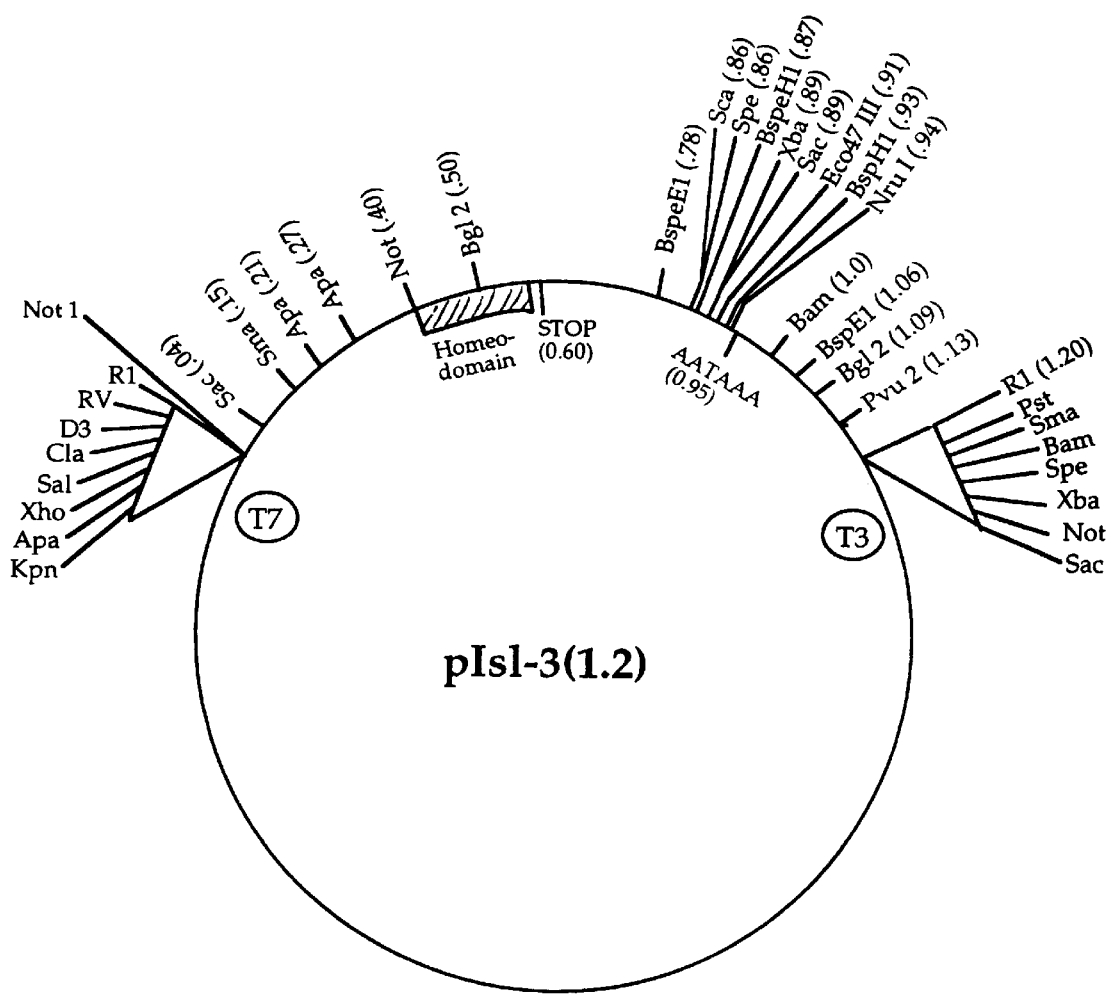
FIG. 12 is a restriction map of pIsl-3 m which is the SKII vector containing a 1.2 kb fragment containing the coding sequence for a 202 amino acid open reading frame for Isl-3.

As shown in FIG. 7, plasmids encoding the region from 1–95 retain full activity, whereas further deletion (i.e., 1–59) results in complete loss of activity. Conversely, deletion of the N-terminal 45 amino acids of B13 (i.e., 45–219) results in complete loss of activity. Hence, the region of HoxB13 from amino acids 1–95 contains a potent activation domain.

Example 8

Identification of the Chromosomal Location of HoxB13

To map the chromosomal location of HoxB13, PCR was used to screen a panel of DNAs from mouse/human or hamster/human hybrid cell lines, each of which had retained only one human chromosome. The primer used for this purpose were:

CIXSOME-1 5' GGTACCTGCAAATGCTGCCTTCCA 3' (SEQ ID NO:11)

CIXSOME-2 5' TGGGGAGAGCGAGCTGAGTGC 3' (SEQ ID NO:12), which roughly flank exon 1 and do not amplify bands from mouse or hamster DNA. A band of the predicted size (674 bp) is seen only in DNAs from chromosome 17-containing hybrids. Hence human HoxB13 resides on chromosome 17. A similar analysis with DNA from cells containing only portions of chromosome 17 indicated that human HoxB13 lies within 17q11→17q23.

The human HoxB complex lies on chromosome 17q21. The mapping of HoxB13, together with its remarkable homology to paralog 13 of other Hox complexes, suggests that it does indeed reside within the HoxB complex. To test this, three yeast artificial chromosome (YAC) clones known to contain at least a portion of the HoxB locus were examined for the presence of HoxB13 by PCR analysis. Two primer pairs (gCIX-1/hgCIX-11 or hgCIX-11/hgCIX-12) were used, and both pairs successfully amplified a product of the correct size with two of the YAC clones (Hox2 B215C9 and Hox2 B195E7). Neither primer set was able to amplify the predicted band from Hox2 B160B1. These data clearly indicate that HoxB 13 does indeed map at or very near the HoxB complex. This implies that HoxB13 may also provide a critical function in anterior-posterior pattern formation during embryogenesis.

FIGS. 8 and 9 illustrate that cell lines 498 (which contains all of chromosome 17), 500 and 600 are positive for 17q21 localization. Cell lines 660 (p arm of chromosome) and 659 (17q23—telomere) do not amplify. The HoxB13 sequence is not amplified from YAC Hox2 B160B1.

The human HoxB13 gene maps to 17q11→q23, which contains the HoxB complex. HoxB13 shares 75–80% homology with the homeotic selector genes HoxA13, HoxC13 and HoxD13 (FIG. 8). If this factor is indeed paralogous to HoxA13, HoxC13 and HoxD13, it likely exhibits a caudal domain of expression and function along the anterior-posterior axes of the developing embryo.

Example 9

Analysis of Blood Samples for Identification of Variant Alleles

That chronic impairment of glucose-sensitive transcription from the insulin gene may contribute to the insufficient β-cell function seen in type II diabetics is examined. Because STF-1 and HoxB13 appear to function by recognizing a portion of the insulin gene that has been implicated in glucose-sensitive transcription, the possibility that type II diabetic individuals may contain variant forms of either of these genes is investigated.

Cells are isolated from blood drawn from patients undergoing vascular surgery. Because many of these patients are expected to be type II diabetics, it can be determined, using PCR to amplify genomic sequences corresponding to HoxB13 or STF-1, whether a correlation exists between the disease and a particular genetic phenotype.

30 patients between the ages of 30 and 80, who have type I or type II diabetes, or are being used as controls, and are undergoing elective vascular surgery have 60 ml of blood drawn by venipunlcture. No patients who have clinically active infections, bleeding disorders or who use anticoagulants, or who are seriously or terminally ill, are used.

Genomic DNA is isolated from the patients' blood using a standardized kit (Pharmacia). Primers which hybridize to flanking regions, or regions at the 5' and 3' ends of the HoxB13 and/or STF-1 gene are used to amplify the gene sequences by PCR using Taq polymerase and suitable buffers, temperatures, reaction times and number of cycles for annealing, synthesis, and denaturation steps (to be determined empirically). The PCR products are digested with a panel of restriction enzymes to identify any restriction fragment polymorphisms (RFLPs), and/or are sequenced using the dideoxy method and suitable primers. Gene sequences from samples of control patients and diabetic patients are compared to determine whether particular genetic variations appear to predispose individuals to either type I or type II diabetes.

Example 10

Analysis of Developmental Expression of HoxB13 in Rodent Embryos

The presence of HoxB13 expression during embryogenesis is first evaluated initially by PCR analysis of rodent embryos from day 9 post-coitus (p.c.) to day 19 p.c. Once the time of expression is determined, in situ hybridization of whole-mounit embryos is performed to localize the major structures wherein HoxB13 is expressed. This serves to evaluate the expression of HoxB13 in the embryonic pancreas, as well as in structures which are crucial for axial development of the embryo.

Example 11

Control of HoxB13 Expression in Islet Cells

HoxB13 expression in islet cell lines and cultured neonatal or adult pancreatic islets is evaluate by Northern blot analysis, RNase protection assay, and/or PCR. In addition, RNA is evaluated from cells stimulated with agents known to be crucial in islet physiology, such as shifting glucose concentration from 2 mM to 16 mM, or incubation with calcium ionophore (A23187), the adenylate cyclase activator forskolin, arginine, or KCl (membrane depolarization).

The molecular mechanism behind such control is evaluated in part by cloning the promoter of HoxB13 adjacent to a "reporter" sequence, such as that encoding the firefly enzyme luciferase, and determining which regions of the promoter are necessary and sufficient to allow the reporter to be regulated similarly to the endogenous HoxB13 gene.

While the invention has been described and illustrated herein by references to various specific material, procedures and examples, it is understood that the invention is not restricted to the particular material combinations of material, and procedures selected for that purpose. Numerous variations of such details can be implied as will be appreciated by those skilled in the art.

This invention may be embodied in other forms or carried out in other ways without departing from the spirit or essential characteristics thereof. The present disclosure is therefore to be considered as in all respects illustrative and not restrictive, the scope of the invention being indicated by the appended Claims, and all changes which come within the meaning and range of equivalency are intended to be embraced therein.

What is claimed is:

1. An isolated mammalian HoxB13 polypeptide which regulates insulin gene expression comprising an amino acid sequence as set forth in SEQ ID NO:2.

2. The isolated HoxB13 polypeptide of claim 1, wherein the polypeptide is labeled with a detectable label.

3. The homeoprotein regulator of insulin gene expression of claim 2 wherein the label is selected from enzymes, chemicals which fluoresce and radioactive elements.

4. The isolated HoxB13 polypeptide of claim 1, wherein the polypeptide is in a phosphorylated form.

5. An isolated mammalian HoxB13 polypeptide which regulates insulin gene expression comprising an amino acid sequence as set forth in SEQ ID NO:5.

6. The isolated HoxB13 polypeptide of claim 5, wherein the polypeptide is labeled with a detectable label.

7. The isolated HoxB13 polypeptide of claim 5, wherein the polypeptide is in a phosphorylated form.

8. An isolated mammalian HoxB13 polypeptide which regulates insulin gene expression consisting of an amino acid sequence as set forth in SEQ ID NO:5 beginning with methionine at position 1 and ending with serine at position 95.

9. An isolated detectably labeled mammalian HoxB13 polypeptide which regulates insulin gene expression consisting of a detectable label and an amino acid sequence as set forth in SEQ ID NO:5 beginning with methionine at position 1 and ending with serine at position 95.

10. The isolated HoxB13 polypeptide of claim 8, wherein the polypeptide is in a phosphorylated form.

* * * * *